(12) United States Patent
Gharib et al.

(10) Patent No.: US 9,295,396 B2
(45) Date of Patent: Mar. 29, 2016

(54) NEUROPHYSIOLOGIC MONITORING SYSTEM

(75) Inventors: James Gharib, San Diego, CA (US);
Allen Farquhar, San Diego, CA (US);
Doug Layman, San Diego, CA (US);
Thomas Scholl, San Diego, CA (US);
Albert Kim, San Diego, CA (US);
Albert Pothier, San Diego, CA (US);
Patrick Miles, San Diego, CA (US);
Josef Gorek, Oakland, CA (US); Mark Peterson, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/597,160

(22) Filed: Aug. 28, 2012

(65) Prior Publication Data
US 2013/0090568 A1 Apr. 11, 2013

Related U.S. Application Data

(63) Continuation of application No. 12/080,630, filed on Apr. 3, 2008, now Pat. No. 8,255,045.

(60) Provisional application No. 60/921,718, filed on Apr. 3, 2007, provisional application No. 61/000,354, filed on Oct. 24, 2007.

(51) Int. Cl.
| | |
|---|---|
| *A61B 5/04* | (2006.01) |
| *A61B 5/05* | (2006.01) |
| *A61B 18/04* | (2006.01) |
| *A61B 18/18* | (2006.01) |
| *A61N 1/00* | (2006.01) |
| *A61B 5/0488* | (2006.01) |
| *A61B 5/00* | (2006.01) |

(Continued)

(52) U.S. Cl.
CPC ........... *A61B 5/04001* (2013.01); *A61B 5/0488* (2013.01); *A61B 5/4893* (2013.01); *A61B 17/1671* (2013.01); *A61N 1/08* (2013.01); *A61B 5/0492* (2013.01); *A61B 5/05* (2013.01); *A61B 5/407* (2013.01); *A61B 17/1626* (2013.01); *A61B 17/1757* (2013.01); *A61B 2017/00022* (2013.01); *A61B 2017/00026* (2013.01); *A61N 1/0551* (2013.01); *A61N 1/36014* (2013.01)

(58) Field of Classification Search
CPC .... A61B 5/05; A61B 5/4893; A61B 17/1671; A61B 2017/0256
USPC .......... 600/372, 373, 546, 547, 554; 606/116, 606/117
See application file for complete search history.

(56) References Cited

U.S. PATENT DOCUMENTS

| | | |
|---|---|---|
| 208,227 A | 9/1878 | Dorr |
| 972,983 A | 10/1910 | Arthur |

(Continued)

OTHER PUBLICATIONS

"Electromyography System," International Search report from International Application No. PCT/US00/32329, Apr. 27, 2001, 9 pages.

(Continued)

*Primary Examiner* — Sean Dougherty
(74) *Attorney, Agent, or Firm* — Jonathan Spangler; Heather Prado

(57) ABSTRACT

The present invention relates to a system and methods generally aimed at surgery. More particularly, the present invention is directed at a system and related methods for performing surgical procedures and assessments involving the use of neurophysiology.

19 Claims, 67 Drawing Sheets

(51) Int. Cl.
  *A61N 1/08* (2006.01)
  *A61B 17/16* (2006.01)
  *A61B 17/17* (2006.01)
  *A61B 17/00* (2006.01)
  *A61N 1/05* (2006.01)
  *A61N 1/36* (2006.01)
  *A61B 5/0492* (2006.01)

(56) References Cited

U.S. PATENT DOCUMENTS

| | | |
|---|---|---|
| 1,328,624 A | 1/1920 | Graham |
| 1,548,184 A | 8/1925 | Cameron |
| 2,704,064 A | 3/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Colyer |
| 3,785,368 A | 1/1974 | McCarthy et al. |
| 3,830,226 A | 8/1974 | Staub |
| 3,851,641 A | 12/1974 | Toole et al. |
| 3,957,036 A | 5/1976 | Normann |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,252,130 A | 2/1981 | Le Pivert |
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,018 A | 6/1986 | Rantala |
| 4,633,889 A | 1/1987 | Talalla et al. |
| 4,658,835 A | 4/1987 | Pohndorf |
| 4,744,371 A | 5/1988 | Harris |
| 4,759,377 A | 7/1988 | Dykstra |
| 4,784,150 A | 11/1988 | Voorhies et al. |
| 4,807,642 A | 2/1989 | Brown |
| 4,892,105 A | 1/1990 | Prass |
| 4,926,865 A | 5/1990 | Oman |
| 4,962,766 A | 10/1990 | Herzon |
| 4,964,411 A | 10/1990 | Johnson et al. |
| 5,007,902 A | 4/1991 | Witt |
| 5,058,602 A | 10/1991 | Brody |
| 5,081,990 A | 1/1992 | Deletis |
| 5,092,344 A | 3/1992 | Lee |
| 5,127,403 A | 7/1992 | Brownlee |
| 5,161,533 A | 11/1992 | Prass et al. |
| 5,196,015 A | 3/1993 | Neubardt |
| 5,220,920 A | 6/1993 | Gharib |
| RE34,390 E | 9/1993 | Culver |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,299,563 A | 4/1994 | Seton |
| 5,312,417 A | 5/1994 | Wilk |
| 5,313,956 A | 5/1994 | Knutsson et al. |
| 5,327,902 A | 7/1994 | Lemmen |
| 5,333,618 A | 8/1994 | Lekhtman et al. |
| 5,375,067 A | 12/1994 | Berchin |
| 5,383,876 A | 1/1995 | Nardella |
| 5,450,845 A | 9/1995 | Axelgaard |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,540,235 A | 7/1996 | Wilson |
| 5,549,656 A | 8/1996 | Reiss |
| 5,560,372 A | 10/1996 | Cory |
| 5,566,678 A | 10/1996 | Cadwell |
| 5,579,781 A | 12/1996 | Cooke |
| 5,593,429 A | 1/1997 | Ruff |
| 5,599,279 A | 2/1997 | Slotman |
| 5,601,608 A | 2/1997 | Mouchawar |
| 5,630,813 A | 5/1997 | Kieturakis |
| 5,671,752 A | 9/1997 | Sinderby et al. |
| 5,707,359 A | 1/1998 | Bufalini |
| 5,711,307 A | 1/1998 | Smits |
| 5,728,046 A | 3/1998 | Mayer |
| 5,741,253 A | 4/1998 | Michelson |
| 5,758,643 A | 6/1998 | Wong et al. |
| 5,759,159 A | 6/1998 | Masreliez |
| 5,772,661 A | 6/1998 | Michelson |
| 5,775,331 A | 7/1998 | Raymond et al. |
| 5,776,144 A | 7/1998 | Leysieffer et al. |
| 5,779,642 A | 7/1998 | Nightengale |
| 5,785,658 A | 7/1998 | Benaron et al. |
| 5,797,854 A | 8/1998 | Hedgecock |
| 5,806,522 A | 9/1998 | Katims |
| 5,807,272 A | 9/1998 | Kun et al. |
| 5,814,073 A | 9/1998 | Bonutti |
| 5,830,151 A | 11/1998 | Hadzic et al. |
| 5,851,191 A | 12/1998 | Gozani et al. |
| 5,853,373 A | 12/1998 | Griffith et al. |
| 5,860,973 A | 1/1999 | Michelson |
| 5,862,314 A | 1/1999 | Jeddeloh |
| 5,872,314 A | 2/1999 | Clinton |
| 5,885,219 A | 3/1999 | Nightengale |
| 5,888,196 A | 3/1999 | Bonutti |
| 5,902,231 A | 5/1999 | Foley et al. |
| 5,928,139 A | 7/1999 | Koros et al. |
| 5,928,158 A | 7/1999 | Aristides |
| 5,928,159 A | 7/1999 | Eggers et al. |
| 5,935,131 A | 8/1999 | Bonutti |
| 5,938,688 A | 8/1999 | Schiff |
| 5,947,964 A | 9/1999 | Eggers et al. |
| 5,976,094 A | 11/1999 | Gozani |
| 6,004,262 A | 12/1999 | Putz et al. |
| 6,011,985 A | 1/2000 | Athan |
| 6,026,323 A | 2/2000 | Skladnev et al. |
| 6,027,456 A | 2/2000 | Feler et al. |
| 6,038,469 A | 3/2000 | Karlsson et al. |
| 6,038,477 A | 3/2000 | Kayyali |
| 6,050,992 A | 4/2000 | Nichols |
| 6,074,343 A | 6/2000 | Nathanson et al. |
| 6,104,957 A | 8/2000 | Alo et al. |
| 6,104,960 A | 8/2000 | Duysens et al. |
| 6,119,068 A | 9/2000 | Kannonji |
| 6,120,503 A | 9/2000 | Michelson |
| 6,128,576 A | 10/2000 | Nishimoto |
| 6,132,386 A | 10/2000 | Gozani et al. |
| 6,132,387 A | 10/2000 | Gozani et al. |
| 6,135,965 A | 10/2000 | Turner |
| 6,139,493 A | 10/2000 | Koros et al. |
| 6,146,335 A | 11/2000 | Gozani |
| 6,161,047 A | 12/2000 | King et al. |
| 6,181,961 B1 | 1/2001 | Prass |
| 6,206,826 B1 | 3/2001 | Mathews et al. |
| 6,224,549 B1 | 5/2001 | Drongelen |
| 6,259,945 B1 | 7/2001 | Epstein et al. |
| 6,266,558 B1 | 7/2001 | Gozani et al. |
| 6,273,905 B1 | 8/2001 | Streeter |
| 6,292,701 B1 | 9/2001 | Prass et al. |
| 6,306,100 B1 | 10/2001 | Prass |
| 6,312,392 B1 | 11/2001 | Herzon |
| 6,325,764 B1 | 12/2001 | Griffith et al. |
| 6,334,068 B1 | 12/2001 | Hacker |
| 6,337,994 B1 | 1/2002 | Stoianovici et al. |
| 6,393,325 B1 | 5/2002 | Mann et al. |
| 6,407,335 B1 | 6/2002 | Franklin-Lees et al. |
| 6,425,859 B1 | 7/2002 | Foley et al. |
| 6,425,901 B1 | 7/2002 | Zhu et al. |
| 6,451,015 B1 | 9/2002 | Rittman et al. |
| 6,466,817 B1 | 10/2002 | Kaula et al. |

(56) References Cited

U.S. PATENT DOCUMENTS

| | | | |
|---|---|---|---|
| 6,500,128 B2 | 12/2002 | Marino |
| 6,535,759 B1 | 3/2003 | Epstein et al. |
| 6,564,078 B1 | 5/2003 | Marino et al. |
| 6,579,244 B2 | 6/2003 | Goodwin |
| 6,593,528 B2 | 7/2003 | Franklin-Lees et al. |
| 6,719,692 B2 | 4/2004 | Kleffner et al. |
| 6,760,616 B2 | 7/2004 | Hoey et al. |
| 6,796,985 B2 | 9/2004 | Bolger et al. |
| 6,819,956 B2 | 11/2004 | DiLorenzo |
| 6,829,508 B2 | 12/2004 | Schulman et al. |
| 6,849,047 B2 | 2/2005 | Goodwin |
| 6,855,105 B2 | 2/2005 | Jackson, III |
| 6,902,569 B2 | 6/2005 | Parmer et al. |
| 6,926,728 B2 | 8/2005 | Zucherman et al. |
| 6,929,606 B2 | 8/2005 | Ritland |
| 7,047,082 B1 | 5/2006 | Schrom et al. |
| 7,050,848 B2 | 5/2006 | Hoey et al. |
| 7,079,883 B2 * | 7/2006 | Marino et al. ............ 600/373 |
| 7,089,059 B1 | 8/2006 | Pless |
| D533,875 S | 12/2006 | Miles et al. |
| 7,177,677 B2 | 2/2007 | Kaula et al. |
| 7,207,949 B2 | 4/2007 | Miles et al. |
| 7,255,680 B1 | 8/2007 | Gharib |
| 7,470,236 B1 | 12/2008 | Kelleher et al. |
| 7,522,953 B2 | 4/2009 | Kaula et al. |
| 7,582,058 B1 | 9/2009 | Miles et al. |
| 7,657,308 B2 | 2/2010 | Miles et al. |
| 7,664,544 B2 | 2/2010 | Miles et al. |
| 7,691,057 B2 | 4/2010 | Miles et al. |
| 7,706,843 B2 | 4/2010 | Kaplan |
| 7,819,801 B2 | 10/2010 | Miles et al. |
| 7,857,813 B2 | 12/2010 | Schmitz et al. |
| 7,878,981 B2 | 2/2011 | Strother et al. |
| 7,887,538 B2 | 2/2011 | Bleich et al. |
| 7,896,815 B2 | 3/2011 | Thrope et al. |
| 7,905,840 B2 | 3/2011 | Pimenta et al. |
| 7,938,830 B2 | 5/2011 | Saadat et al. |
| 7,963,927 B2 | 6/2011 | Kelleher et al. |
| 8,068,912 B2 | 11/2011 | Kaula et al. |
| 2001/0039949 A1 | 11/2001 | Loubser |
| 2001/0056280 A1 | 12/2001 | Underwood et al. |
| 2002/0007129 A1 | 1/2002 | Marino |
| 2002/0072686 A1 | 6/2002 | Hoey et al. |
| 2002/0123780 A1 | 9/2002 | Grill et al. |
| 2002/0134570 A1 | 9/2002 | Franklin-Lees et al. |
| 2002/0161415 A1 | 10/2002 | Cohen et al. |
| 2002/0193843 A1 | 12/2002 | Hill et al. |
| 2003/0032966 A1 | 2/2003 | Foley et al. |
| 2003/0105503 A1 | 6/2003 | Marino |
| 2004/0199084 A1 | 10/2004 | Kelleher et al. |
| 2004/0203490 A1 | 10/2004 | Kaplan |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0149035 A1 | 7/2005 | Pimenta et al. |
| 2005/0182454 A1 | 8/2005 | Gharib et al. |
| 2005/0192575 A1 | 9/2005 | Pacheco |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0224078 A1 | 10/2006 | Hoey et al. |
| 2007/0016097 A1 * | 1/2007 | Farquhar et al. ............ 600/546 |
| 2007/0021682 A1 * | 1/2007 | Gharib et al. ............ 600/546 |
| 2007/0168051 A1 * | 7/2007 | Bronnenberg ..... H04N 21/4332 700/20 |
| 2007/0168852 A1 * | 7/2007 | Erol ............... G06F 17/30044 715/234 |
| 2007/0168862 A1 * | 7/2007 | Hunt ............... H05B 37/029 715/705 |
| 2007/0174758 A1 * | 7/2007 | Ando ............... G11B 20/00086 715/203 |
| 2007/0174917 A1 * | 7/2007 | Guruswamy ....... H04L 63/1433 726/25 |
| 2007/0198062 A1 | 8/2007 | Miles et al. |
| 2007/0293782 A1 | 12/2007 | Marino |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0097164 A1 | 4/2008 | Miles et al. |
| 2008/0167574 A1 | 7/2008 | Farquhar et al. |
| 2008/0221473 A1 | 9/2008 | Calancie et al. |
| 2009/0018399 A1 | 1/2009 | Martinelli |
| 2009/0018610 A1 | 1/2009 | Gharib et al. |
| 2009/0054804 A1 | 2/2009 | Gharib et al. |
| 2009/0105604 A1 | 4/2009 | Bertagnoli et al. |
| 2009/0124860 A1 | 5/2009 | Miles et al. |
| 2009/0177112 A1 | 7/2009 | Gharib et al. |
| 2009/0192403 A1 | 7/2009 | Gharib et al. |
| 2009/0204016 A1 | 8/2009 | Gharib et al. |
| 2009/0204176 A1 | 8/2009 | Miles et al. |
| 2009/0209879 A1 | 8/2009 | Kaula et al. |
| 2009/0259108 A1 | 10/2009 | Miles et al. |
| 2010/0010367 A1 | 1/2010 | Foley et al. |
| 2010/0036384 A1 | 2/2010 | Gorek et al. |
| 2010/0069783 A1 | 3/2010 | Miles et al. |
| 2010/0076335 A1 | 3/2010 | Gharib et al. |
| 2010/0094093 A1 | 4/2010 | Miles et al. |
| 2010/0105986 A1 | 4/2010 | Miles et al. |
| 2010/0105987 A1 | 4/2010 | Miles et al. |
| 2010/0113884 A1 | 5/2010 | Miles et al. |
| 2010/0130827 A1 | 5/2010 | Pimenta et al. |
| 2010/0137690 A1 | 6/2010 | Miles et al. |
| 2010/0152603 A1 | 6/2010 | Miles et al. |
| 2010/0152604 A1 | 6/2010 | Kaula et al. |
| 2010/0160738 A1 | 6/2010 | Miles et al. |
| 2010/0174146 A1 | 7/2010 | Miles et al. |
| 2010/0174147 A1 | 7/2010 | Miles et al. |
| 2010/0174148 A1 | 7/2010 | Miles et al. |
| 2010/0249644 A1 | 9/2010 | Miles et al. |
| 2010/0273738 A1 | 10/2010 | Valcke et al. |
| 2010/0312103 A1 | 12/2010 | Gorek et al. |

OTHER PUBLICATIONS

"Nerve Proximity and Status Detection System and Method," International Search Report from International Application No. PCT/US01/18606, Oct. 18, 2001, 6 pages.

"Relative Nerve Movement and Status Detection System and Method," International Search Report from International Application No. PCT/US01/18579, Jan. 15, 2002, 6 pages.

"System and Method for Determining Nerve Proximity Direction and Pathology During Surgery," International Search Report from International Application No. PCT/US02/22247, Mar. 27, 2003, 4 pages.

"System and Methods for Determining Nerve Direction to a Surgical Instrument," International Search Report from International Application No. PCT/US03/02056, Aug. 12, 2003, 5 pages.

"Systems and Methods for Performing Percutaneous Pedicle Integrity Assessments," International Search Report from International Application No. PCT/US02/35047, Aug. 11, 2003, 5 pages.

"Systems and Methods for Performing Surgery Procedures and Assessments," International Search Report from International Application No. PCT/US02/30617, Jun. 5, 2003, 4 pages.

"Systems and Methods for Performing Neurophysiologic Assessments During Spine Surgery," International Search Report from International Application No. PCT/US06/03966, Oct. 23, 2006, 5 pages.

"Multi-Channel Stimulation Threshold Detection Algorithm for Use in Neurophysiology Monitoring," International Search Report from International Application No. PCT/US06/37013, Mar. 19, 2007, 6 pages.

"Neurovision SE Nerve Locator/Monitor," RLN Systems Inc. Operator's Manual, 1999, 22 pages.

(56) References Cited

OTHER PUBLICATIONS

Calancie et al., "Stimulus-Evoked EMG Monitoring During Transpedicular Lumbosacral Spine Instrumentation," *Spine*, 1994, 19(24): 2780-2786.

Holland et al., "Higher Electrical Stimulus Intensities are Required to Activate Chronically Compressed Nerve Roots. Implications for Intraoperative Electromyographic Pedicle Screw Testing," *Spine*, 1998, 23(2): 224-227.

"Neurophysiologic Monitoring System," International Search Report and the Written Opinion from International Application No. PCT/US08/04427, Jul. 28, 2008, 6 pages.

* cited by examiner

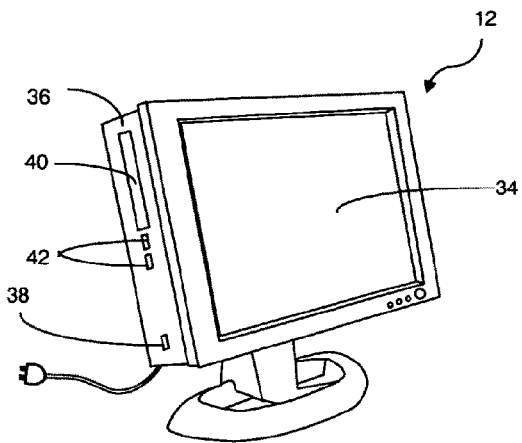
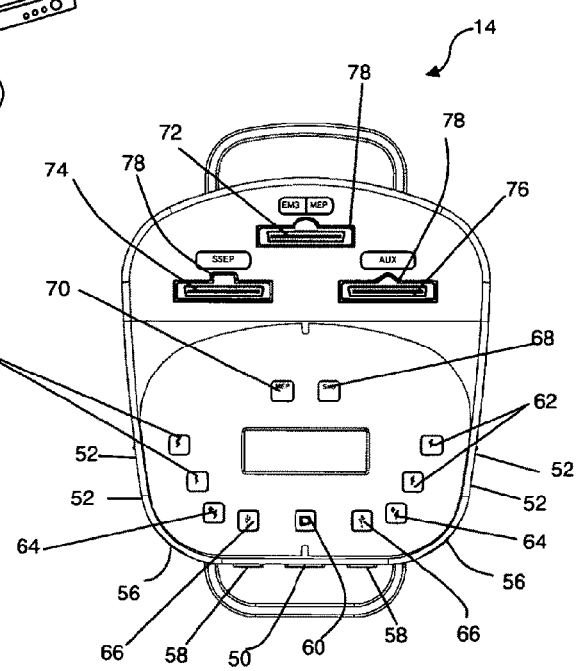
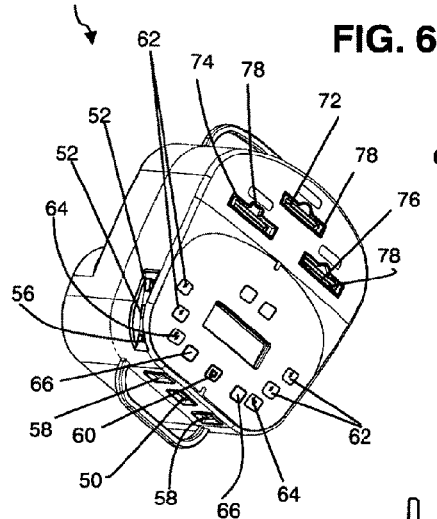
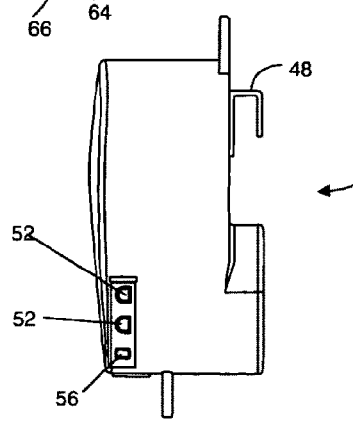
FIG. 6
FIG. 7
FIG. 8
FIG. 9

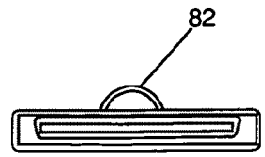 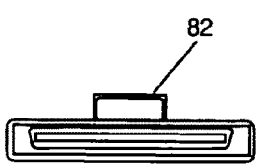 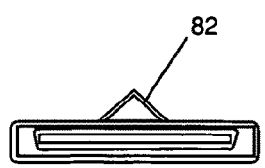
FIG. 11A  FIG. 11B  FIG. 11C
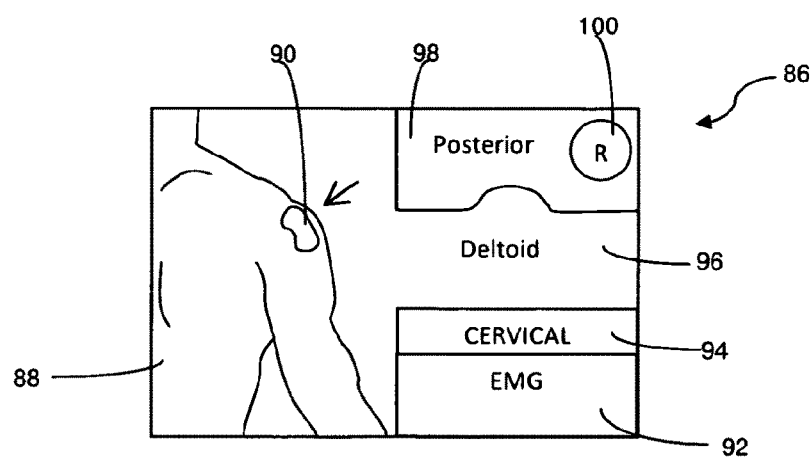
FIG. 12
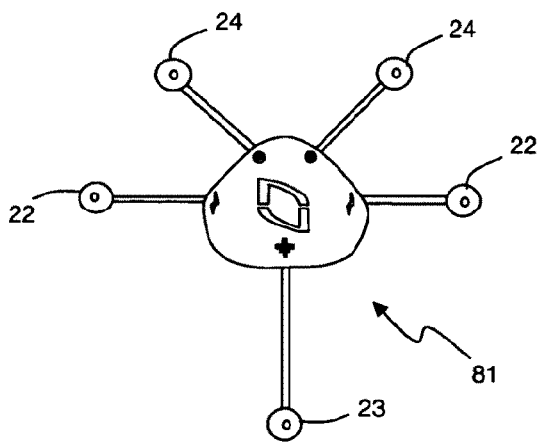 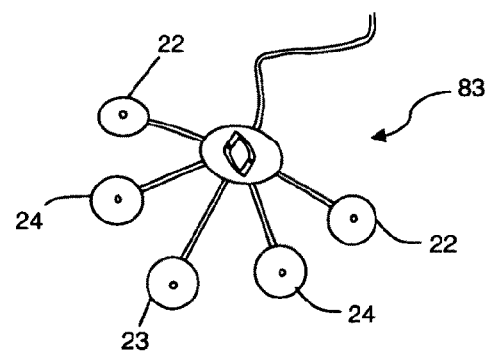
FIG. 13A  FIG. 13B

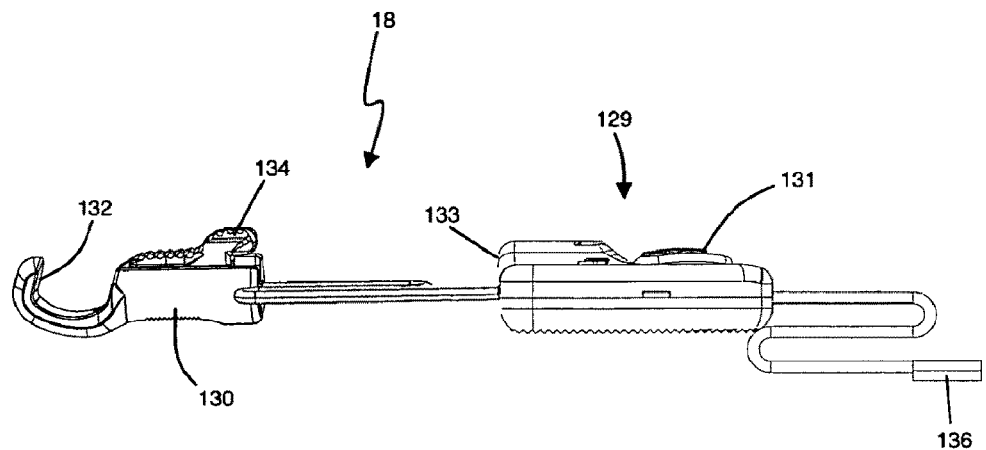
FIG. 18
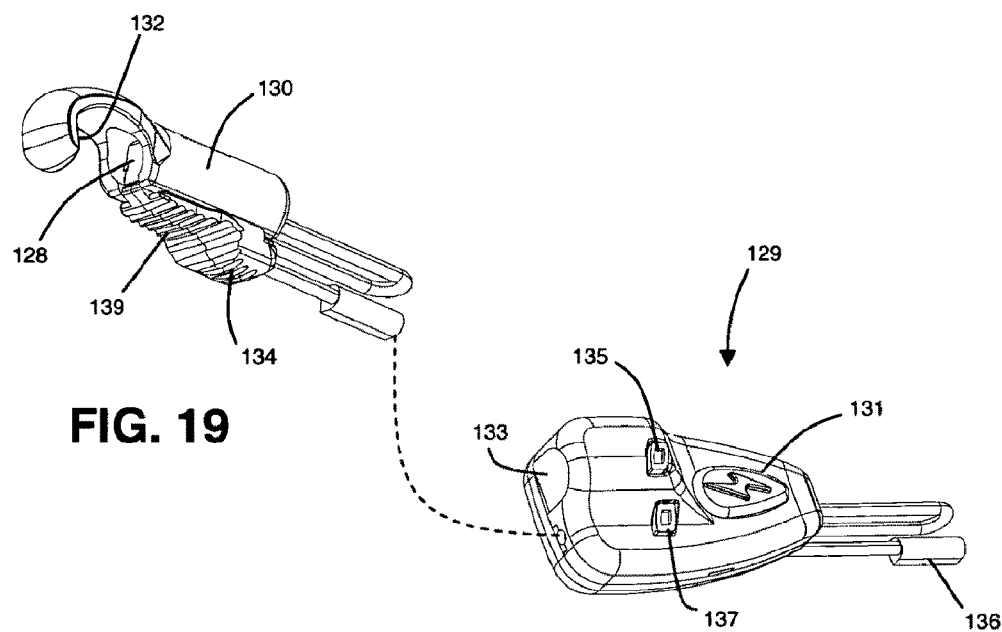
FIG. 19
FIG. 20

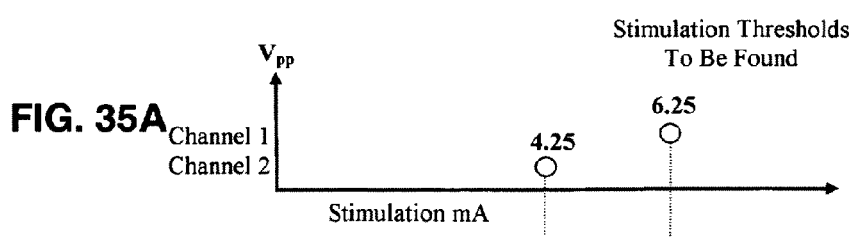
FIG. 35A
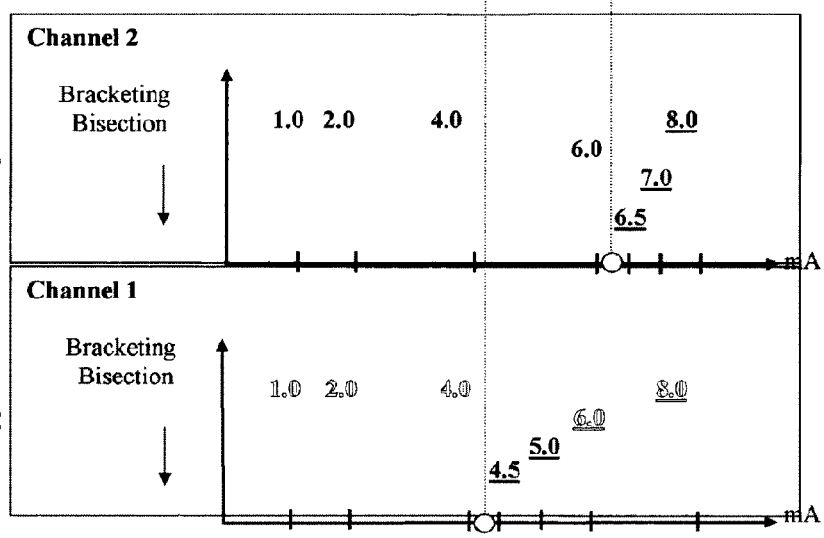
FIG. 35B
FIG. 35C
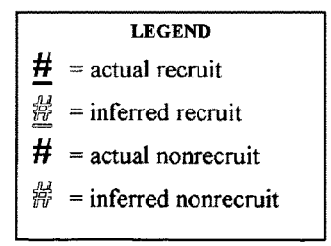

NEUROPHYSIOLOGIC MONITORING SYSTEM

CROSS-REFERENCES TO RELATED APPLICATIONS

This application is a continuation of U.S. patent application Ser. No. 12/080,630, filed on Apr. 3, 2008 (now issued as U.S. Pat. No. 8,255,045), which claims priority to U.S. Provisional Patent Application Serial Nos. 60/921,718, filed Apr. 3, 2007 and 61/000,354, filed Oct. 24, 2007, the entire contents each of which are hereby expressly incorporated by reference into this disclosure as if set forth fully herein.

BACKGROUND OF THE INVENTION

I. Field of the Invention

The present invention relates to a system and methods generally aimed at surgery. More particularly, the present invention is directed at a system and related methods for performing surgical procedures and assessments involving the use of neurophysiology.

II. Description of Related Art

Neurophysiology monitoring has become an increasingly important adjunct to surgical procedures where neural tissue may be at risk. Spinal surgery, in particular, involves working close to delicate tissue in and surrounding the spine, which can be damaged in any number of different ways. For example, an exiting nerve root may be comprised if surgical instruments have to pass near or close to the nerve while accessing the surgical target site in the spine. A spinal nerve and/or exiting nerve root may also be compromised if a pedicle screw, used often to secure fixation of multiple vertebra relative to each other, breaches the cortical layer of the pedicle. Surgeries targeting the spine may also require the retraction of nerve and/or vascular tissue out of the operative corridor. While doing so is necessary, there is a possibility of damaging nerve tissue through over retraction and/or a decreased supply of blood reaching the tissue due to the impingement of the retractor against the vascular tissue. Various neurophysiological techniques have been attempted and developed to monitor delicate nerve tissue during surgery in attempts to reduce the risk inherent in spine surgery (and surgery in general). Because of the complex structure of the spine and nervous system no single monitoring technique has been developed that may adequately assess the risk to nervous tissue in all situations and complex techniques are often utilized in conjunction one or more other complex monitoring techniques. EMG monitoring, for example, may be used to detect the presence of nerve roots near a surgical instrument or a breach formed in a pedicle wall. EMG monitoring is not, however, very effective when cord monitoring is required.

When cord monitoring is required one of motor evoked potential (MEP) and somatosensory evoked potential (SSEP) monitoring is often chosen. While both MEP and SSEP monitoring can be quite effective, MEP monitors the ventral column of the spinal cord and SSEP monitors the dorsal column. Danger to nerve tissue that might then be detected using one these methods may be missed by the other, and vice versa. Thus it may be most effective to use both MEP and SSEP monitoring during the same procedure, while still potentially needing EMG monitoring as well.

EMG, MEP, and SSEP involve complex analysis and specially trained neurophysiologists are generally called upon to perform the monitoring. Even though performed by specialists, interpreting the complex waveforms in this fashion is nonetheless disadvantageously prone to human error and can be disadvantageously time consuming, adding to the duration of the operation and translating into increased health care costs. Even more costly is the fact that the neurophysiologist is required in addition to the actual surgeon performing the spinal operation. Putting the difficulties associated with human interpretation of EMG, MEP, and SSEP monitoring aside, combining such testing in the OR generally requires multiple products to accommodate t the differing requirements of each. This is disadvantageous when space is often as such a premium in the operating rooms of today. The present invention is directed at eliminating, or at least reducing the effects of, the above-described problems with the prior art.

SUMMARY OF THE INVENTION

The present invention includes a system and methods for avoiding harm to neural tissue during surgery. According to a broad aspect, the present invention includes an instrument capable of advancement to a surgical target site and a processing system. The instrument is configured to deliver a stimulation signal either while advancing to the target site and after reaching said target site. The processing system is programmed with a set of at least three threshold ranges and configured to direct a first stimulation signal to said instrument at a first magnitude. The first magnitude corresponds to a boundary between the pair of ranges. The processing system further directs a second stimulation signal at a second magnitude corresponding to a boundary between a different pair of the ranges. The processing unit is still further programmed to and measure the response of nerves depolarized by said stimulation signals to indicate at least one of nerve proximity and pedicle integrity.

According to another broad aspect, the present invention includes a control unit, a patient module, and a plurality of surgical accessories adapted to couple to the patient module. The control unit includes a power supply and is programmed to receive user commands, activate stimulation in a plurality of predetermined modes, process signal data according to defined algorithms, display received parameters and processed data, and monitor system status. The patient module is in communication with the control unit. The patient module is within the sterile field. The patient module includes signal conditioning circuitry, stimulator drive circuitry, and signal conditioning circuitry required to perform said stimulation in said predetermined modes. The patient module includes a processor programmed to perform a plurality of predetermined functions including at least two of static pedicle integrity testing, dynamic pedicle integrity testing, nerve proximity detection, neuromuscular pathway assessment, manual motor evoked potential monitoring, automatic motor evoked potential monitoring, somatosensory evoked potential monitoring, non-evoked monitoring, and surgical navigation.

According to still another broad aspect, the present invention includes an instrument and a processing system. The instrument is in communication with the processing unit. The instrument is capable of advancement to a surgical target site and is configured to deliver a stimulation signal at least one of while advancing to said target site and after reaching said target site. The processing unit is programmed to perform a plurality of predetermined functions using said instrument including at least two of static pedicle integrity testing, dynamic pedicle integrity testing, nerve proximity detection, neuromuscular pathway assessment, manual motor evoked potential monitoring, automatic motor evoked potential monitoring, somatosensory evoked potential monitoring, non-evoked monitoring, and surgical navigation. The processing system has a pre-established profile for at least one of said predetermined functions so as to facilitate the initiation of said at least one predetermined function.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 6 is a perspective view of an example of a control unit forming part of the neurophysiology system of FIG. 1;

FIGS. 7-9 are perspective, top, and side views, respectively, of an example of a patient module forming part of the neurophysiology system of FIG. 1;

FIGS. 11A-11C are side views of various examples of harness ports forming part of the neurophysiology system of FIG. 1;

FIG. 12 is a plan view of an example of a label affixed to an electrode connector forming part of the neurophysiology system of FIG. 1;

FIGS. 13A-13B are top views of examples of electrode caps forming part of the neurophysiology system of FIG. 1;

FIG. 18 is side view of an example of a stimulation clip accessory forming part of the neurophysiology system of FIG. 1;

FIGS. 19-20 are perspective views of individual components of the stimulation clip of FIG. 18;

FIG. 35 are graphs illustrating use of the threshold hunting algorithm of FIG. 32 and further omitting stimulations when the likely result is already clear from previous data;

DETAILED DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination. It is also expressly noted that, although described herein largely in terms of use in spinal surgery, the surgical system and related methods described herein are suitable for use in any number of additional procedures, surgical or otherwise, wherein assessing the health of the spinal cord and/or various other nerve tissue may prove beneficial.

Figure 1:
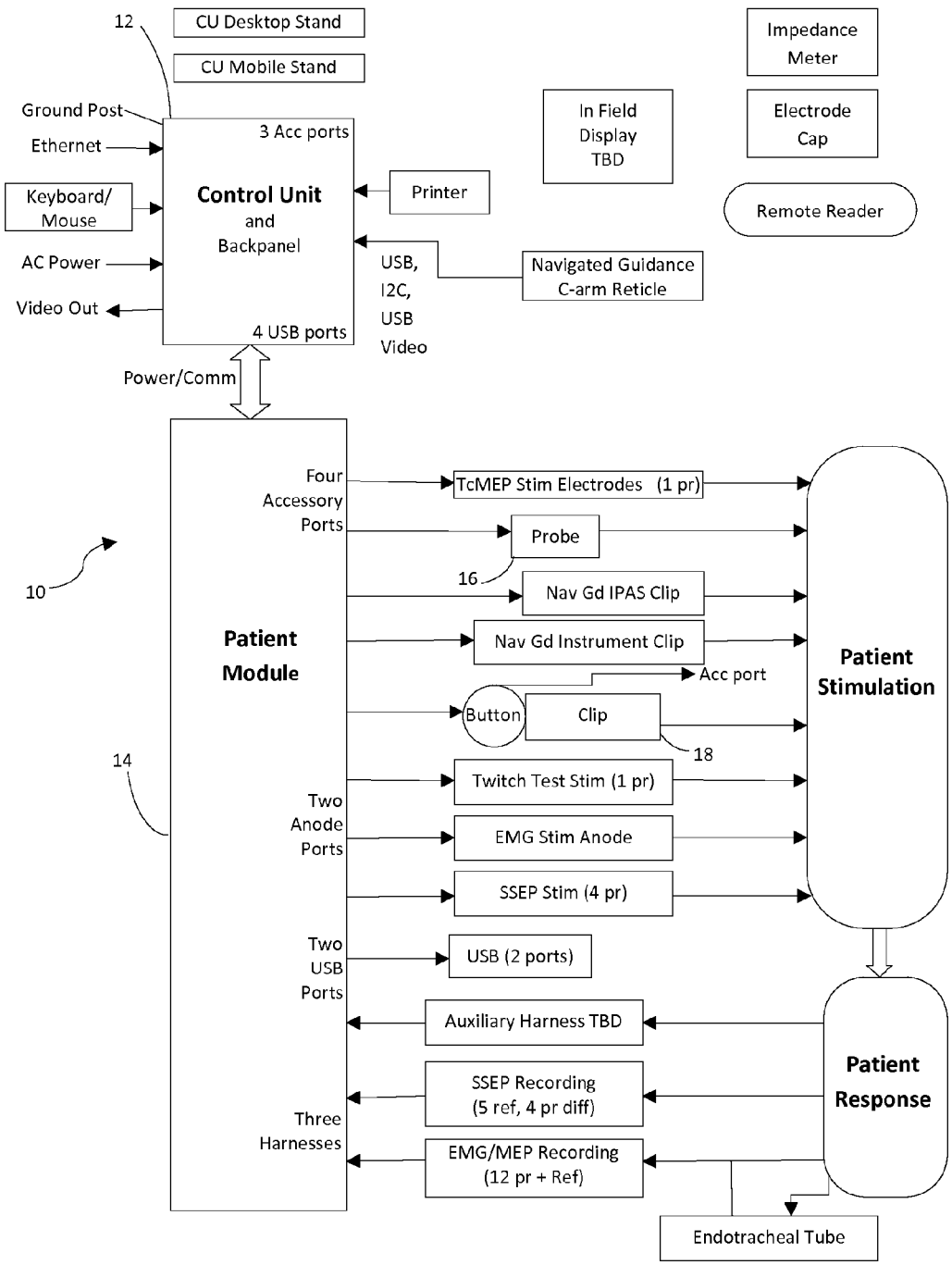
FIG. 1 is a block diagram of an exemplary surgical system capable of conducting multiple nerve and spinal cord monitoring functions including but not necessarily limited to MEP, SSEP, neuromuscular pathway, bone integrity, nerve detection, and nerve pathology (evoked or free-run EMG) assessments.
Figure 2:
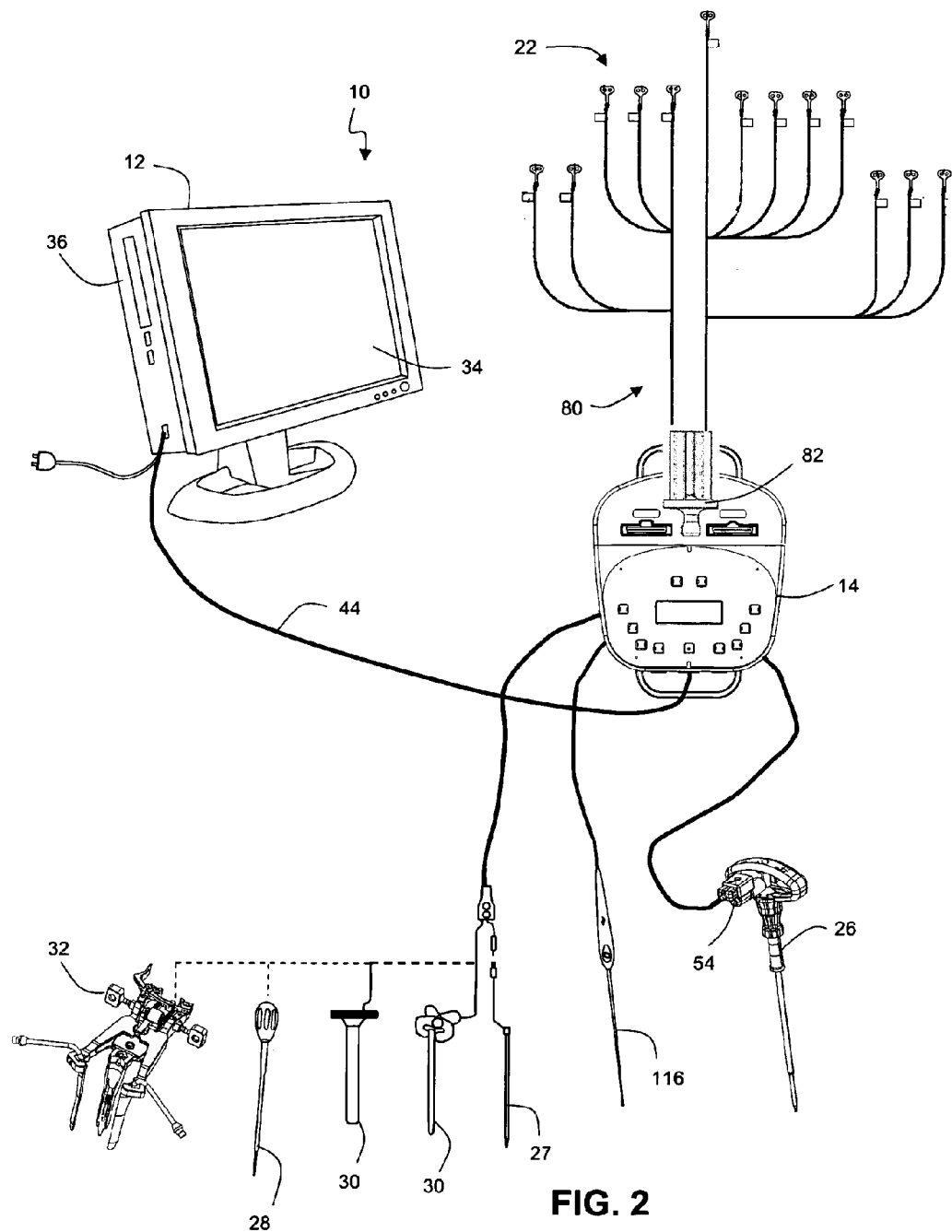
FIG. 2 is a perspective view of showing examples of several components of the neurophysiology system of FIG. 1.

A surgeon operable neurophysiology system 10 is described herein and is capable of performing a number of neurophysiological and/or guidance assessments at the direction of the surgeon (and/or other members of the surgical staff). By way of example only, FIGS. 1-2 illustrate the basic components of the neurophysiology system 10. The system comprises a control unit 12 (including a main display 34 preferably equipped with a graphical user interface (GUI) and a processing unit 22 that collectively contain the essential processing capabilities for controlling the system 10), a patient module 14, a stimulation accessory (e.g. a stimulation probe 16, stimulation clip 18 for connection to various surgical instruments, an inline stimulation hub 20, and stimulation electrodes 22), and a plurality of recording electrodes 24 for detecting electrical potentials. The stimulation clip 18 may be used to connect any of a variety of surgical instruments to the system 10, including, but not necessarily limited to a pedicle access needle 26, k-wire 27, tap 28, dilator(s) 30, tissue retractor 32, etc. One or more secondary feedback devices (e.g. secondary display 46) may also be provided for additional expression of output to a user and/or receiving input from the user.

In one embodiment, the neurophysiology system 10 may be configured to execute any of the functional modes including, but not necessarily limited to, static pedicle integrity testing ("Basic Stimulated EMG"), dynamic pedicle integrity testing ("Dynamic Stimulated EMG"), nerve proximity detection ("XLIF®"), neuromuscular pathway assessment ("Twitch Test"), motor evoked potential monitoring ("MEP manual" and MEP Automatic"), somatosensory evoked potential monitoring ("SSEP"), non-evoked monitoring ("Free-run EMG") and surgical navigation ("Navigated Guidance"). The neurophysiology system 10 may also be configured for performance in any of the lumbar, thoracolumbar, and cervical regions of the spine.

Figure 3:
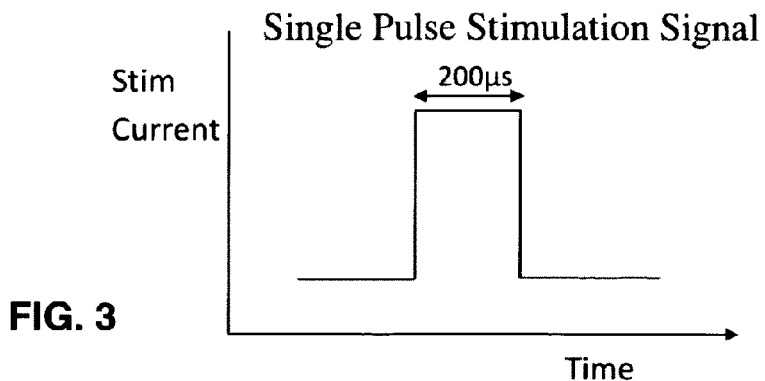
FIG. 3 is a graph illustrating a plot of a single pulse stimulation current signal capable of producing a neuromuscular response (EMG) of the type shown in FIG. 5.
Figure 4:
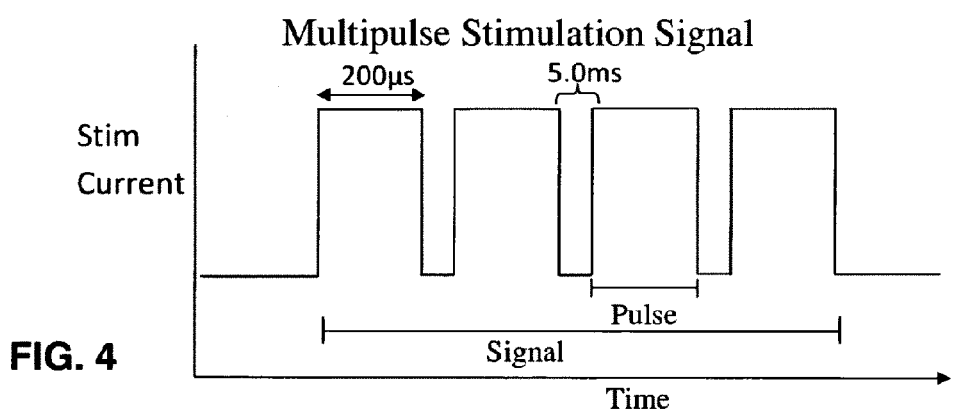
FIG. 4 is a graph illustrating a plot of a stimulation current signal comprising a train of pulses capable of producing a neuromuscular response (EMG) of the type shown in FIG. 5.
Figure 5:
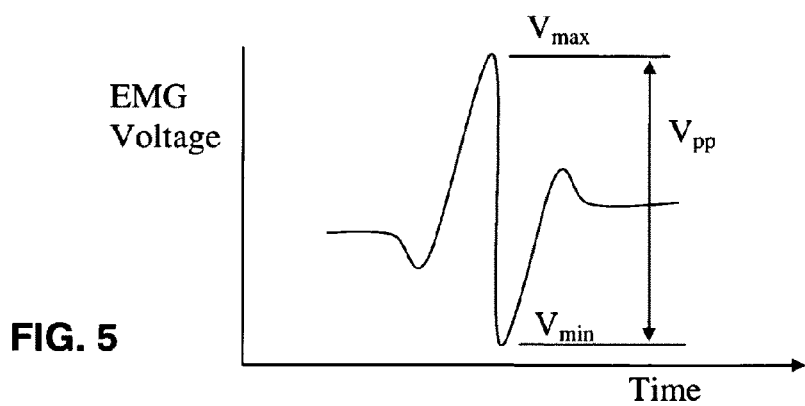
FIG. 5 is a graph illustrating a plot of the neuromuscular response (EMG) of a given myotome over time based on a stimulation signal (such as shown in either FIG. 3 or FIG. 4)

The basis for performing many of these functional modes (e.g. Basic Stimulated EMG, Dynamic Stimulated EMG, XLIF, MEP manual, and MEP automatic, and Twitch Test) is the assessment of evoked responses of the various muscles myotomes monitored by the system 10 in relation to a stimulation signal transmitted by the system 10 (via patient module 14). This is illustrated in FIG. 3-5, wherein FIG. 5 illustrates the resulting EMG waveform of a monitored myotome in response to one of the example stimulation signals represented in FIG. 3 and FIG. 4. The EMG responses provide a quantitative measure of the nerve depolarization caused by the electrical stimulus. One way to characterize the EMG response is by a peak-to-peak voltage of $V_{pp}=V_{max}-V_{min}$, as shown in FIG. 5. Nerve tissues have characteristic threshold current levels ($I_{thresh}$) at which they will depolarize and result in a detectable muscle activity. Below this threshold current level, a stimulation signal will not evoke a significant EMG response. According to one embodiment, a significant EMG response may be defined as having a $V_{pp}$ of approximately 100 uV. Thus, the lowest stimulation current necessary to evoke an EMG response of the threshold voltage ($V_{thresh}$), 100 uV in this example, may be called $I_{thresh}$. The greater the degree of electrical communication between a stimulation signal and a nerve, the lower $I_{thresh}$ will be. Conversely, the lower the degree of electrical communication between a stimulation signal and a nerve, the greater $I_{thresh}$ will be. Thus determining $I_{thresh}$, and/or monitoring changes in $I_{thresh}$ over time, may provide valuable information when nerve tissues are at risk during a surgical procedure, as will be discussed in more detail below. By way of example, an excessively high $I_{thresh}$ or an increase over a previous measurement during MEP may indicate a problem in the spinal cord inhibiting transmission (communication) of the stimulation signal to the nerve. Meanwhile, during the Basic Stimulated EMG or Dynamic Stimulated EMG modes and the XLIF mode, a low $I_{thresh}$ value may indicate a breach in the pedicle allowing the electrical signal to transmit through the pedicle, or the close proximity of a nerve to the stimulation source, respectively. Armed with the useful information conveyed by $I_{thresh}$, the surgeon may detect a problem or potential problem early and then act to avoid mitigate the problem The neurophysiology system 10 may quickly and accurately determine $I_{thresh}$ under the direction and operation of the surgeon (if desired) and convey the useful information $I_{thresh}$ contains in a simple and easily comprehensible manner for interpretation by the surgeon.

Before further addressing $I_{thresh}$ and the various functional modes of the surgical system 10, the hardware components and features of the system 10 will be describe in further detail. The control unit 12 of the neurophysiology system 10, illustrated by way of example only in FIG. 6, includes a main display 34 and a processing unit 36, which collectively contain the essential processing capabilities for controlling the neurophysiology system 10. The main display 34 is preferably equipped with a graphical user interface (GUI) capable of graphically communicating information to the user and receiving instructions from the user. The processing unit 36 contains computer hardware and software that commands the stimulation source (e.g. patient module 14, FIGS. 7-9), receives digital and/or analog signals and other information from the patient module 14, processes EMG and SSEP response signals, and displays the processed data to the operator via the display 34. The primary functions of the software within the control unit 12 include receiving user commands via the touch screen main display 34, activating stimulation in the appropriate mode (Basic Stimulated EMG, Dynamic Stimulated EMG, XLIF, MEP automatic, MEP manual, SSEP, and Twitch Test), processing signal data according to defined algorithms, displaying received parameters and processed data, and monitoring system status. According to one example embodiment, the main display 34 may comprise a 15" LCD display equipped with suitable touch screen technology and the processing unit 36 may comprise a 2 GHz. The processing unit 36 shown in FIG. 6 further includes a powered USB port 38 for connection to the patient module 14, a media drive 40 (e.g. CD, CD-RW, DVD, DVD-RW, etc . . . ), a network port, wireless network card, and a plurality of additional ports 42 (e.g. USB, IEEE 1394, infrared, etc . . . ) for attaching additional accessories, such as for example only, navigated guidance sensors, auxiliary stimulation anodes, and external devices (e.g. printer, keyboard, mouse, etc . . . ). Preferably, during use the control unit 12 sits near the surgical table but outside the surgical field, such as for example, on a table top or a mobile stand. It will be appreciated, however, that if properly draped and protected, the control unit 12 may be located within the surgical (sterile) field.

The patient module 14, shown by way of example only in FIGS. 7-9, is communicatively linked to the control unit 12. In this embodiment the patient module 14 is communicatively linked with and receives power from the control unit 12 via a USB data cable 44. However, it will be appreciated that the patient module 14 may be supplied with its own power source and other known data cables, as well as wireless technology, may be utilized to establish communication between the patient module 14 and control unit 12. The patient module 14 contains a digital communications interface to communicate with the control unit 12, as well as the electrical connections to all recording and stimulation electrodes, signal conditioning circuitry, stimulator drive and steering circuitry, and signal conditioning circuitry required to perform all of the functional modes of the neurophysiology system 10, including but not necessarily limited to Basic Stimulated EMG, Dynamic Stimulated EMG, XLIF, Twitch Test, MEP Manual and MEP Automatic, and SSEP. A display (e.g. an LCD screen) may be provided on the face of the patient module 14, and may be utilized for showing simple status readouts (for example, results of a power on test, the electrode harnesses attached, and impedance data, etc . . . ) or more procedure related data (for example, a stimulation threshold result, current stimulation level, selected function, etc . . . ). The patient module 14 may be positioned near the patient in the sterile field during surgery. By way of example, the patient module 14 may be attached to bed rail with the aid of a hook 48 attached to, or forming a part of, the patient module 14 casing.

With reference to FIGS. 7-9, patient module 14 comprises a multitude of ports and indicators for connecting and verifying connections between the patient module 14 and other system components. A control unit port 50 is provided for data and power communication with the control unit 12, via USB data cable 44 as previously described. There are four accessory ports 52 provided for connecting up to the same number of surgical accessories, including, but not necessarily limited to, stimulation probe 16, stimulation clip 18, inline stimulation hub 20, and navigated guidance sensor (or tilt sensor) 54. The accessory ports 52 include a stimulation cathode and transmit digital communication signals, tri-color LED drive signals, button status signals, identification signals, and power between the patient module 14 and the attached accessory. A pair of anode ports 56, preferably comprising 2 wire DIN connectors, may be used to attach auxiliary stimulation anodes should it become desirable or necessary to do so during a procedure. A pair of USB ports 58 are connected as a USB hub to the control unit 12 and may be used to make any number of connections, such as for example only, a portable storage drive.

As soon as a device is plugged into any one of ports 50, 52, 56, or 58, the neurophysiology system 10 automatically performs a circuit continuity check to ensure the associated device will work properly. Each device forms a separate closed circuit with the patient module such that the devices may be checked independent of each other. If one device is not working properly the device may be identified individually while the remaining devices continue indicate their valid status. An indicator LED is provided for each port to convey the results of the continuity check to the user. Thus, according to the example embodiment of FIGS. 7-9, the patient module 14 includes one control unit indicator 60, four accessory indicators 62, two anode indicators 64, and two USB indicators 66. According to a preferred embodiment, if the system detects an incomplete circuit during the continuity check, the appropriate indicator will turn red alerting the user that the device might not work properly. On the other hand, if a complete circuit is detected, the indicator will appear green signifying that the device should work as desired. Additional indicator LEDs are provided to indicate the status of the system and the MEP stimulation. The system indicator 68 will appear green when the system is ready and red when the system is not ready. The MEP stim indicator 70 lights up when the patient module is ready to deliver and MEP stimulation signal. In one embodiment, the MEP stim indicator 68 appears yellow to indicate a ready status.

To connect the array of recording electrodes 24 and stimulation electrodes 22 utilized by the system 10, the patient module 14 also includes a plurality of electrode harness ports. In the embodiment shown, the patient module 14 includes an EMG/MEP harness port 72, SSEP harness port 74, and an Auxiliary harness port 76 (for expansion and/or custom harnesses). Each harness port 72, 74, and 76 includes a shaped socket 78 that corresponds to a matching shaped connector 82 on the appropriate electrode harness 80. In addition, the neurophysiology system 10 may preferably employ a color code system wherein each modality (e.g. EMG, EMG/MEP, and SSEP) has a unique color associated with it. By way of example only and as shown herein, EMG monitoring (including, screw tests, detection, and nerve retractor) may be associated with the color green, MEP monitoring with the color blue, and SSEP monitoring may be associated with the color orange. Thus, each harness port 72, 74, 76 is marked with the appropriate color which will also correspond to the appropriate harness 80. Utilizing the combination of the dedicated color code and the shaped socket/connector interface simplifies the setup of the system, reduces errors, and can greatly minimize the amount of pre-operative preparation necessary. The patient module 14, and especially the configuration of quantity and layout of the various ports and indicators, has been described according to one example embodiment of the present invention. It should be appreciated, however, that the patient module 14 could be configured with any number of different arrangements without departing from the scope of the invention.

Figure 10:
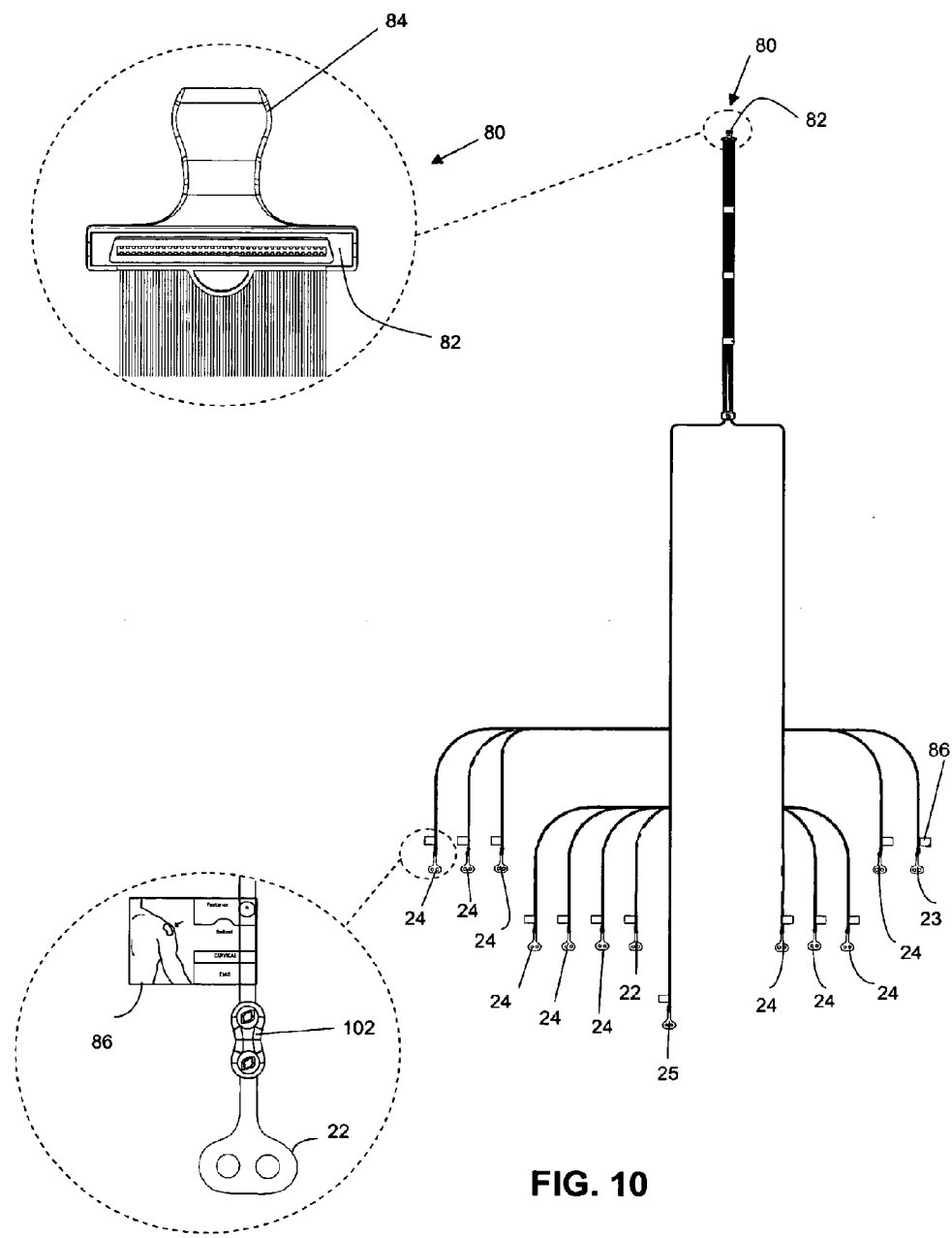
FIG. 10 is a top view of an electrode harness 80 forming part of the neurophysiology system of FIG. 1.

As mentioned above, to simplify setup of the system 10, all of the recording electrodes 24 and stimulation electrodes 22 that are required to perform one of the various functional modes (including a common electrode 23 providing a ground reference to pre-amplifiers in the patient module 14, and an anode electrode 25 providing a return path for the stimulation current) are bundled together and provided in single electrode harness 80, as illustrated, by way of example only, in FIG. 10. Depending on the desired function or functions to be used during a particular procedure, different groupings of recoding electrodes 24 and stimulation electrodes 22 may be required. By way of example, the SSEP function requires more stimulating electrodes 22 than either the EMG or MEP functions, but also requires fewer recording electrodes than either of the EMG and MEP functions. To account for the differing electrode needs of the various functional modes, the neurophysiology system 10 may employ different harnesses 80 tailored for the desired modes. According to one embodiment, three different electrode harnesses 80 may be provided for use with the system 10, an EMG harness, an EMG/MEP harness, and an SSEP harness.

At one end of the harness 80 is the shaped connector 82. As described above, the shaped connector 82 interfaces with the shaped socket 72, 74, or 76 (depending on the functions harness 80 is provided for). Each harness 80 utilizes a shaped connector 82 that corresponds to the appropriate shaped socket 72, 74, 76 on the patient module 14. If the shapes of the socket and connector do not match the harness 80, connection to the patient module 14 cannot be established. According to one embodiment, the EMG and the EMG/MEP harnesses both plug into the EMG/MEP harness port 72 and thus they both utilized the same shaped connector 82. By way of example only, FIGS. 11A-11C illustrate the various shape profiles used by the different harness ports 72, 74, 76 and connectors 82. FIG. 11A illustrates the half circular shape associated with the EMG and EMG/MEP harness and port 72. FIG. 11B illustrates the rectangular shape utilized by the SSEP harness and port 74. Finally, FIG. 11C illustrates the triangular shape utilized by the Auxiliary harness and port 76. Each harness connector 82 includes a digital identification signal that identifies the type of harness 80 to the patient module 14. At the opposite end of the electrode harness 80 are a plurality of electrode connectors 102 linked to the harness connector 82 via a wire lead. Using the electrode connector 102, any of a variety of known electrodes may be used, such as by way of example only, surface dry gel electrodes, surface wet gel electrodes, and needle electrodes.

To facilitate easy placement of scalp electrodes used during MEP and SSEP modes, an electrode cap 81, depicted by way of example only in FIG. 13A may be used. The electrode cap 81 includes two recording electrodes 23 for SSEP monitoring, two stimulation electrodes 22 for MEP stimulation delivery, and an anode 23. Graphic indicators may be used on the electrode cap 81 to delineate the different electrodes. By way of example, lightning bolts may be used to indicate a stimulation electrode, a circle within a circle may be used to indicate recording electrodes, and a stepped arrow may be used to indicate the anode electrode. The anode electrode wire is colored white to further distinguish it from the other electrodes and is significantly longer that the other electrode wires to allow placement of the anode electrode on the patient's shoulder. The shape of the electrode cap 81 may also be designed to simplify placement. By way of example only, the cap 81 has a pointed end that may point directly toward the patient's nose when the cap 81 is centered on the head in the right orientation. A single wire may connect the electrode cap 81 to the patient module 14 or electrode harness 80, thereby decreasing the wire population around the upper regions of the patient. Alternatively, the cap 81 may be equipped with a power supply and a wireless antenna for communicating with the system 10. FIG. 13B illustrates another example embodiment of an electrode cap 83 similar to cap 81. Rather than using graphic indicators to differentiate the electrodes, colored wires may be employed. By way of example, the stimulation electrodes 22 are colored yellow, the recording electrodes 24 are gray, and the anode electrode 23 is white. The anode electrode is seen here configured for placement on the patient's forehead.

To further simplify the process of placing the required electrodes, the end of each wire lead next to the electrode connector 102 may be tagged with a label 86 that shows or describes the proper positioning of the electrode on the patient. The label 86 preferably demonstrates proper electrode placement graphically and textually. As shown in FIG. 12, the label may include, a graphic image showing the relevant body portion 88 and the precise electrode position 90. Textually, the label 86 may indicate the side 100 and muscle (or anatomic location) 96 for placement, the function of the electrode (e.g. stimulation, recording channel, anode, and reference—not shown), the patient surface (e.g. anterior or posterior), the spinal region 94, and the type of monitoring 92 (e.g. EMG, MEP, SSEP, by way of example, only). According to one embodiment (set forth by way of example only), the electrode harnesses 80 are designed such that the various electrodes may be positioned about the patient (and preferably labeled accordingly) as described in Table 1 for Lumbar EMG, Table 2 for Cervical EMG, Table 3 for Lumbar/Thoracolumbar EMG and MEP, Table 4 for Cervical EMG and MEP, and Table 5 for SSEP:

TABLE 1

Lumbar EMG

| Electrode Type | Electrode Placement | Spinal Level |
| --- | --- | --- |
| Ground | Upper Outer Thigh | — |
| Anode | Latissimus Dorsi | — |
| Stimulation | Knee | — |
| Recording | Left Tibialis Anterior | L4, L5 |
| Recording | Left Gastroc. Medialis | S1, S2 |
| Recording | Left Vastus Medialis | L2, L3, L4 |
| Recording | Left Biceps Femoris | L5, S1, S2 |

TABLE 1-continued

Lumbar EMG

| Electrode Type | Electrode Placement | Spinal Level |
| --- | --- | --- |
| Recording | Right Biceps Femoris | L5, S1, S2 |
| Recording | Right Vastus Medialis | L2, L3, L4 |
| Recording | Right Gastroc. Medialis | S1, S2 |
| Recording | Right Tibialis Anterior | L4, L5 |

TABLE 2

Cervical EMG

| Electrode Type | Electrode Placement | Spinal Level |
| --- | --- | --- |
| Ground | Shoulder | — |
| Anode | Mastoid | — |
| Stimulation | Inside Elbow | — |
| Recording | Left Triceps | C7, C8 |
| Recording | Left Flexor Carpi Radialis | C6, C7, C8 |
| Recording | Left Deltoid | C5, C6 |
| Recording | Left Trapezius | C3, C4 |
| Recording | Left Vocal Cord | RLN |
| Recording | Right Vocal Cord | RLN |
| Recording | Right Trapezius | C3, C4 |
| Recording | Right Deltoid | C5, C6 |
| Recording | Right Flexor Carpi Radialis | C6, C7, C8 |
| Recording | Right Triceps | C7, C8 |

TABLE 3

Lumbar/Thoracolumbar EMG + MEP

| Electrode Type | Electrode Placement | Spinal Level |
| --- | --- | --- |
| Ground | Upper Outer Thigh | — |
| Anode | Latissimus Dorsi | — |
| Stimulation | Knee | — |
| Recording | Left Tibialis Anterior | L4, L5 |
| Recording | Left Gastroc. Medialis | S1, S2 |
| Recording | Left Vastus Medialis | L2, L3, L4 |
| Recording | Left Biceps Femoris | L5, S1, S2 |
| Recording | Left APB-ADM | C6, C7, C8, T1 |
| Recording | Right APB-ADM | C6, C7, C8, T1 |
| Recording | Right Biceps Femoris | L5, S1, S2 |
| Recording | Right Vastus Medialis | L2, L3, L4 |
| Recording | Right Gastroc. Medialis | S1, S2 |
| Recording | Right Tibialis Anterior | L4, L5 |

TABLE 4

Cervical EMG + MEP

| Electrode Type | Electrode Placement | Spinal Level |
| --- | --- | --- |
| Ground | Shoulder | — |
| Anode | Mastoid | — |
| Stimulation | Inside Elbow | — |
| Recording | Left Tibialis Anterior | L4, L5 |
| Recording | Left Flexor Carpi Radialis | C6, C7, C8 |
| Recording | Left Deltoid | C5, C6 |
| Recording | Left Trapezius | C3, C4 |
| Recording | Left APB-ADM | C6, C7, C8, T1 |
| Recording | Left Vocal Cord | RLN |
| Recording | Right Vocal Cord | RLN |
| Recording | Right APB-ADM | C6, C7, C8, T1 |
| Recording | Right Trapezius | C3, C4 |
| Recording | Right Deltoid | C5, C6 |
| Recording | Right Flexor Carpi Radialis | C6, C7, C8 |
| Recording | Right Tibialis Anterior | L4, L5 |

TABLE 5

| SSEP | | |
| --- | --- | --- |
| Electrode Type | Electrode Placement | Spinal Level |
| Ground | Shoulder | — |
| Stimulation | Left Post Tibial Nerve | — |
| Stimulation | Left Ulnar Nerve | — |
| Stimulation | Right Post Tibial Nerve | — |
| Stimulation | Right Ulnar Nerve | — |
| Recording | Left Popliteal Fossa | — |
| Recording | Left Erb's | — |
| Recording | Left Scalp Cp3 | — |
| Recording | Right Popliteal Fossa | — |
| Recording | Right Erb's | — |
| Recording | Right Scalp Cp4 | — |
| Recording | Center ScalpFpz | — |
| Recording | Center Scalp Cz | — |
| Recording | Center Cervical Spine | — |

Figure 14A:
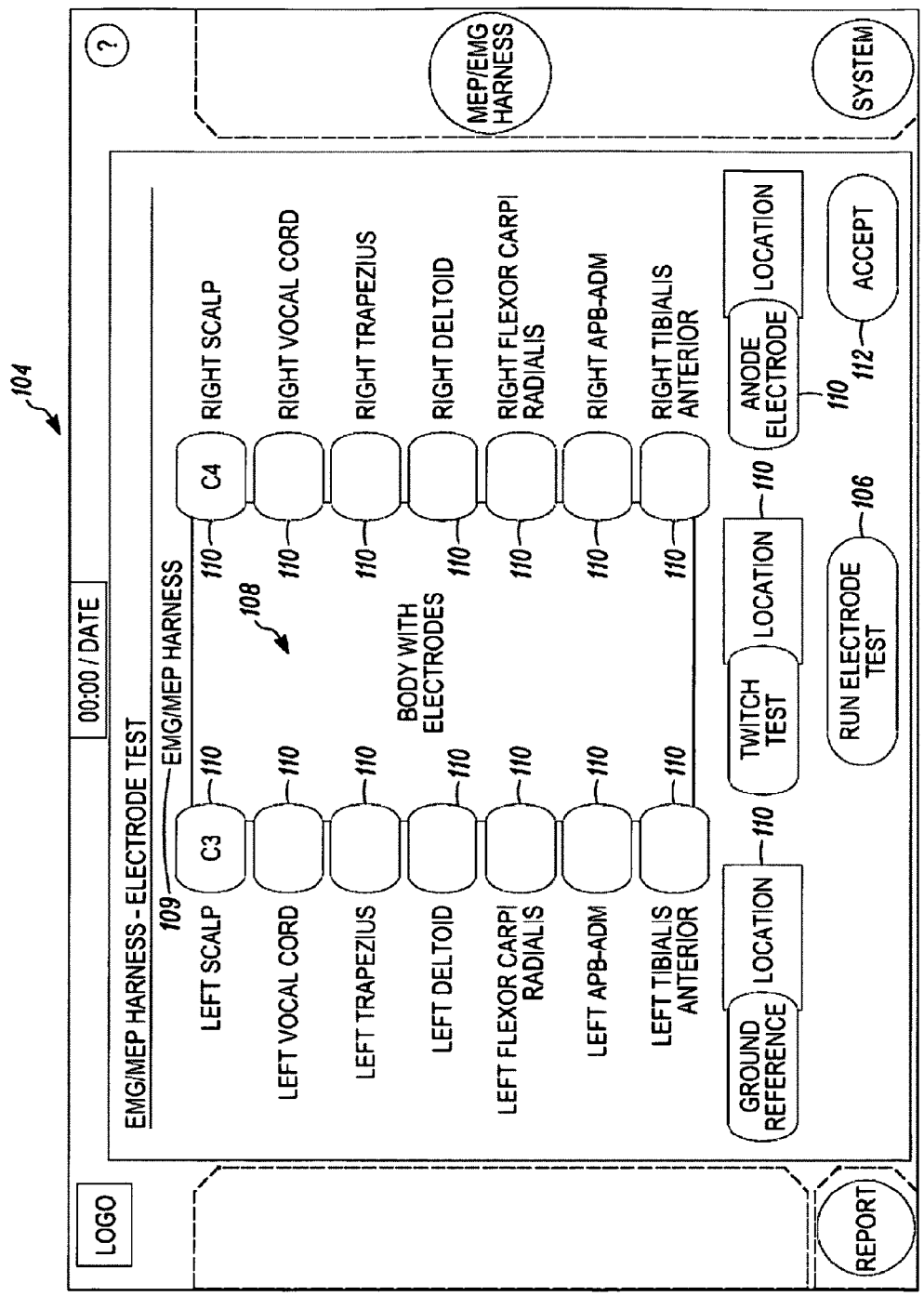
FIG. 14A is a block diagram setting forth the features of an electrode test as implemented on an electrode test screen forming part of the neurophysiology system of FIG. 1.
Figure 14B:
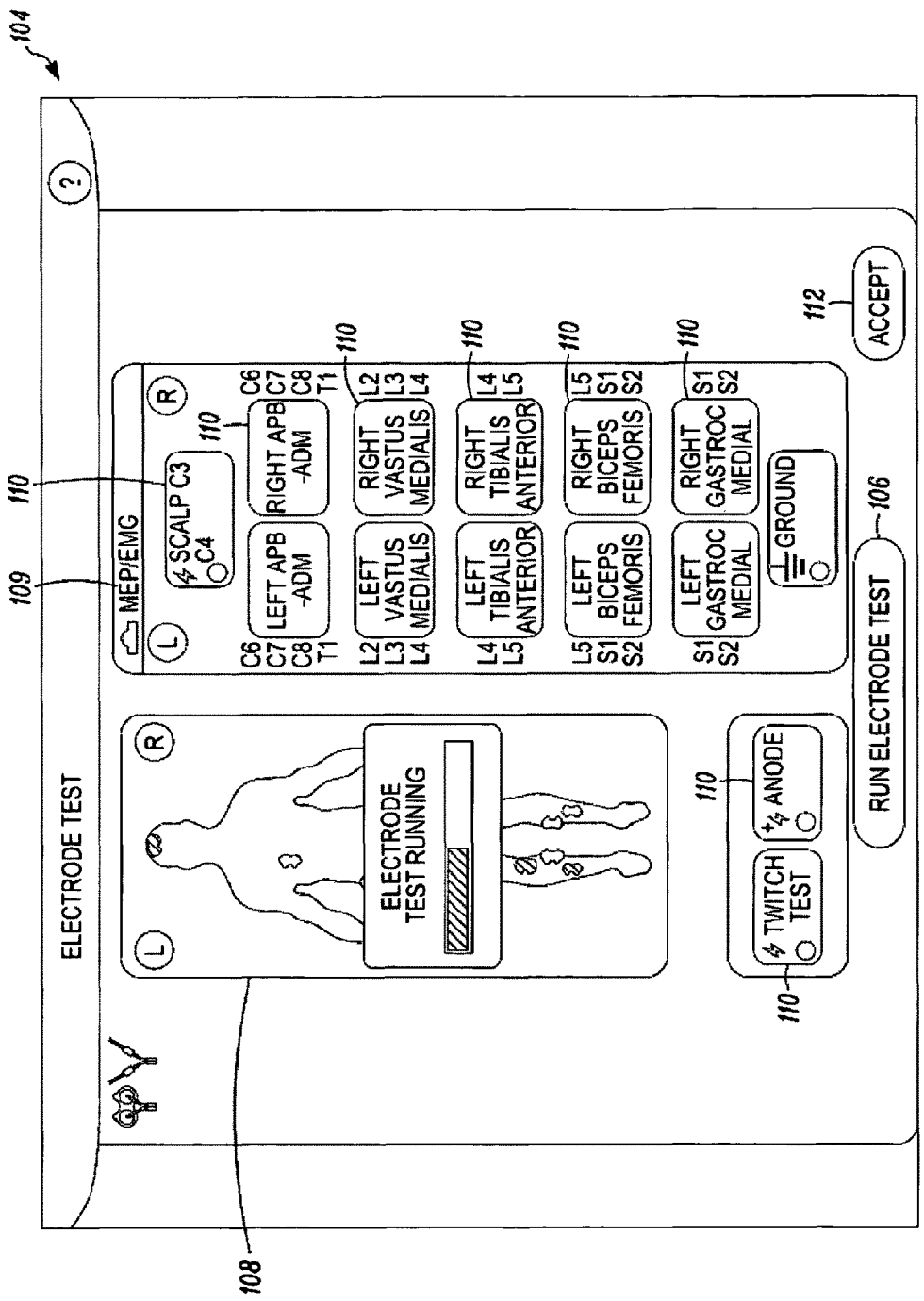
FIG. 14B is a screenshot capturing the features of FIG. 14A.

The patient module 14 is configured such that the neurophysiology system 10 may conduct an impedance test under the direction of the control unit 12 of all electrodes once the system is set up and the electrode harness is connected and applied to the patient. After choosing the appropriate spinal site upon program startup (described below), the user is directed to an electrode test. FIG. 14A illustrates, by way of example only, a box diagram setting forth the features of the electrode test as implemented on an electrode test screen 104. FIG. 14B illustrates, by way of example only, a graphical implementation capturing the features described in FIG. 14A, according to one example embodiment of the GUI. The electrode test screen 104 includes a human figure depiction with positioned electrodes 108. A harness indicator 109 displays which harness is in use. For each electrode on the harness 80 in use there is a channel button 110. This includes the common 25 and anode 23 electrods which are both independently checked for impedance. To accomplish this, the anode 23 and common 25 are both provided as dual electrodes. At least one of the anode leads on the anode electrode is reversible. During the impedance check the reversible anode lead switches to a cathode such that the impedance between the leads can be measured. When the impedance test is complete the reversible lead switches back to an anode. The channel button 110 may be labeled with the muscle or coverage area of the corresponding electrode. Selecting the channel button 110 will disable the channel. Disabled channels will not be tested for impedance and they will not be monitored for responses or errors unless reactivated. Upon selection of a start button 106 (entitled "Run Electrode Test"), the system 10 tests each electrode individually to determine the impedance value. If the impedance is determined to be within acceptable limits, the channel button 110 and electrode depiction on the human FIG. 108 turn green. If the impedance value for any electrode is not determined to be acceptable, the associated channel button 110 and electrode depiction turn red, alerting the user. Once the test is complete, selecting the Accept button 112 will open the main monitoring screen of system 10. In order to individually check the impedance of the both the anode electrode 25 and common electrode 23 may be individually tested for impedance.

Figure 15:
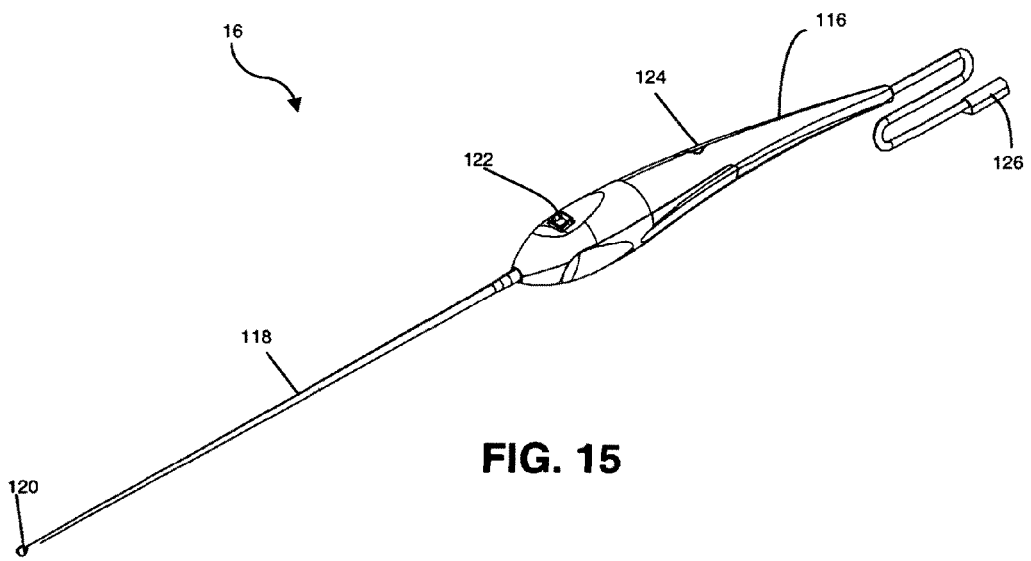
FIGS. 15-17 are perspective, top, and side views, respectively, of an example of a stimulation probe accessory forming part of the neurophysiology system of FIG. 1.
Figure 16:
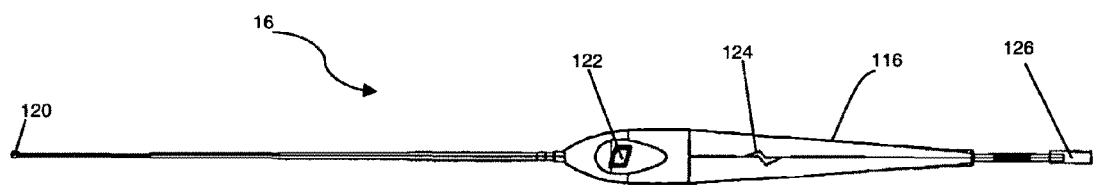
Figure 17:
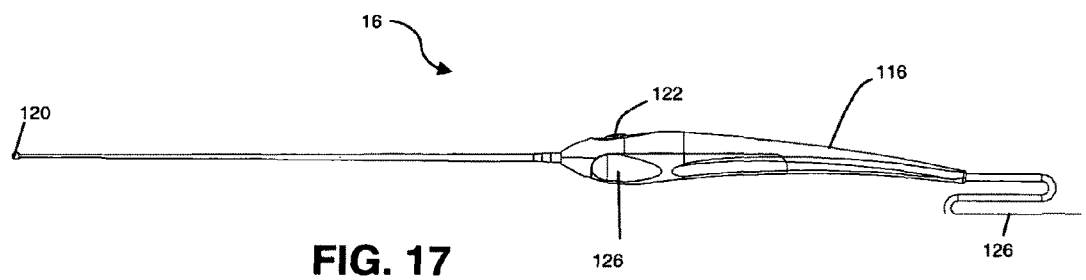

The neurophysiology system 10 may utilize various stimulation accessories to deliver stimulation signals to a stimulation target site, such as a hole formed or being formed in a pedicle and/or tissue surrounding a surgical access corridor. One such stimulation accessory is the stimulation probe 16, illustrated, by way of example, in FIGS. 15-17. The probe 16 includes an ergonomic handle 116 and an insulated probe member 118 with an uninsulated ball end 120. Preferably, the entire stimulation probe 16 is disposable and a new probe may be provided for each use. The handle 116 includes an integrated stimulation button 122. Depressing the stimulation button 122 while active in an appropriate functional mode (e.g. Basic Stimulated EMG) is effective to activate stimulation in the selected functional mode. The finger indentions 126 and curved under surface 128 permit the probe 16 to rest comfortably in the hands of the user.

Also situated in the handle 116 of probe 16 is a multi-color LED light 124. The LED 124 may be used to indicate the connectivity status of the probe. This may be done preferably, in addition to the connectivity status indicated from the accessory indicator 62. When the probe 16 is connected to the patient module 14 stimulation is active the LED 124 may appear predetermined color (e.g. purple in this embodiment) to indicate the stimulation status. Additionally, the LED 124 may be used to indicate the status of a threshold ($I_{thresh}$) result. By way of example, and as will be further described below, if a threshold value is determined to be within a predetermined safe range, the probe LED 124 may appear the color green indicating relative safety. If the determined threshold value falls within a predetermined unsafe range, the probe LED 124 may appear the color red indicating potential danger. Finally, if the threshold result is between the predetermined safe and unsafe ranges, the probe LED may appear yellow indicating caution. The probe handle 116 may also be equipped to emit audible tones related to the determined threshold results. For example, the pitch of the sound may change in response to different threshold levels. Thus, when a determined threshold is in the safe (Green) range then a low pitch tone may be emitted. When the threshold result is in-between the safe and unsafe levels (Yellow) the sound may have a higher pitch. A still higher pitch may be emitted when the threshold result is in the unsafe (Red) range. Alternatively, a different sound volume may indicate different safety levels. In still another alternative, different sounds (e.g. ping, bell, siren etc . . . ) may be produced for each safety level. The probe handle 116 may also be equipped to deliver tactile feedback to the user. For example, the probe handle 116 may vibrate in response to a determined stimulation threshold. The vibration of the probe 116 may operate in similar fashion to that of the sound function just described. That is, the vibration frequency and/or intensity may be altered depending on the safety level of the corresponding threshold result. Any of the vibration frequency, intensity, pulse pattern, etc . . . may be variable depending upon the stimulation result so as to provide an indication to the user of the determined threshold. The stimulation probe 116 includes a connector 126 that may be plugged into one of the accessory ports 62 on the patient module 14. Similar to the electrode connector 82, the probe connector 126 includes an identification signal that identifies the probe 116 to the patient module 14.

FIGS. 18-20 illustrate an example embodiment of another stimulation accessory, this one in the form of a stimulation clip 18 that permits the system 10 to deliver stimulation signals through various surgical instruments already used during the surgical procedure. By way of example only, the coupling device 18 may connect the neurophysiology system 10 with instruments including, but not necessarily limited to a pedicle access needle 26, a tap 28, dilator 30, tissue retractor 32, and k-wire 27. The stimulation clip 18 utilizes a spring-loaded plunger 128 to hold the surgical tool and transmit the stimulation signal thereto. The plunger 128 is composed of a conductive material such as metal. A nonconductive housing 130 partially encases the plunger 128 about its center. Extending from the housing 130 is an end plate 132 that hooks the surgical instrument. A spring (not shown) is disposed within the housing 130 such that in a natural or "closed" state the plunger 128 is situated in close proximity to the endplate 132. Exerting a compressive force on the spring (such as by pulling on the thumb grip 134) causes a gap between the end plate 132 and the plunger 128 to widen to an "open" position (shown in FIGS. 18-19), thereby allowing insertion of a surgical tool between the end plate 132 and plunger128. Releasing the thumb grip 134 allows the spring to return to a "closed" position, causing the plunger 132 to move laterally back towards the endplate such that a force is exerted upon the surgical instrument and thereby holding it in place between the endplate 132 and the plunger 128. The clip 18 further includes a button module 129 containing an activation button 131 for initiating stimulation. The button module 129 is set apart from the body of the clip 18 and they are linked by an integrated wire. An accessory port 133 is located next to the button 131 on the button module 129, thus minimizing the number of wires connecting back to the patient module 14 and outside the sterile field. Clip 18 is equipped with three LEDs 135, 137, and 139. LED 135 is associated with the accessory port 133 and LED 137 is associated with the clip 18 to indicate which of the two is stimulating. The LEDs 135 and 137 may appear purple when stimulation is active. When a stimulation result is determined the associated LED 135 or 137 may appear either red (if the result meets a predetermined potentially unsafe value), green (if the result meets a predetermined safe value), or yellow (if the result is in between the safe and potentially unsafe values). A third LED 139 is contained within the thumb grip 134, which will appear red, yellow, or green depending on the threshold result. The clip 18 connects to one of the accessory ports 62 on the patient module 14 via a connector 136. The connector 136 includes an identification signal that identifies it to the patient module 14.

Figure 21:
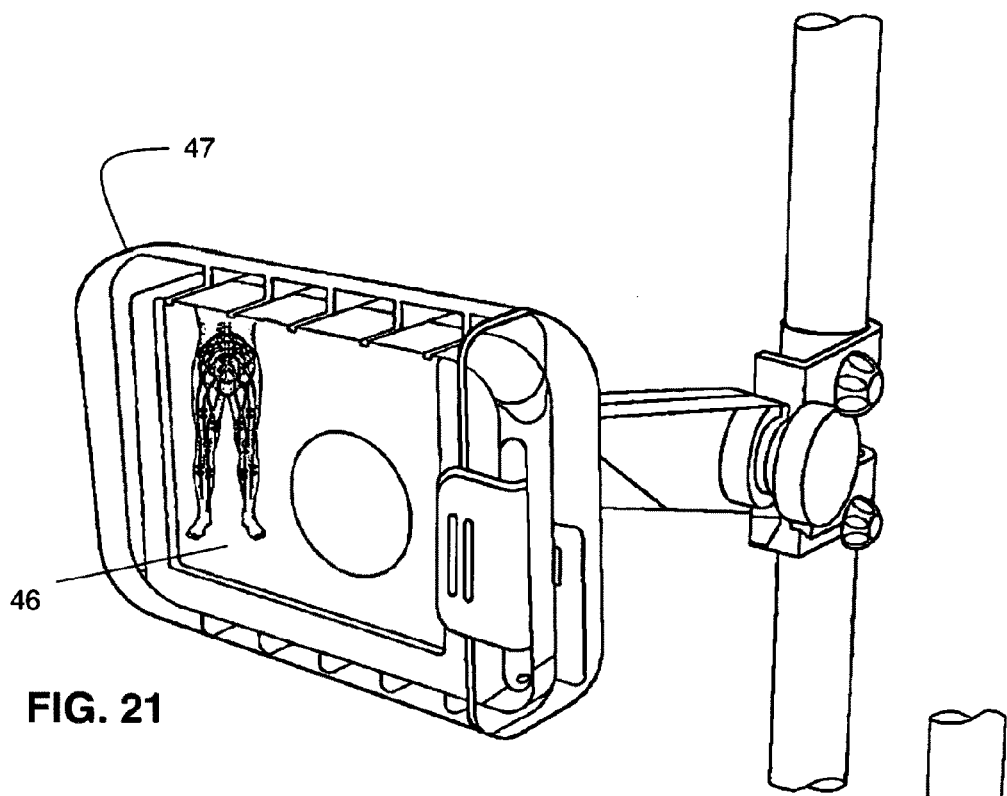
FIGS. 21-22 are perspective views of an example of a secondary display forming part of the neurophysiology system of FIG. 1.
Figure 22:
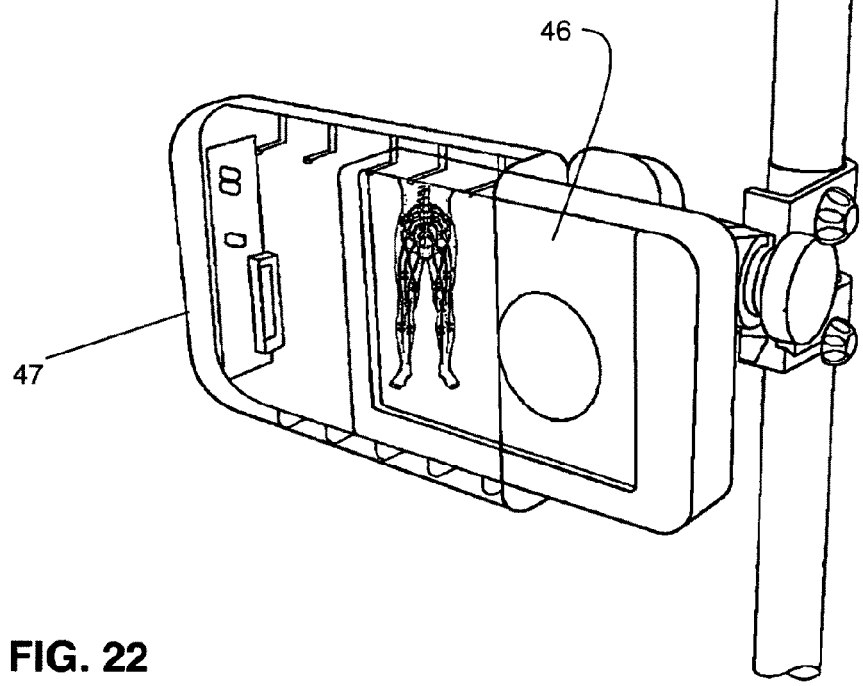

As mentioned above, the neurophysiology monitoring system 10 may include a secondary display, such as for example only, the secondary display 46 illustrated in FIGS. 21-22. The secondary display 46 may be configured to display some or all of the information provided on main display 34. The information displayed to the user on the secondary display 34 may include, but is not necessarily limited to, alpha-numeric and/or graphical information regarding any of the selected function modes (e.g. Basic Stimulated EMG, Dynamic Stimulated EMG, XLIF, MEP automatic, MEP manual, SSEP, and Twitch Test, and Free run), attached accessories (e.g. stimulation probe 16, stimulation clip 18, tilt sensor 54), electrode harness or harnesses attached, impedance test results, myotome/EMG levels, stimulation levels, history reports, selected parameters, test results, etc . . . . In one embodiment, secondary display 46 may be configured to receive user input in addition to its display function. The secondary display 46 can thus be used as an alternate control point for the system 10. The control unit 12 and secondary display 46 may be linked such that input may be received on from one display without changing the output shown on the other display. This would allow the surgeon to maintain focus on the patient and test results while still allowing other members of the OR staff to manipulate the system 10 for various purposes (e.g. inputting annotations, viewing history, etc . . . ). The secondary display 46 may be battery powered. Advantageously, the secondary display 46 may be positioned inside the sterile field as well as outside the sterile field. For positioning within the sterile field a disposable sterile case 47 may be provided to house the display. Alternatively, the display 46 may be sterile bagged. Both the sterile case 47 and the secondary display 46 may be mounted to a pole, bed frame, light fixture, or other apparatus found near and/or in the surgical field. It is further contemplated that multiple secondary displays 46 may be linked to the control unit 12. This may effectively distribute neurophysiology information and control throughout the operating room. By way of example, a secondary display 46 may also be provided for the anesthesiologist. This may be particularly useful in providing the anesthesiologist with results from the Twitch Test and providing reminders about the use of paralytics, which may adversely affect the accuracy of the neurophysiology system 10. Wired or wireless technology may be utilized to link the secondary display 46 to the control unit 12.

Figure 23A:
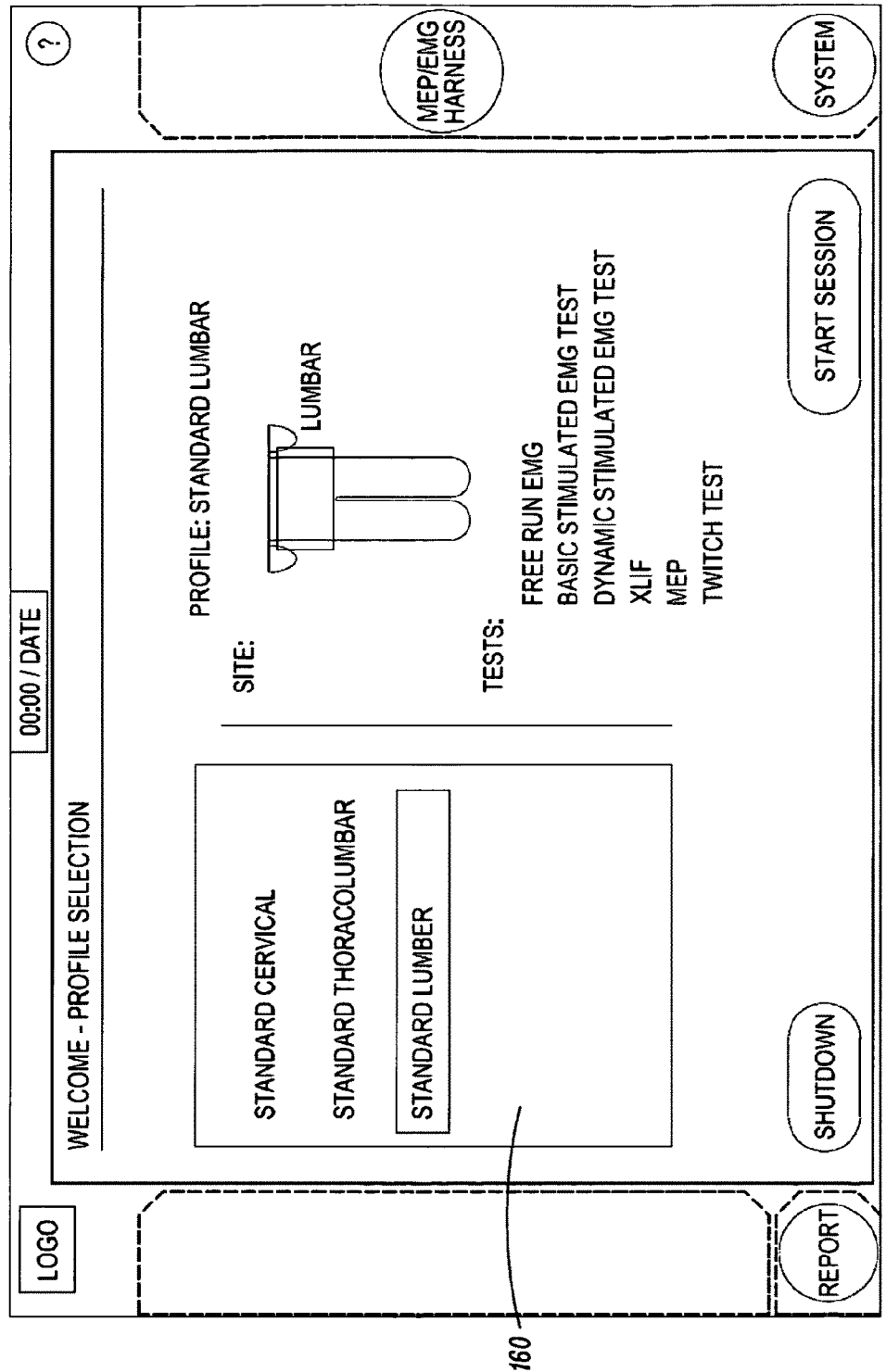
FIG. 23A-23B are a block diagram and screenshot, respectively, of an example of a startup screen forming part of the neurophysiology system of FIG. 1.
Figure 23B:
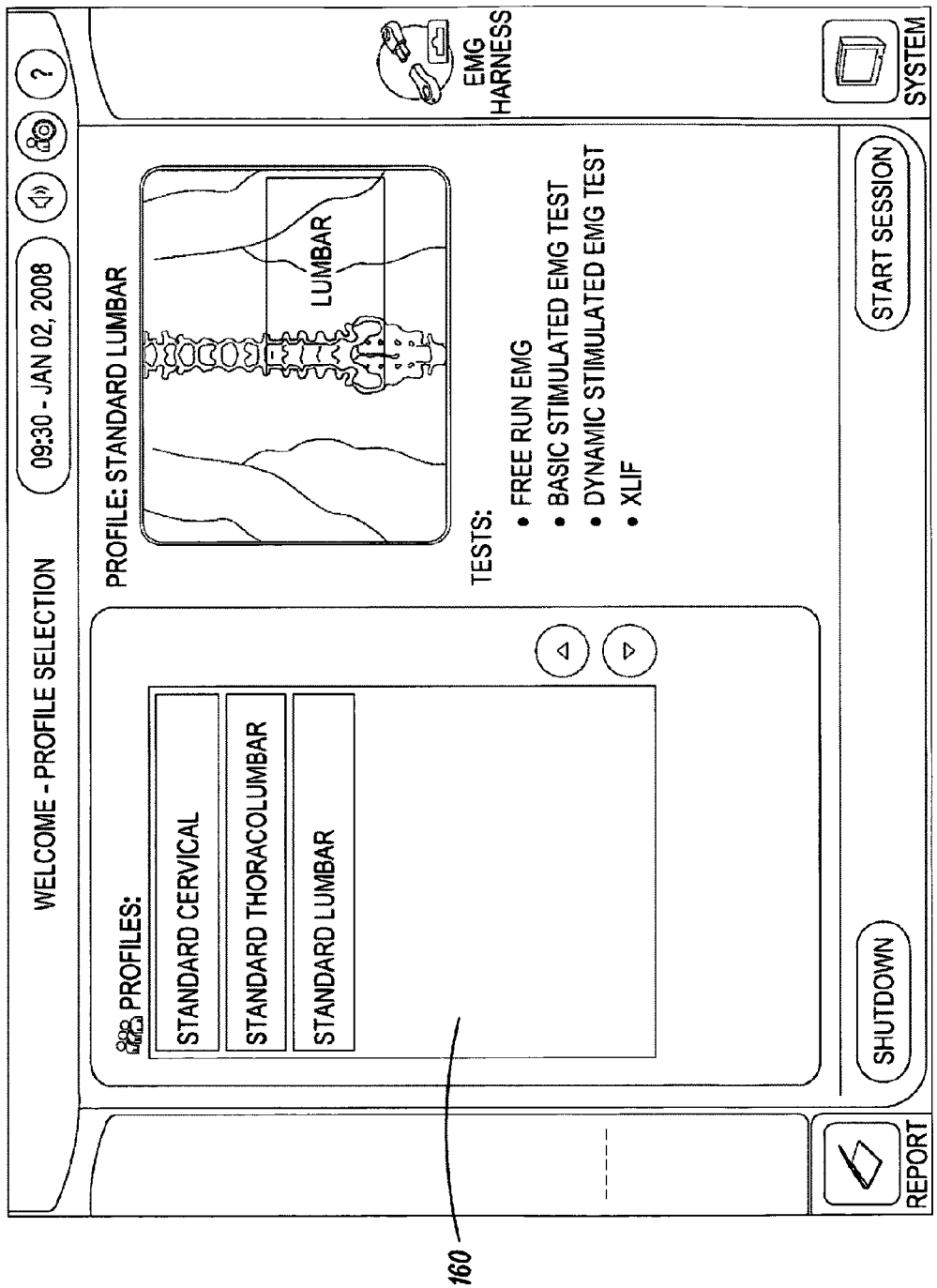

Having described an example embodiment of the system 10 and the hardware components that comprise it, the neurophysiological functionality and methodology of the system 10 will now be described in further detail. Various parameters and configurations of the neuromonitoring system 10 may depend upon the target location, i.e. spinal region, of the surgical procedure. In one embodiment, upon starting the system 10 the software will automatically open to the startup screen, illustrated by way of example only, in block chart form in FIG. 23A and graphical form in FIG. 23B. The startup screen includes a profile selection window 160 from which the user may select from one of the standard profiles (e.g. "Standard Cervical," "Standard Thoracolumbar," and "Standard Lumbar") or any custom profiles that have been previously saved to the system. Selecting a profile configures the system 10 to the parameters assigned for the selected region or to custom parameters saved under the profile. The availability of different function modes depends upon the profile selected. By way of example only, selecting the cervical and thoracolumbar spinal regions may automatically configure the options to allow selection of the Twitch Test, Basic and Dynamic Stimulated EMG Tests, MEP Auto, MEP Manual, SSEP, and Navigated Guidance modes, while selecting the lumbar region may automatically configure the options to allow selection of the Twitch Test, Basic and Dynamic Stimulated EMG Tests, XLIF®, and Nerve Retractor modes. Default parameters associated with the various function modes may also depend on the profile selected; for example, the characteristics of the stimulation signal delivered by the system 10 may vary depending on the profile. By way of example, the stimulation signal utilized for the Stimulated EMG modes may be configured differently when a lumbar profile is selected versus when one of a thoracolumbar profile and a cervical profile. As previously described above, each of the hardware components includes an identification tag that allows the control unit 12 to know exactly what devices are hooked up and ready for operation. In one embodiment, profiles may only be available for selection if the appropriate devices (e.g. proper electrode harness 80 and stimulation accessories) are connected and/or ready for operation. Alternatively, the software could bypass the startup screen and jump straight to one of the functional modes based on the accessories and/or harnesses it knows are plugged in. The ability to select a profile based on standard parameters, and especially on customized preferences, may save significant time at the beginning of a procedure and provides for monitoring availability right from the start. Moving on from the startup screen, the software advances directly to an electrode test screen and impedance tests, which are performed on every electrode as discussed above. When an acceptable impedance test has been completed, the system 10 is ready to begin monitoring and the software advances to a monitoring screen from which the neurophysiological monitoring functions of the system 10 are performed.

The information displayed on the monitoring screen may include, but is not necessarily limited to, alpha-numeric and/or graphical information regarding any of the functional modes (e.g., Basic Stimulated EMG, Dynamic Stimulated EMG, XLIF, MEP automatic, MEP manual, SSEP, Twitch Test, and Free run), attached accessories (e.g. stimulation probe 16, stimulation clip 18, tilt sensor 54), electrode harness or harnesses attached, impedance test results, myotome/EMG levels, stimulation levels, history reports, selected parameters, test results, etc . . . . In one embodiment, set forth by way of example only, this information displayed on a main monitoring screen may include, but is not necessarily limited to the following components as set forth in Table 6:

TABLE 6

| Screen Component | Description |
| --- | --- |
| Patient Image/ Electrode layout | An image of the human body or relevant portion thereof showing the electrode placement on the body, with labeled channel number tabs on each side (1-4 on the left and right). Left and right labels will show the patient orientation. The channel number tabs may be highlighted or colored depending on the specific function being performed. |
| Myotome & Level Names | A label to indicate the Myotome name and corresponding Spinal Level(s) associated with the channel of interest. |
| Test Menu | A hideable menu bar for selecting between the available functional modes. |
| Device Bar | A hideable bar displaying icons and/or names of devices connected to the patient module. |
| Display Area | Shows procedure-specific information including stimulation results. |
| Color Indication | Enhances stimulation results with a color display of green, yellow, or red corresponding to the relative safety level determined by the system. |
| Stimulation Bar | A graphical stimulation indicator depicting the present stimulation status (i.e. on or off and stimulation current level), as well as providing for starting and stopping stimulation |
| Event Bar | A hideable bar that shows the last up to a selected number of previous stimulation results, provides for annotation of results, and a chat dialogue box for communicating with remote participants. |
| EMG waveforms | EMG waveforms may be optionally displayed on screen along with the stimulation results. |

Figure 24A:
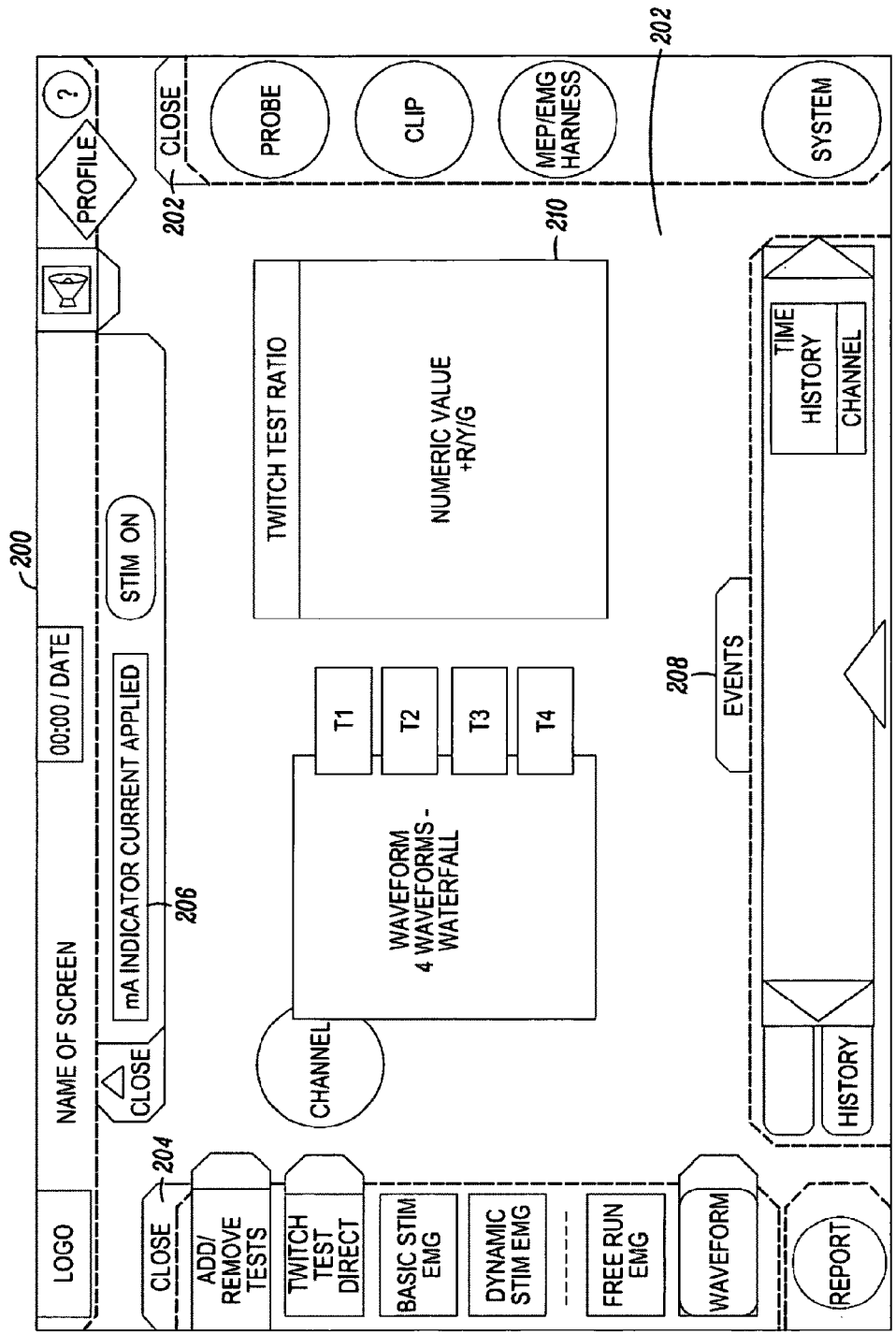
FIG. 24A-24B are a block diagram and screenshot, respectively, of an example of a monitoring screen forming part of the neurophysiology system of FIG. 1.
Figure 24B:
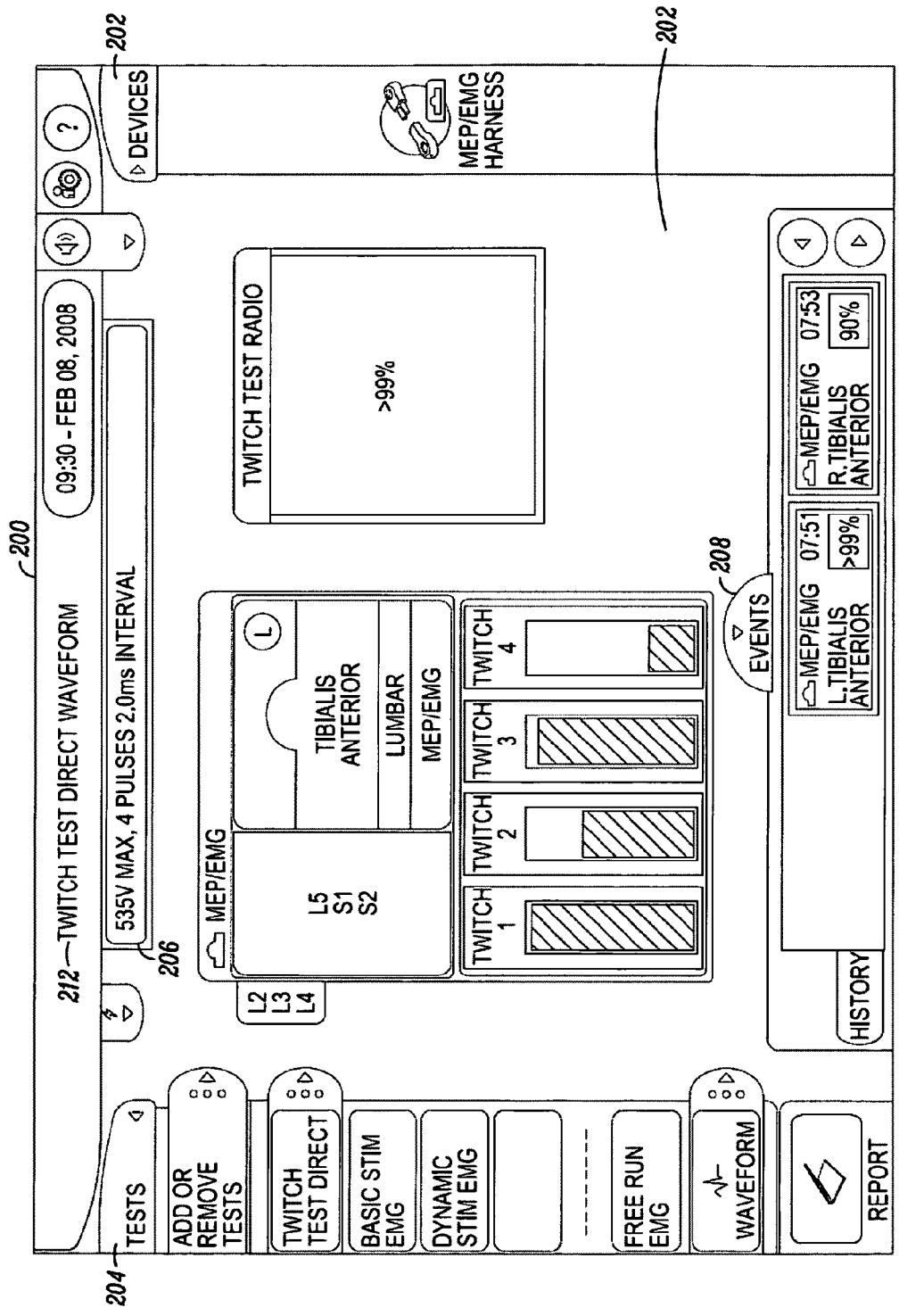

With reference to FIGS. 24A-24B, various features of the monitoring screen 200 of the GUI will now be described. It should be appreciated that while FIGS. 24A-24B depict the monitoring screen 200 while the selected function is the Twitch Test, the features of monitoring screen 200 apply equally to all the functions. Result-specific data is displayed in a center result area 202. A large color saturated numeric value 210 is use to show the threshold result. Three different options are provided for showing the stimulation response level. First, the user can view the waveform. Second, a likeness of the color coded electrode harness label 86 may be shown on the display. Third, the color coded label 212 may be integrated with a body image. On one side of center result area 202 there is a collapsible device menu 202. The device menu displays a graphic representation of each device connected to the patient module 14. If a device is selected from the device menu 202, an impedance test may be initiated. Opposite the device menu 202 there is a collapsible test menu 204. The test menu 204 highlights each test that is available under the operable setup profile and may be used to navigate between functions. A collapsible stimulation bar 206 indicates the current stimulation status and provides start and stop stimulation buttons (not shown) to activate and control stimulation. The collapsible event bar 208 stores all the stimulation test results obtained throughout a procedure so that the user may review the entire case history from the monitoring screen. Clicking on a particular event will open a note box and annotations may be entered and saved with the response, for later inclusion in a procedure report chronicling all nerve monitoring functions conducted during the procedure as well as the results of nerve monitoring. In one embodiment the report may be printed immediately from one or more printers located in the operating room or copied to any of a variety of memory devices known in the prior art, such as, by way of example only, a floppy disk, and/or USB memory stick. The system 10 may generate either a full report or a summary report depending on the particular needs of the user. In one embodiment, the identifiers used to identify the surgical accessories to the patient module may also be encoded to identify their lot number or other identifying information. As soon as the accessory is identified, the lot number may be automatically added to the report. Alternatively, hand held scanners can be provided and linked to the control unit 12 or patient module 14. The accessory packaging may be scanned and again the information may go directly to the procedure report. The event bar 208 also houses a chat box feature when the system 10 is connected to a remote monitoring system to allow a user in the operating room to contemporaneously communicate with a person performing the associated neuromonitoring in a remote location.

Figure 37:
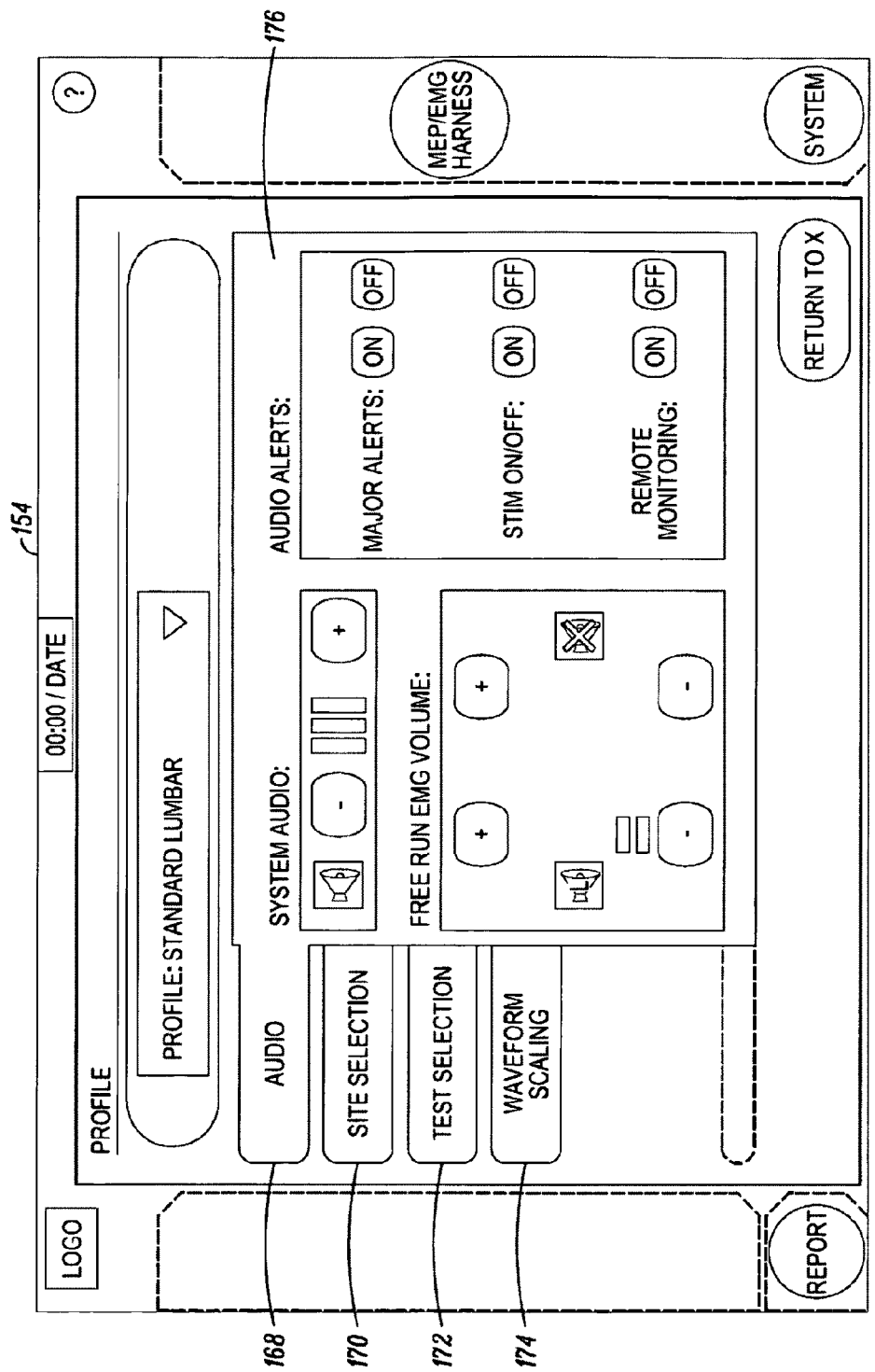
FIG. 37 is a block diagram of a profile setting screenshot forming part of the neurophysiology monitoring system of FIG. 1.

From a profile setting screen 154, illustrated by way of example only in FIG. 37, custom profiles can be created and saved. Beginning with one of the standard profiles, parameters may be altered by selecting one of the audio 168, site selection 170, test selection 172, and waveform scaling 174 buttons and making the changes until the desired parameters are set. By way of example only, profiles may be generated and saved for particular procedures (e.g. ACDF, XLIF, and Decompression) or for particular individuals. Clicking on each button will display the parameter options specific to the selected button in a parameter window 176. By way of example only, by selecting the audio button 168 both the system audio and Free Run audio may be adjusted. Selecting the site selection button 170 allows the opportunity to change from the site selected initially. Adjusting the site selection of the profile may alter the options available. By way of example, if the user changes the site selection from cervical to lumbar, the MEP function may no longer be selectable as an option. From within the test selection area, function specific parameters for all available test functions (based on site selection, available devices, etc . . . ) may be accessed and set according to need. One option that is available for multiple functions under the test selection button is the ability to select from three different viewing options. The user may choose to see results displayed in numeric form, on a body panel, and on a label that reflects the labels associated with each electrode, or any combination of the three. The user may also choose to see the actual waveforms. Selecting the waveform scaling button 174 allows the user to adjust the scale on which waveforms are displayed. Profiles may be saved directly on the control unit 12 or they may be saved to a portable memory device.

The functions performed by the neuromonitoring system 10 may include, but are not necessarily limited to, the Twitch Test, Free-run EMG, Basic Stimulated EMG, Dynamic Stimulated EMG, XLIF®, Nerve Retractor, MEP Auto, MEP manual, and SSEP modes, all of which will be described briefly below. The system 10 further includes a navigated guidance function that will also be described below. The Twitch Test mode is designed to assess the neuromuscular pathway via the so-called "train-of-four test" to ensure the neuromuscular pathway is free from muscle relaxants prior to performing neurophysiology-based testing, such as bone integrity (e.g. pedicle) testing, nerve detection, and nerve retraction. This is described in greater detail within PCT Patent App. No. PCT/US2005/036089, entitled "System and Methods for Assessing the Neuromuscular Pathway Prior to Nerve Testing," filed Oct. 7, 2005, the entire contents of which is hereby incorporated by reference as if set forth fully herein. The Basic Stimulated EMG Dynamic Stimulated EMG tests are designed to assess the integrity of bone (e.g. pedicle) during all aspects of pilot hole formation (e.g., via an awl), pilot hole preparation (e.g. via a tap), and screw introduction (during and after). These modes are described in greater detail in PCT Patent App. No. PCT/US02/35047 entitled "System and Methods for Performing Percutaneous Pedicle Integrity Assessments," filed on Oct. 30, 2002, and PCT Patent App. No. PCT/US2004/025550, entitled "System and Methods for Performing Dynamic Pedicle Integrity Assessments," filed on Aug. 5, 2004 the entire contents of which are both hereby incorporated by reference as if set forth fully herein. The XLIF mode is designed to detect the presence of nerves during the use of the various surgical access instruments of the neuromonitoring system 10, including the pedicle access needle 26, k-wire 42, dilator 44, and retractor assembly 70. This mode is described in greater detail within PCT Patent App. No. PCT/US2002/22247, entitled "System and Methods for Determining Nerve Proximity, Direction, and Pathology During Surgery," filed on Jul. 11, 2002, the entire contents of which is hereby incorporated by reference as if set forth fully herein. The Nerve Retractor mode is designed to assess the health or pathology of a nerve before, during, and after retraction of the nerve during a surgical procedure. This mode is described in greater detail within PCT Patent App. No. PCT/US2002/30617, entitled "System and Methods for Performing Surgical Procedures and Assessments," filed on Sep. 25, 2002, the entire contents of which are hereby incorporated by reference as if set forth fully herein. The MEP Auto and MEP Manual modes are designed to test the motor pathway to detect potential damage to the spinal cord by stimulating the motor cortex in the brain and recording the resulting EMG response of various muscles in the upper and lower extremities. The SSEP function is designed to test the sensory pathway to detect potential damage to the spinal cord by stimulating peripheral nerves inferior to the target spinal level and recording the action potential from sensors superior to the spinal level. The MEP Auto, MEP manual, and SSEP modes are described in greater detail within PCT Patent App. No. PCT/US2006/003966, entitled "System and Methods for Performing Neurophysiologic Assessments During Spine Surgery," filed on Feb. 2, 2006, the entire contents of which is hereby incorporated by reference as if set forth fully herein. The Navigated Guidance function is designed to facilitate the safe and reproducible use of surgical instruments and/or implants by providing the ability to determine the optimal or desired trajectory for surgical instruments and/or implants and monitor the trajectory of surgical instruments and/or implants during surgery. This mode is described in greater detail within PCT Patent App. No. PCT/US2007/11962, entitled "Surgical Trajectory Monitoring System and Related Methods," filed on Jul. 30, 2007, the entire contents of which are incorporated herein by reference as if set forth fully herein. These functions will be explained now in brief detail.

The neuromonitoring system 10 performs neuromuscular pathway (NMP) assessments, via Twitch Test mode, by electrically stimulating a peripheral nerve (preferably the Peroneal Nerve for lumbar and thoracolumbar applications and the Median Nerve for cervical applications) via stimulation electrodes 22 contained in the applicable electrode harness and placed on the skin over the nerve or by direct stimulation of a spinal nerve using a surgical accessory such as the probe 116. Evoked responses from the muscles innervated by the stimulated nerve are detected and recorded, the results of which are analyzed and a relationship between at least two responses or a stimulation signal and a response is identified. The identified relationship provides an indication of the current state of the NMP. The identified relationship may include, but is not necessarily limited to, one or more of magnitude ratios between multiple evoked responses and the presence or absence of an evoked response relative to a given stimulation signal or signals. With reference to FIGS. 24A-24B details of the test indicating the state of the NMP and the relative safety of continuing on with nerve testing are conveyed to the surgeon via GUI display 34. On the monitoring screen 200 utilized by the various functions performed by the system 10, function specific data is displayed in a center result area 202. The results may be shown as a numeric value 210, a highlighted label corresponding to the electrode labels 86, or (in the case of twitch test only) a bar graph of the stimulation results. On one side of center result area 202 is a collapsible device menu 202. The device menu displays a graphic representation of each device connected to the patient module 14. Opposite the device menu 202 there is a collapsible test menu 204. The test menu 204 highlights each test that is available under the operable setup profile and may be used to navigate between functions. A collapsible stimulation bar 206 indicates the current stimulation status and provides start and stop stimulation buttons (not shown) to activate and control stimulation. The collapsible event bar 208 stores all the stimulation test results obtained throughout a procedure. Clicking on a particular event will open a note box and annotations may be entered and saved with the response, for later inclusion in a procedure report. The event bar 208 also houses a chat box feature when the system 10 is connected to a remote monitoring system as described above. Within the result area 202 the twitch test specific results may be displayed.

The neuromonitoring system 10 may test the integrity of pedicle holes (during and/or after formation) and/or screws (during and/or after introduction) via the Basic Stimulation EMG and Dynamic Stimulation EMG tests. To perform the Basic Stimulation EMG a test probe 116 is placed in the screw hole prior to screw insertion or placed on the installed screw head and a stimulation signal is applied. The insulating character of bone will prevent the stimulation current, up to a certain amplitude, from communicating with the nerve, thus resulting in a relatively high $I_{thresh}$, as determined via the basic threshold hunting algorithm described below. However, in the event the pedicle wall has been breached by the screw or tap, the current density in the breach area will increase to the point that the stimulation current will pass through to the adjacent nerve roots and they will depolarize at a lower stimulation current, thus $I_{thresh}$ will be relatively low. The system described herein may exploit this knowledge to inform the practitioner of the current $I_{thresh}$ of the tested screw to determine if the pilot hole or screw has breached the pedicle wall.

In Dynamic Stim EMG mode, test probe 116 may be replaced with a clip 18 which may be utilized to couple a surgical tool, such as for example, a tap member 28 or a pedicle access needle 26, to the neuromonitoring system 10. In this manner, a stimulation signal may be passed through the surgical tool and pedicle integrity testing can be performed while the tool is in use. Thus, testing may be performed during pilot hole formation by coupling the access needle 26 to the neuromonitoring system 10, and during pilot hole preparation by coupling the tap 28 to the system 10. Likewise, by coupling a pedicle screw to the neuromonitoring system 10 (such as via pedicle screw instrumentation), integrity testing may be performed during screw introduction.

In both Basic Stimulation EMG mode and Dynamic Stimulation EMG mode, the signal characteristics used for testing in the lumbar testing may not be effective when monitoring in the thoracic and/or cervical levels because of the proximity of the spinal cord to thoracic and cervical pedicles. Whereas a breach formed in a pedicle of the lumbar spine results in stimulation being applied to a nerve root, a breach in a thoracic or cervical pedicle may result in stimulation of the spinal cord instead, but the spinal cord may not respond to a stimulation signal the same way the nerve root would. To account for this, the surgical system 10 is equipped to deliver stimulation signals having different characteristics based on the region selected. By way of example only, when the lumbar region is selected, stimulation signals for the stimulated EMG modes comprise single pulse signals (see FIG. 3). On the other hand, when the thoracic and cervical regions are selected the stimulation signals may be configured as multipulse signals (see FIG. 4).

Figure 25A:
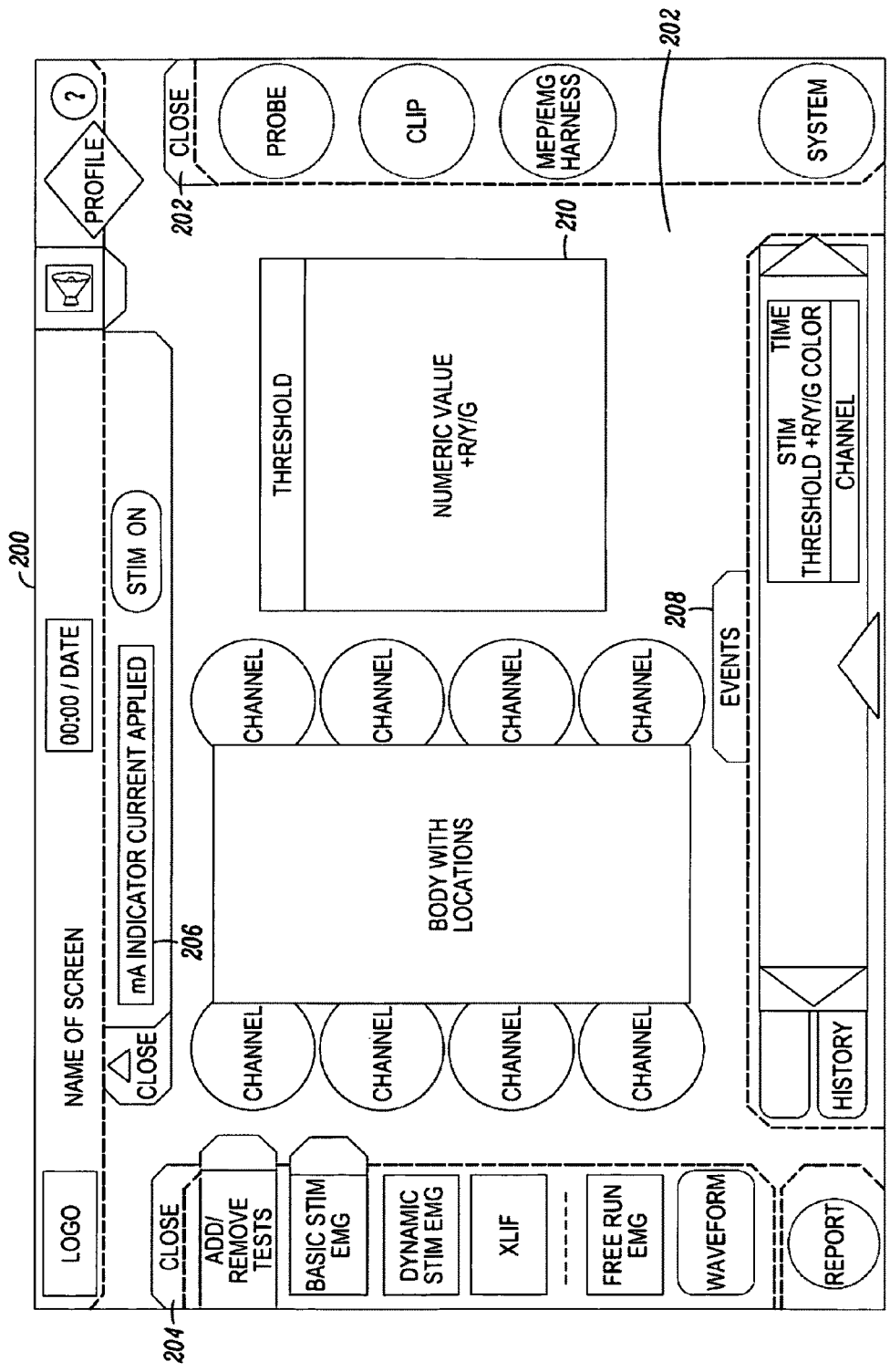
FIG. 25A-25B are a block diagram and screenshot, respectively, of a second example of a monitoring screen forming part of the neurophysiology system of FIG. 1.
Figure 25B:
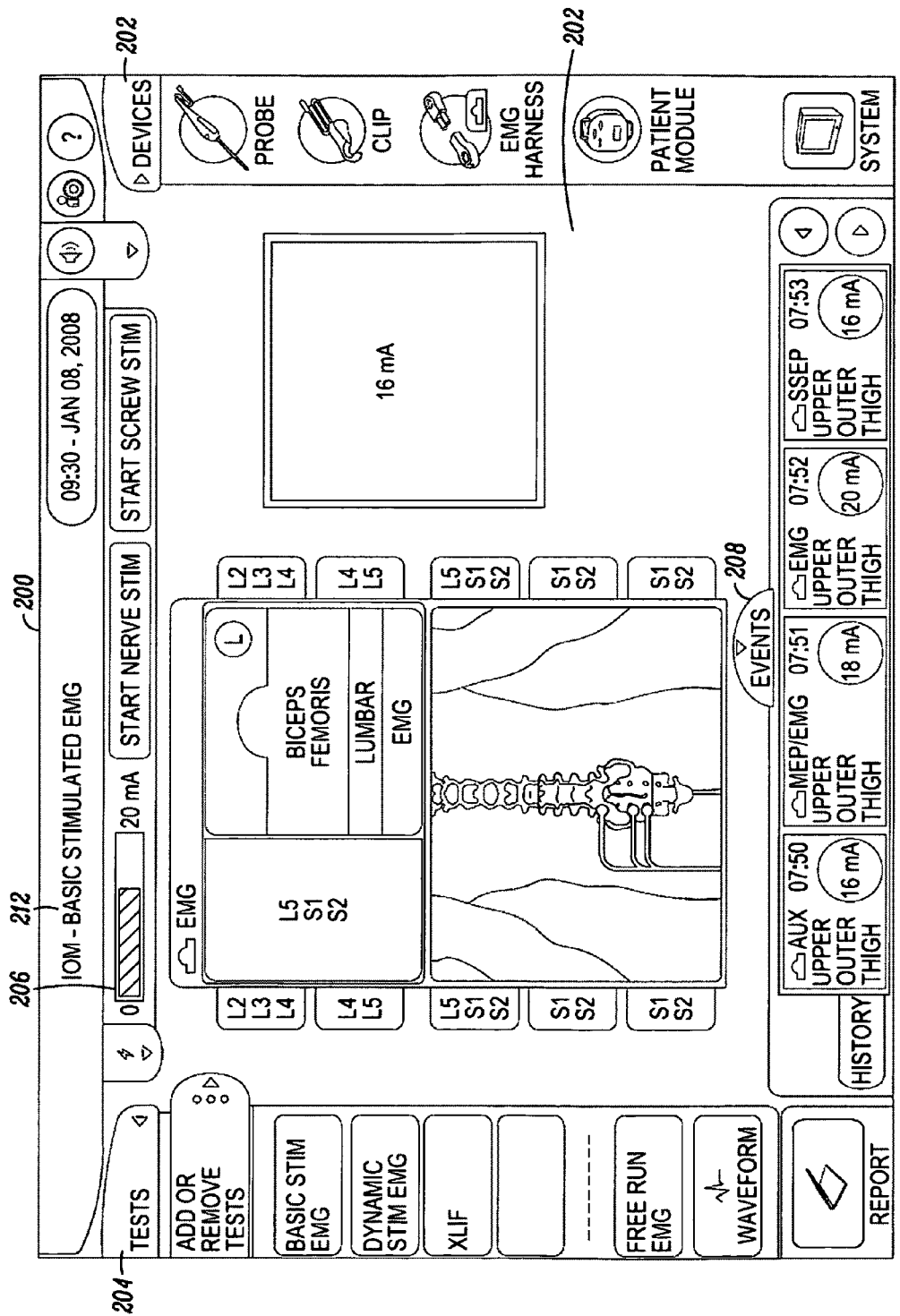
Figure 26A:
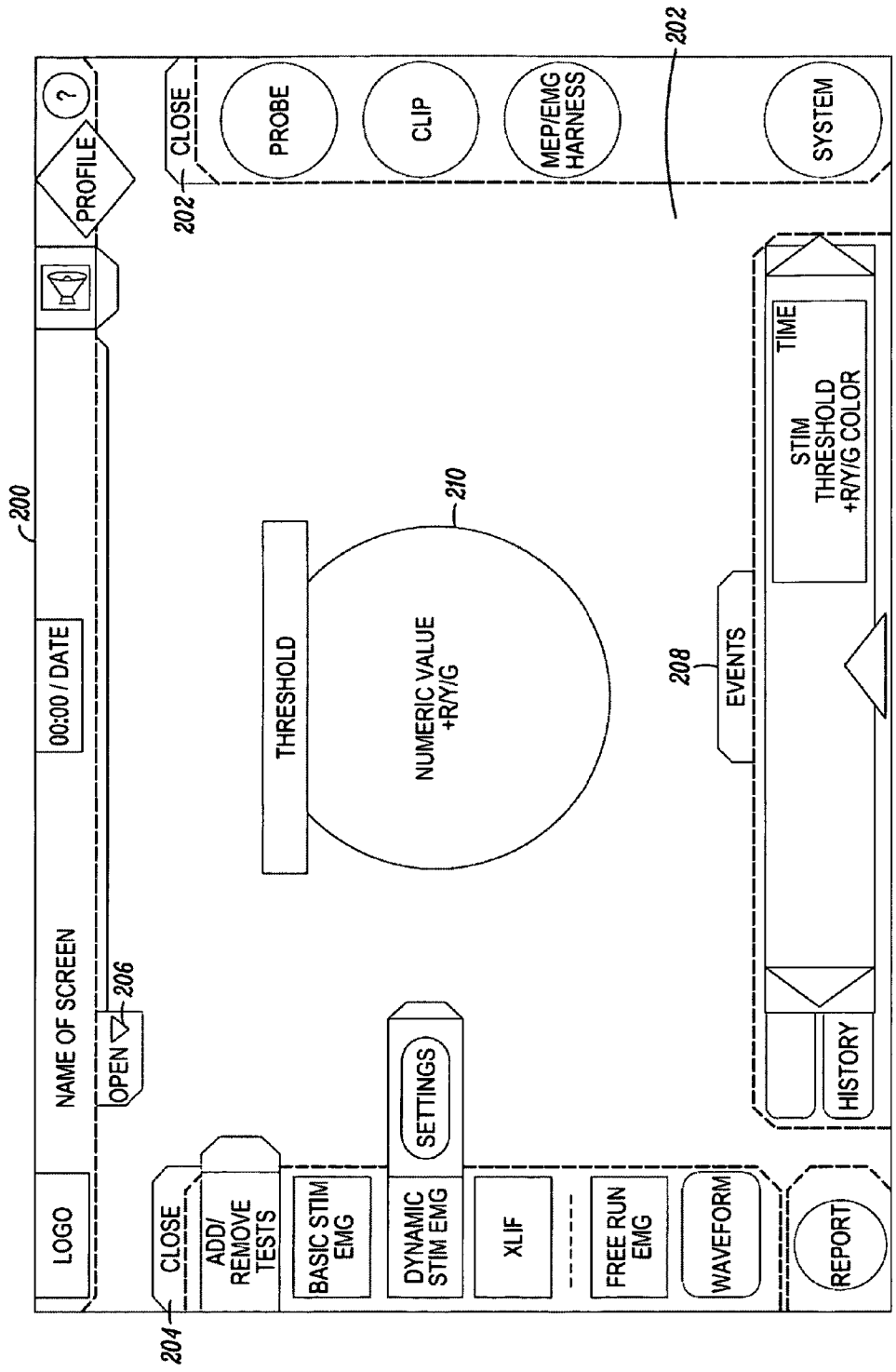
FIG. 26A-26B are a block diagram and screenshot, respectively, of a third example of a monitoring screen forming part of the neurophysiology system of FIG. 1.
Figure 26B:
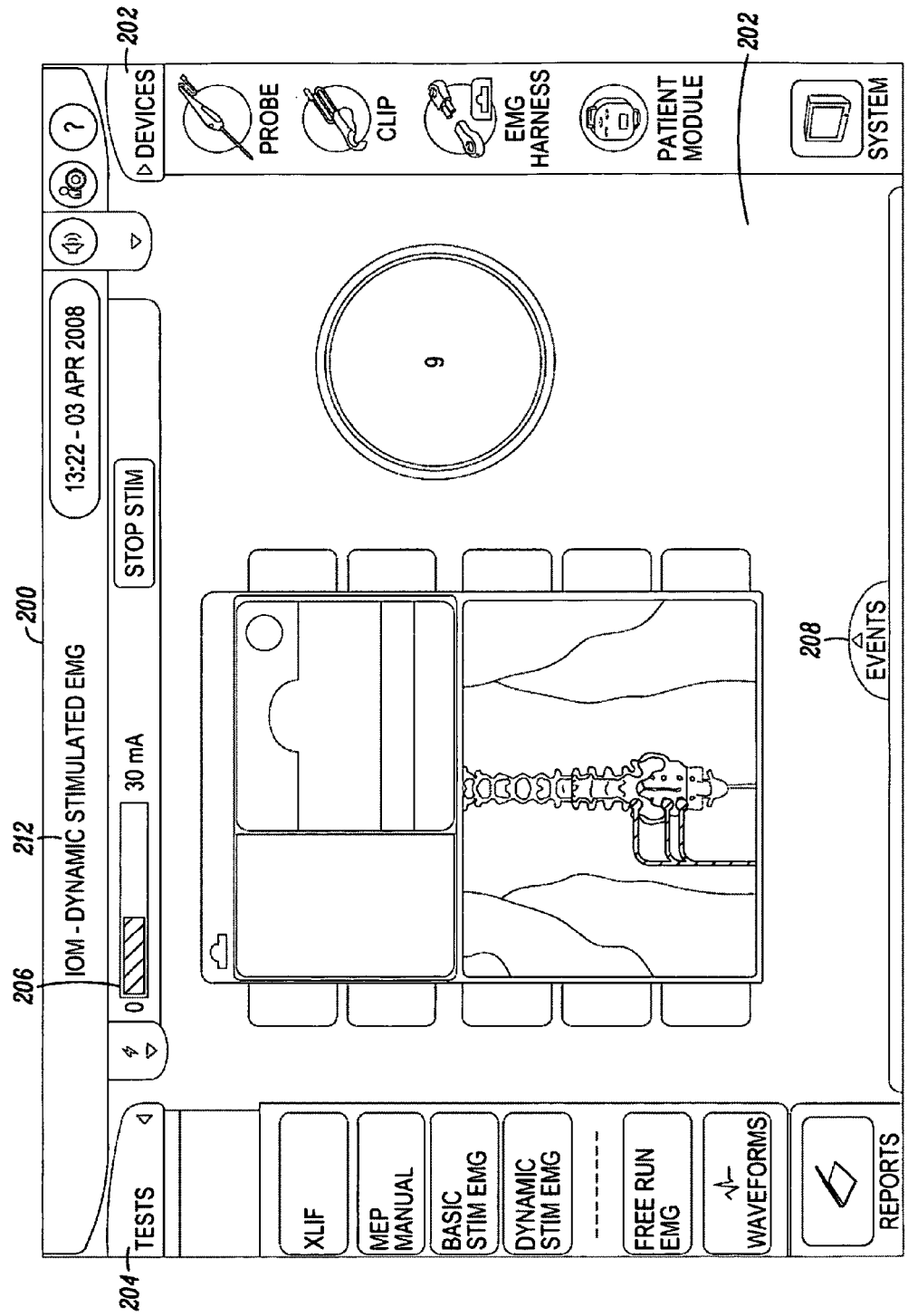

Stimulation results (including but not necessarily limited to at least one of the numerical $I_{thresh}$ value and color coded safety level indication) and other relevant data are conveyed to the user on at least main display 34, as illustrated in FIGS. 25A-25B and 26A-26B. FIGS. 25A-25B illustrate the monitoring screen 200 with the Basic Stimulation EMG test selected. FIGS. 26A-26B illustrate the monitoring screen 200 with the Dynamic Stimulation EMG test selected. In one embodiment of the various screw test functions (e.g. Basic and Dynamic), green corresponds to a threshold range of greater than 10 milliamps (mA), a yellow corresponds to a stimulation threshold range of 7-10 mA, and a red corresponds to a stimulation threshold range of 6 mA or below. EMG channel tabs may be selected via the touch screen display 26 to show the $I_{thresh}$ of the corresponding nerves. Additionally, the EMG channel possessing the lowest $I_{thresh}$ may be automatically highlighted and/or colored to clearly indicate this fact to the user.

Figure 27A:
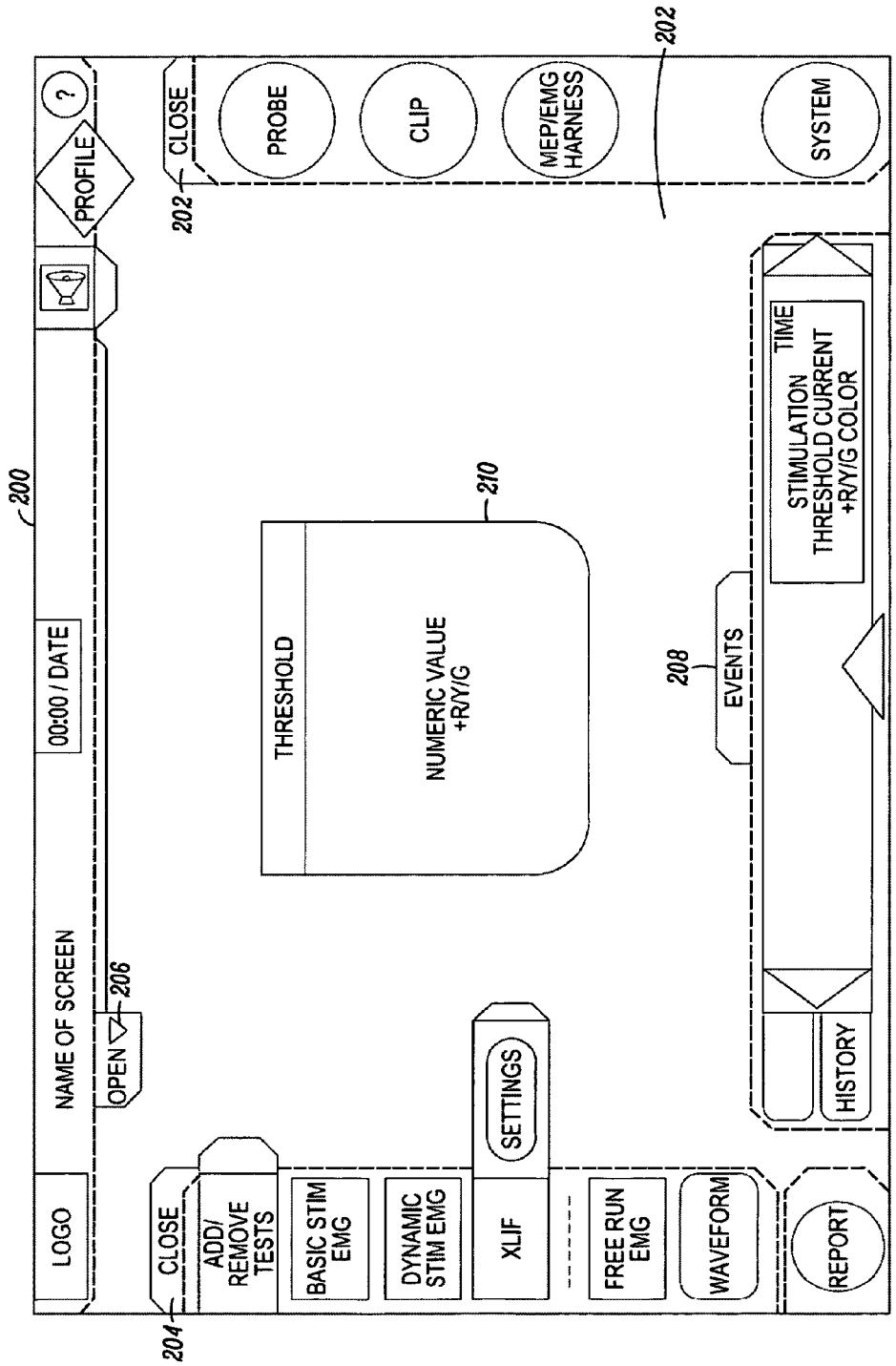
FIG. 27A-27B are a block diagram and screenshot, respectively, of a fourth example of a monitoring screen forming part of the neurophysiology system of FIG. 1.
Figure 27B:
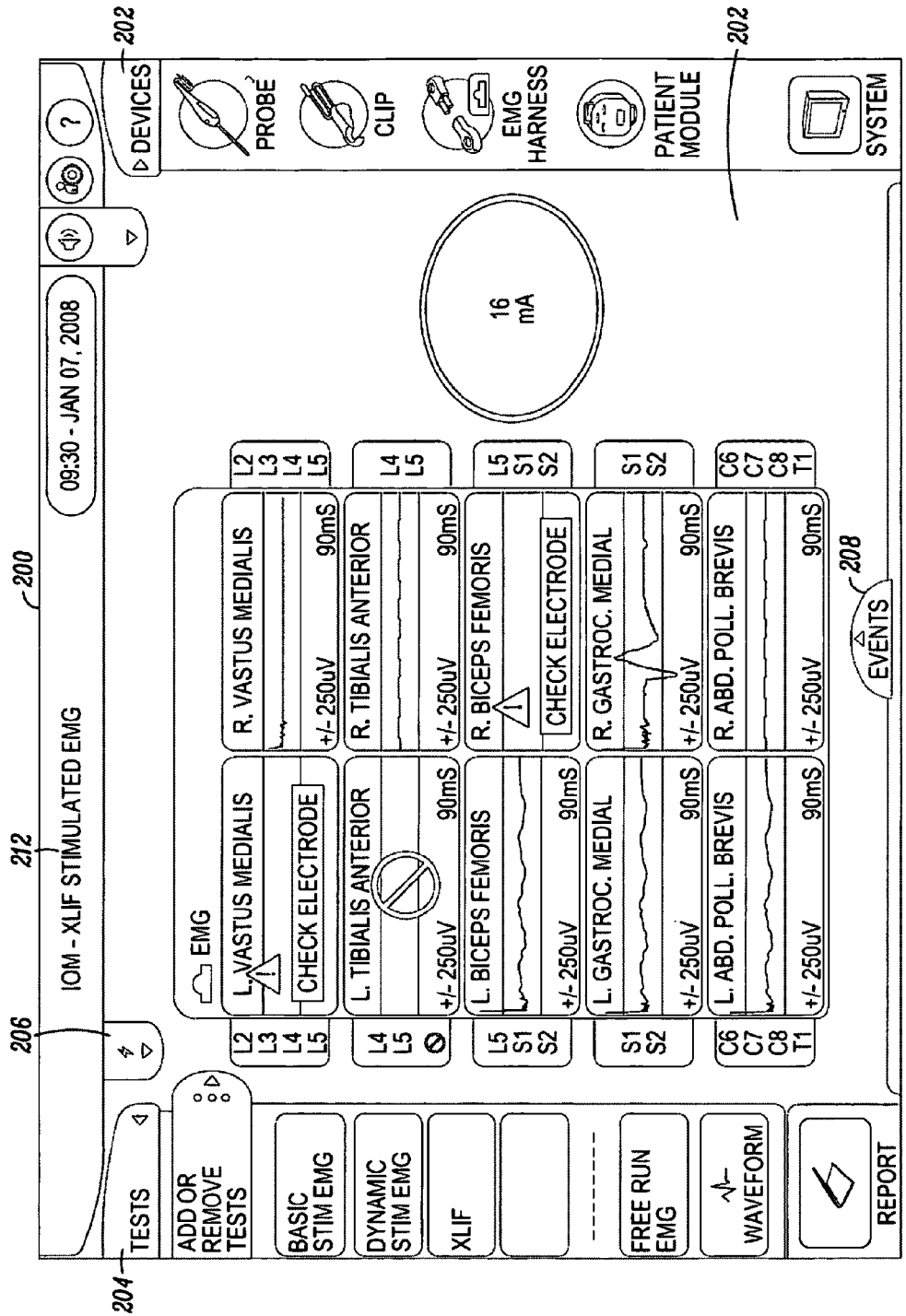

The neuromonitoring system 10 may perform nerve proximity testing, via the XLIF mode, to ensure safe and reproducible access to surgical target sites. Using the surgical access components 26-32, the system 10 detects the existence of neural structures before, during, and after the establishment of an operative corridor through (or near) any of a variety of tissues having such neural structures which, if contacted or impinged, may otherwise result in neural impairment for the patient. The surgical access components 26-32 are designed to bluntly dissect the tissue between the patient's skin and the surgical target site. Dilators of increasing diameter, which are equipped with one or more stimulating electrodes, are advanced towards the target site until a sufficient operating corridor is established to advance retractor 32 to the target site. As the dilators are advanced to the target site electrical stimulation signals are emitted via the stimulation electrodes. The stimulation signal will stimulate nerves in close proximity to the stimulation electrode and the corresponding EMG response is monitored. As a nerve gets closer to the stimulation electrode, the stimulation current required to evoke a muscle response decreases because the resistance caused by human tissue will decrease, and it will take less current to cause nervous tissue to depolarize. $I_{thresh}$ is calculated, using the basic threshold hunting algorithm described below, providing a measure of the communication between the stimulation signal and the nerve and thus giving a relative indication of the proximity between access components and nerves. An example of the monitoring screen 200 with XLIF mode active is depicted in FIGS. 27A-27B. In a preferred embodiment, a green or safe level corresponds to a stimulation threshold range of 10 milliamps (mA) or greater, a yellow level denotes a stimulation threshold range of 5-9 mA, and a red level denotes a stimulation threshold range of 4 mA or below.

Figure 28A:
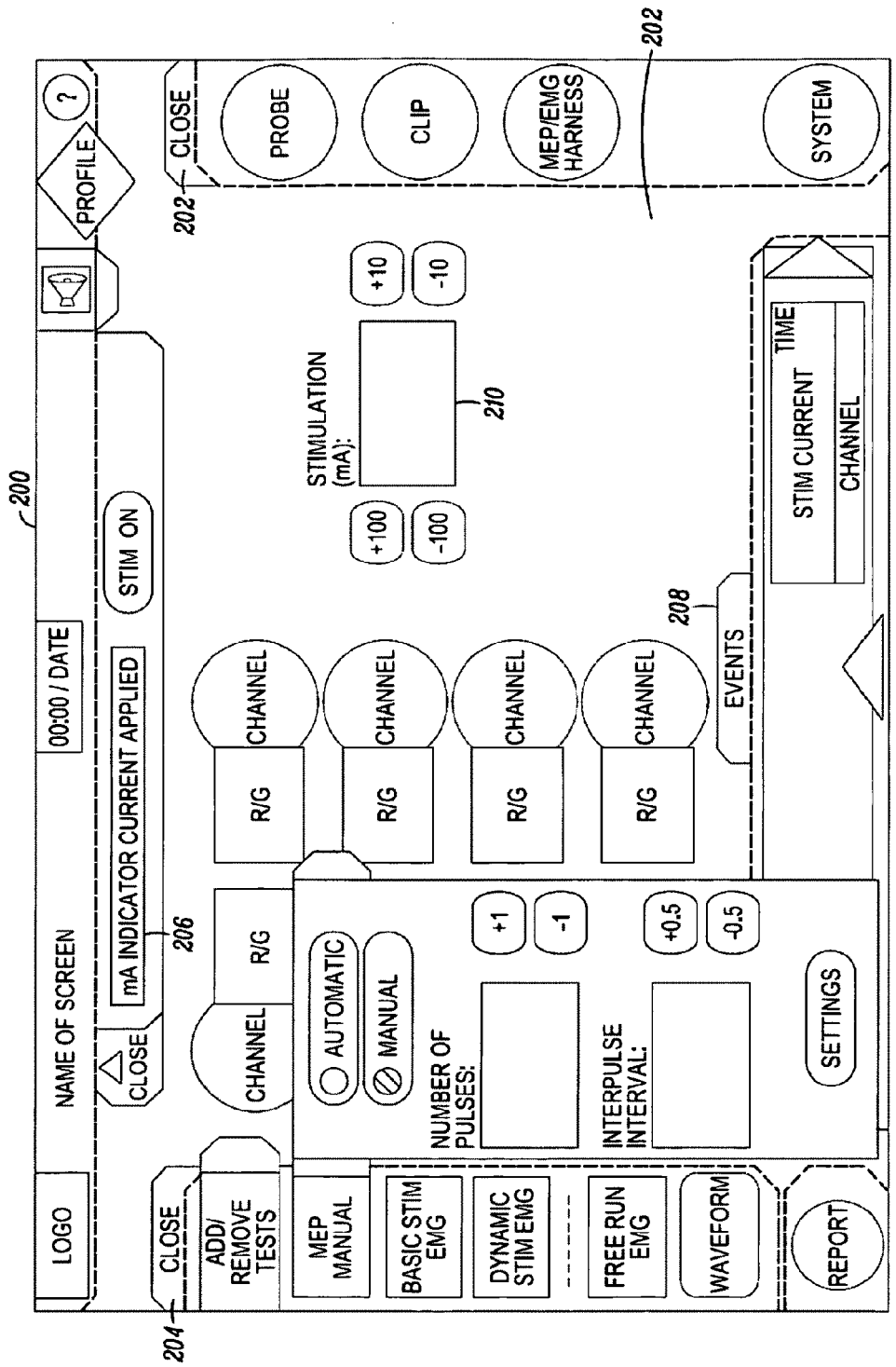
FIG. 28A-28B are a block diagram and screenshot, respectively, of a fifth example of a monitoring screen forming part of the neurophysiology system of FIG. 1.
Figure 28B:
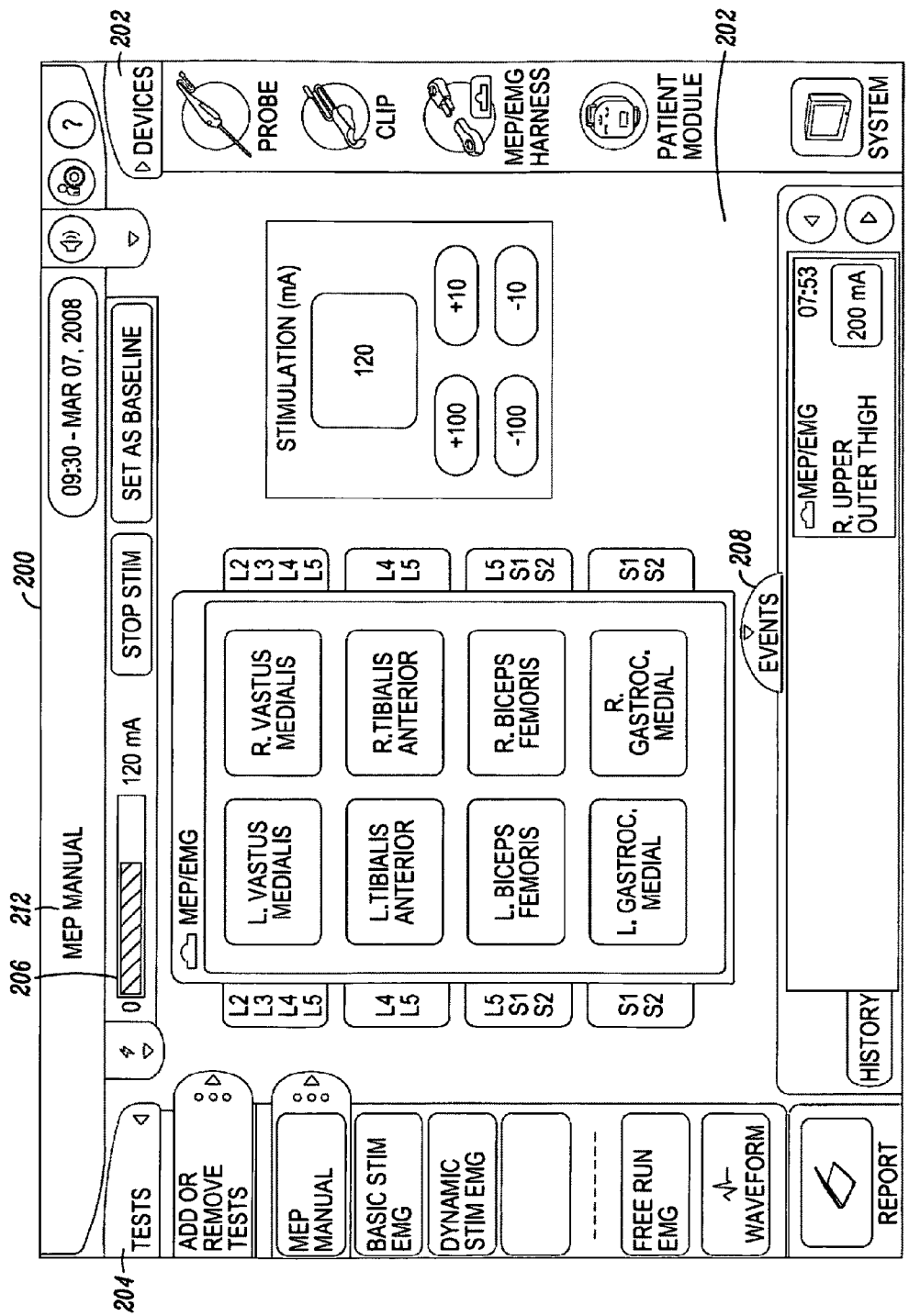
Figure 29A:
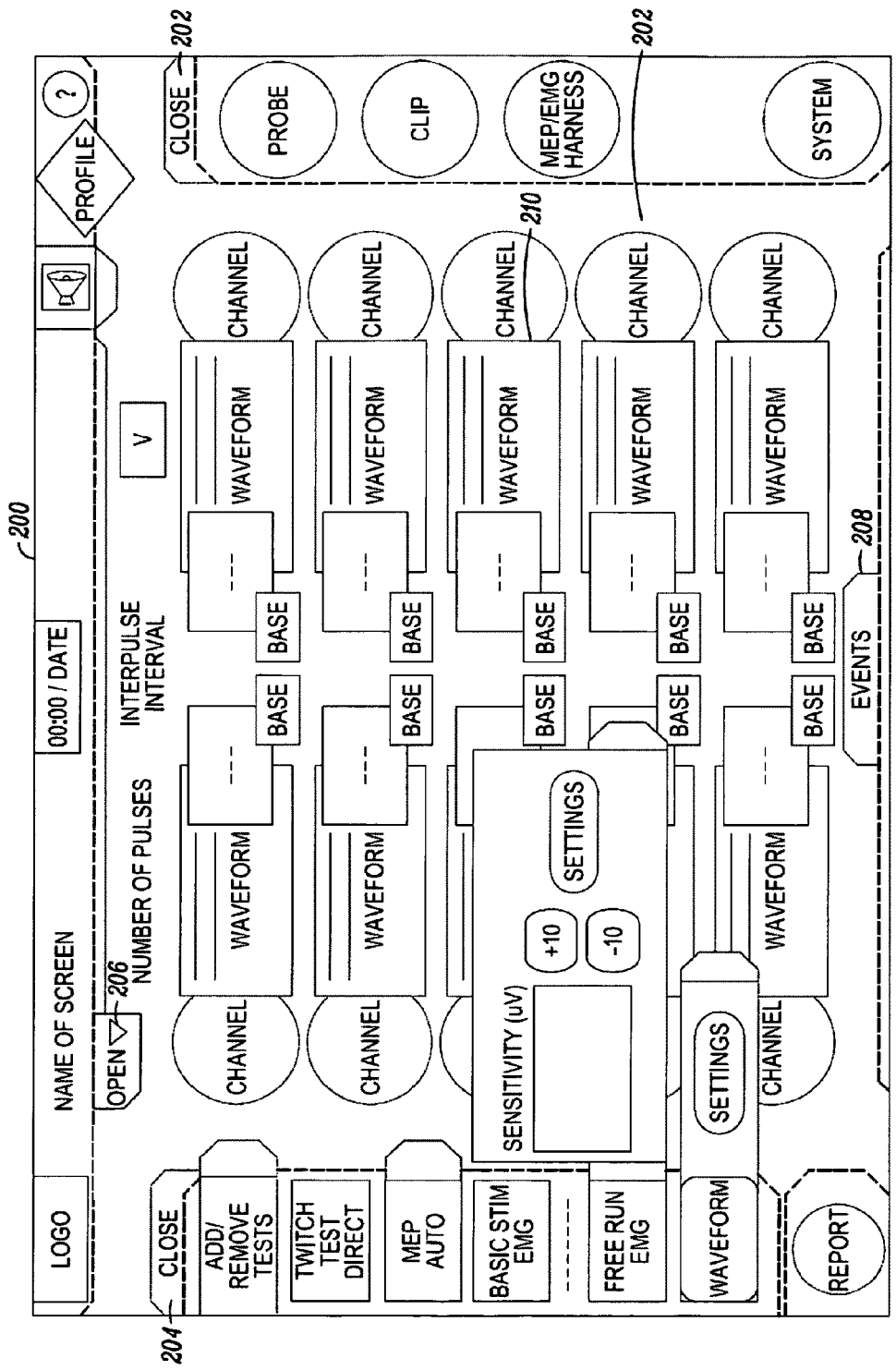
FIG. 29A-29B are a block diagram and screenshot, respectively, of a sixth example of a monitoring screen forming part of the neurophysiology system of FIG. 1.
Figure 29B:
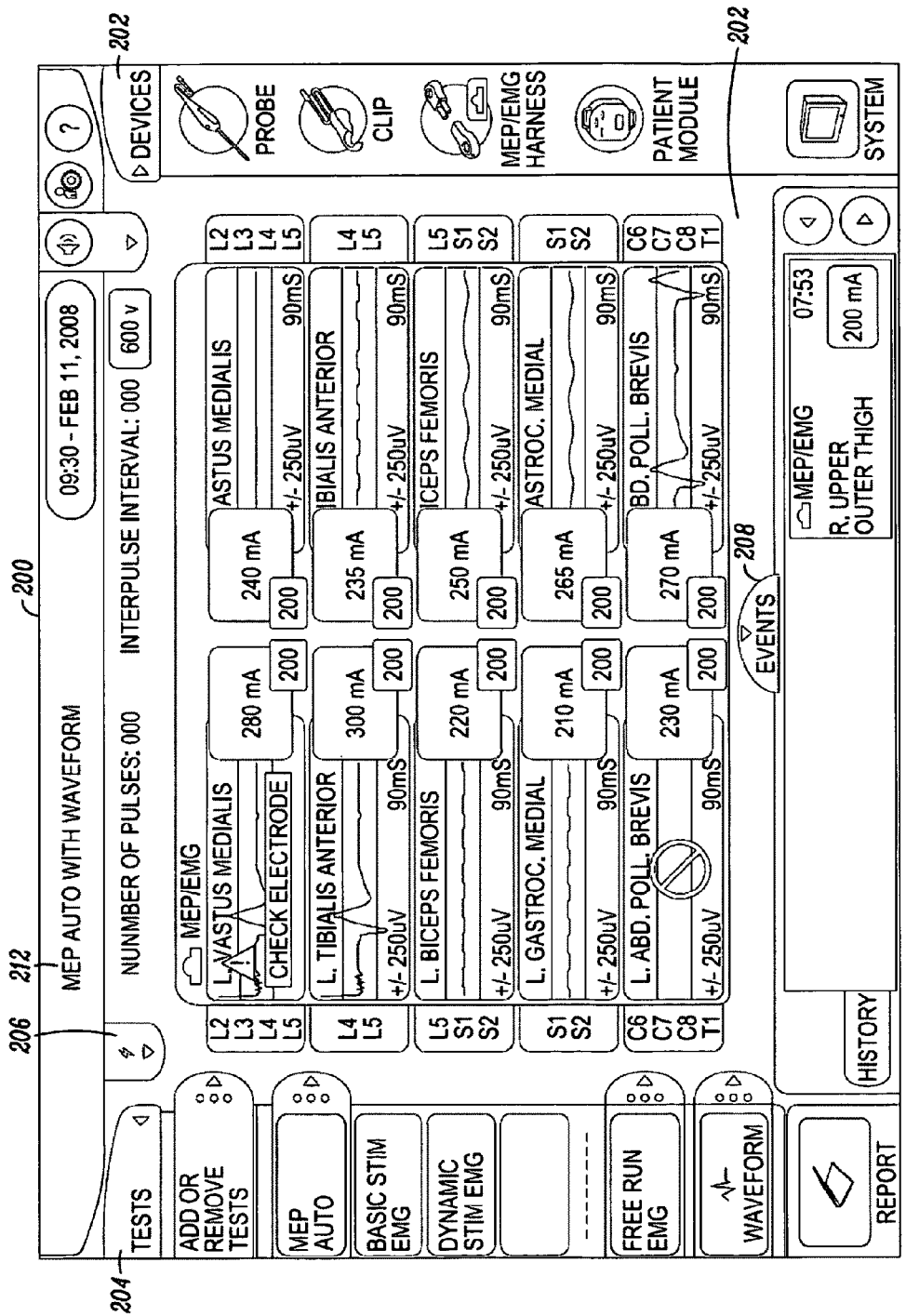

The neuromonitoring system 10 performs assessments of spinal cord health using one or more of MEP Auto, MEP Manual, and SSEP modes. In MEP modes, stimulation signals are delivered to the Motor Cortex via patient module 14 and resulting EMG responses are detected from various muscles in the upper and lower extremities. An increase in $I_{thresh}$ from an earlier test to a later test may indicate a degradation of spinal cord function. Likewise, the absence of a significant EMG response to a given $I_{stim}$ on a channel that had previously reported a significant response to the same or lesser $I_{stim}$ is also indicative of a degradation in spinal cord function. These indicators are detected by the system in the MEP modes and reported to the surgeon. In MEP Auto mode the system determines the $I_{thresh}$ baseline for each channel corresponding to the various monitored muscles, preferably early in the procedure, using the multi-channel algorithm described. Throughout the procedure subsequent tests may be conducted to again determine $I_{thresh}$ for each channel. The difference between the resulting $I_{thresh}$ values and the corresponding baseline are computed by the system 10 and compared against predetermined "safe" and "unsafe" difference values. The $I_{thresh}$, baseline, and difference values are displayed to the user, along with any other indicia of the safety level determined (such as a red, yellow, green color code), on the display 34, as illustrated in FIGS. 28A-28B. In MEP Manual mode, the user selects the stimulation current level and the system reports whether or not the stimulation signal evokes a significant response on each channel. Stimulation results may be shown on the display 34 in the form of "YES" and "NO" responses, or other equivalent indicia, as depicted in FIGS. 29A-29B. Using either mode the surgeon may thus be alerted to potential complications with the spinal cord and any corrective actions deemed necessary may be undertaken at the discretion of the surgeon.

Figure 30:
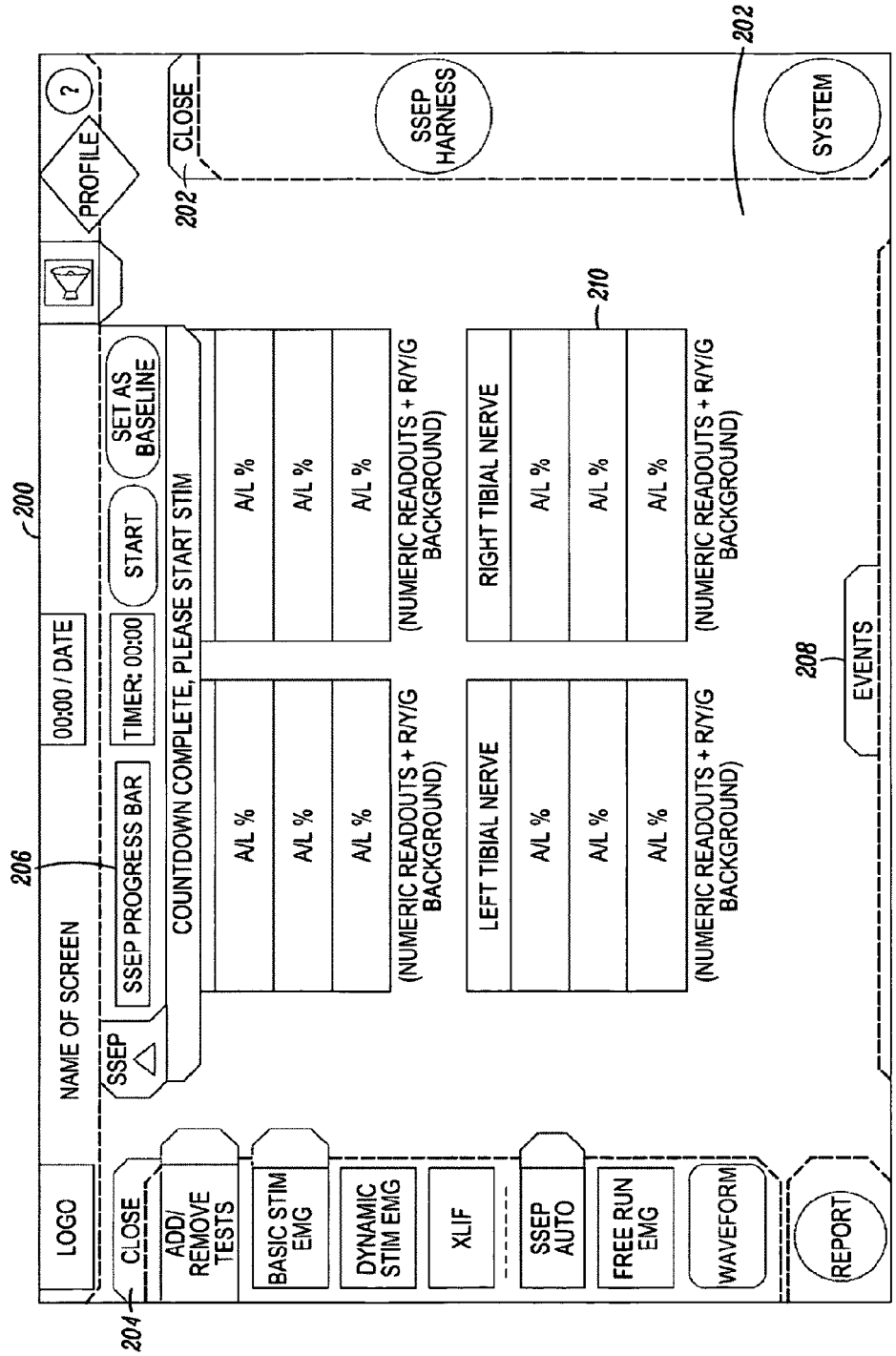
FIG. 30 is a block diagram of a seventh example of a monitoring screen forming part of the neurophysiology system of FIG. 1.

In SSEP mode, the neuromonitoring system 10 stimulates peripheral sensory nerves that exit the spinal cord below the level of surgery and then measures the electrical action potential from electrodes located on the nervous system tract superior to the surgical target site. To accomplish this, stimulation electrodes 22 may be placed on the skin over the desired peripheral nerve (such as by way of example only, the Posterior Tibial nerve and/or the Ulnar nerve) and recording electrodes 23 are positioned on the recording sites (such as, by way of example only, C2 vertebra, scalp, Erb's point, and pop fossa) and stimulation signals are delivered from the patient module 14. Damage in the spinal cord may disrupt the transmission of the signal up the cord resulting in a weakened or delayed signal at the recording site. The system 10 determines differences in amplitude and latency between a signal response and a baseline signal response. The differences are compared against predetermined "safe" and "unsafe" levels and the results are displayed on display 34 as seen in the exemplary screen view illustrated in FIG. 30.

The neuromonitoring system 10 may also conduct free-run EMG monitoring while the system is in any of the above-described modes. Free-run EMG monitoring continuously listens for spontaneous muscle activity that may be indicative of potential danger. The system 10 may automatically cycle into free-run monitoring after 5 seconds (by way of example only) of inactivity. Initiating a stimulation signal in the selected mode will interrupt the free-run monitoring until the system 10 has again been inactive for five seconds, at which time the free-run begins again.

The neuromonitoring system 10 may also perform a navigated guidance function. The navigated guidance feature may be used by way of example only, to ensure safe and reproducible pedicle screw placement by monitoring the axial trajectory of surgical instruments used during pilot hole formation and/or screw insertion. Preferably, EMG monitoring may be performed simultaneously with the navigated guidance feature. To perform the navigated guidance and angle-measuring device (hereafter "tilt sensor") 54 is connected to the patient module 14 via one of the accessory ports 62. The tilt sensor measures its angular orientation with respect to a reference axis (such as, for example, "vertical" or "gravity") and the control unit displays the measurements. Because the tilt sensor is attached to a surgical instrument the angular orientation of the instrument, may be determined as well, enabling the surgeon to position and maintain the instrument along a desired trajectory during use. In general, to orient and maintain the surgical instrument along a desired trajectory during pilot hole formation, the surgical instrument is advanced to the pedicle (through any of open, mini-open, or percutaneous access) while oriented in the zero-angle position. The instrument is then angulated in the sagittal plane until the proper cranial-caudal angle is reached. Maintaining the proper cranial-caudal angle, the surgical instrument may then be angulated in the transverse plane until the proper medial-lateral angle is attained. Once the control unit 12 indicates that both the medial-lateral and cranial caudal angles are matched correctly, the instrument may be advanced into the pedicle to form the pilot hole, monitoring the angular trajectory of the instrument until the hole formation is complete.

Figure 31:
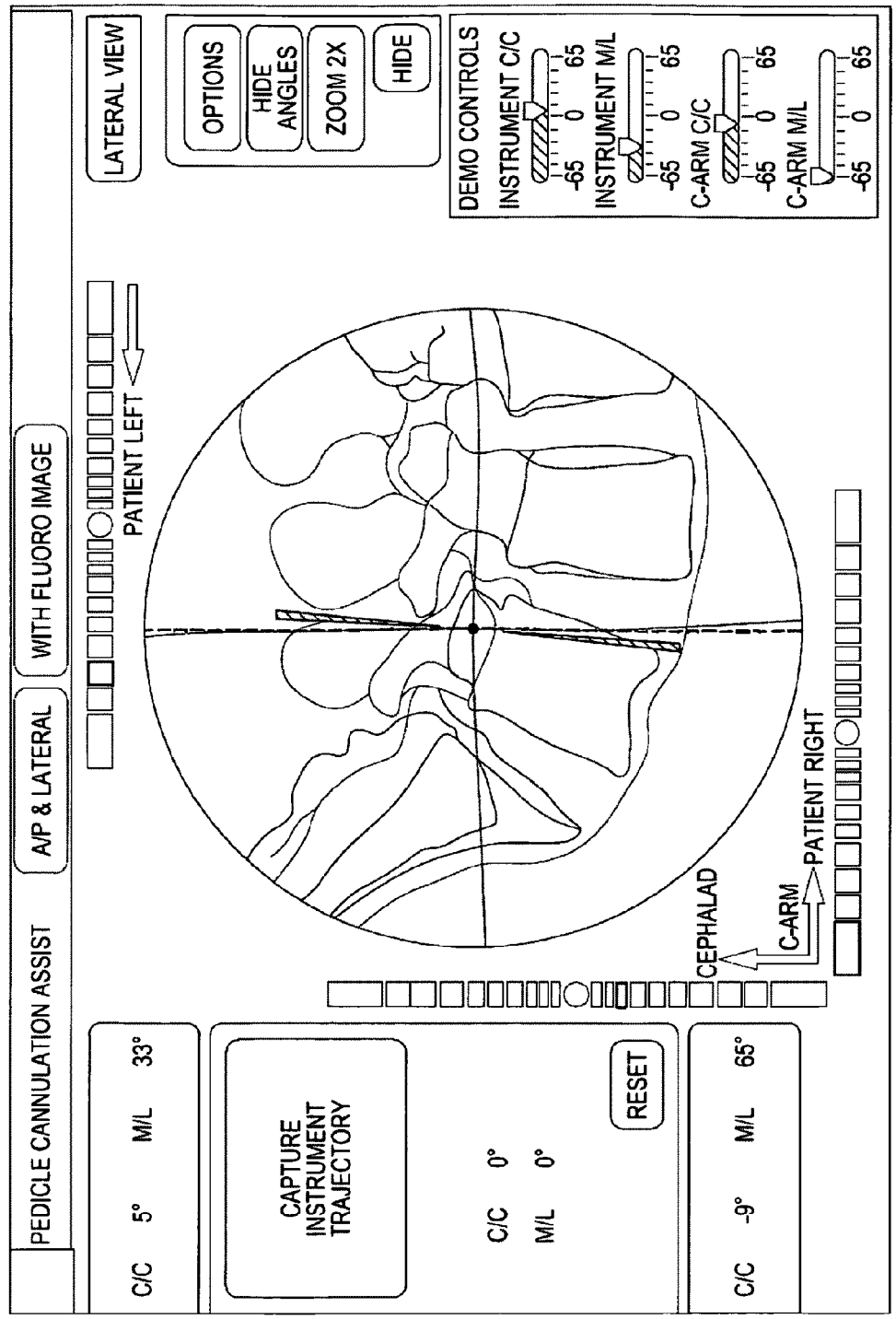
FIG. 31 is a screenshot of an eighth example of a monitoring screen forming part of the neurophysiology system of FIG. 1.

The control unit 12 may communicate any of numerical, graphical, and audio feedback corresponding to the orientation of the tilt sensor in the sagittal plane (cranial-caudal angle) and in the transverse plane (medial-lateral angle). The medial-lateral and cranial-caudal angle readouts may be displayed simultaneously and continuously while the tilt sensor is in use, or any other variation thereof (e.g. individually and/or intermittently). FIG. 31 illustrates, by way of example only, one embodiment of a GUI screen for the Navigated Guidance function. The angular orientation of the instrument is displayed along with a color coded targeting scheme to help the user find the desired angle.

To obtain $I_{thresh}$ and take advantage of the useful information it provides, the system 10 identifies and measures the peak-to-peak voltage ($V_{pp}$) of each EMG response corresponding to a given stimulation current ($I_{Stim}$). Identifying the true $V_{pp}$ of a response may be complicated by the existence of stimulation and/or noise artifacts which may create an erroneous $V_{pp}$ measurement. To overcome this challenge, the neuromonitoring system 10 of the present invention may employ any number of suitable artifact rejection techniques such as those shown and described in full in the above referenced co-pending and commonly assigned PCT App. Ser. No. PCT/US2004/025550, entitled "System and Methods for Performing Dynamic Pedicle Integrity Assessments," filed on Aug. 5, 2004, the entire contents of which are incorporated by reference into this disclosure as if set forth fully herein. Upon measuring $V_{pp}$ for each EMG response, the $V_{pp}$ information is analyzed relative to the corresponding stimulation current ($I_{stim}$) in order to identify the minimum stimulation current ($I_{Thresh}$) capable of resulting in a predetermined $V_{pp}$ EMG response. According to the present invention, the determination of $I_{Thresh}$ may be accomplished via any of a variety of suitable algorithms or techniques.

FIGS. 32A-32D illustrate, by way of example only, the principles of a threshold hunting algorithm of the present invention used to quickly find $I_{thresh}$. The method for finding $I_{thresh}$ utilizes a bracketing method and a bisection method. The bracketing method quickly finds a range (bracket) of stimulation currents that must contain $I_{thresh}$ and the bisection method narrows the bracket until $I_{thresh}$ is known within a specified accuracy. If the stimulation current threshold, $I_{thresh}$, of a channel exceeds a maximum stimulation current, that threshold is considered out of range.

Figure 32A:
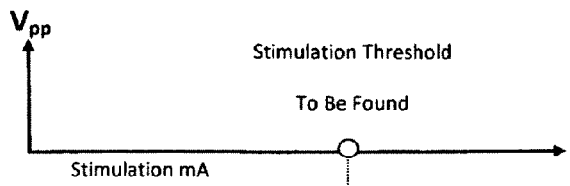
FIGS. 32A-32D are graphs illustrating the fundamental steps of a rapid current threshold-hunting algorithm according to one embodiment of the present invention.
Figure 32B:
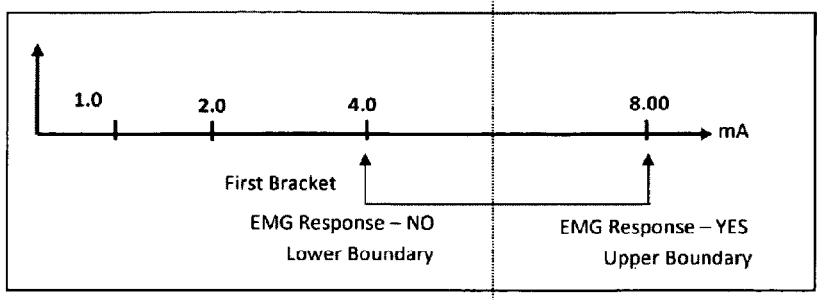

FIG. 32B illustrates the bracketing feature of the threshold hunting algorithm of the present invention. Stimulation begins at a minimum stimulation current, such as (by way of example only) 1 mA. It will be appreciated that the relevant current values depend in part on the function performed (e.g. high currents are used for MEP and low currents are generally used for other functions) and the current values described here are for purposes of example only and may in actuality be adjusted to any scale The level of each subsequent stimulation is doubled from the preceding stimulation level until a stimulation current recruits (i.e. results in an EMG response with a $V_{pp}$ greater or equal to $V_{thresh}$). The first stimulation current to recruit (8 mA in FIG. 32B), together with the last stimulation current to have not recruited (4 mA in FIG. 32B), forms the initial bracket.

Figure 32C:
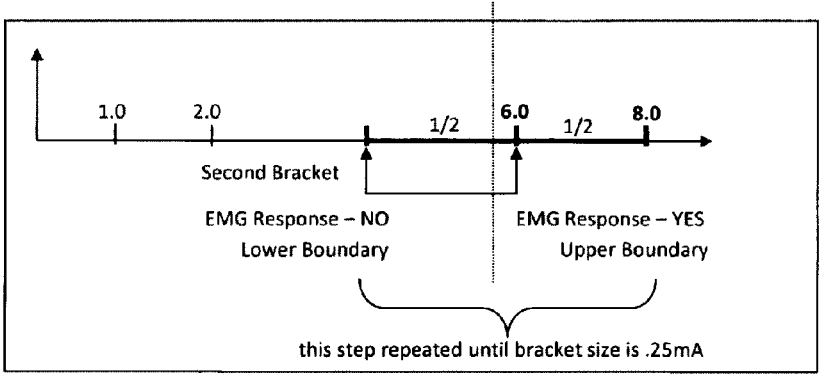
Figure 32D:
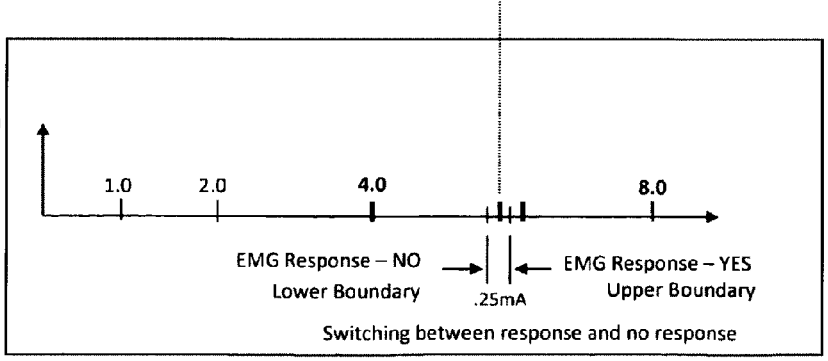

FIGS. 32C-32D illustrate the bisection feature of the threshold hunting algorithm of the present invention. After the threshold current $t_{thresh}$ has been bracketed (FIG. 32B), the initial bracket is successively reduced via bisection to a predetermined width, such as (by way of example only) 0.25 mA. This is accomplished by applying a first bisection stimulation current that bisects (i.e. forms the midpoint of) the initial bracket (6 mA in FIG. 32C). If this first bisection stimulation current recruits, the bracket is reduced to the lower half of the initial bracket (e.g. 4 mA and 6 mA in FIG. 32C). If this first bisection stimulation current does not recruit, the bracket is reduced to the upper half of the initial bracket (e.g. 6 mA and 8 mA in FIG. 32C). This process is continued for each successive bracket until $I_{thresh}$ is bracketed by stimulation currents separated by the predetermined width (which, in this case, is 0.25 mA). In this example shown, this would be accomplished by applying a second bisection stimulation current (forming the midpoint of the second bracket, or 5 mA in this example). Because this second bisection stimulation current is below $I_{thresh}$, it will not recruit. As such, the second bracket will be reduced to the upper half thereof (5 mA to 6 mA), forming a third bracket. A third bisection stimulation current forming the mid-point of the third bracket (5.50 mA in this case) will then be applied. Because this third bisection stimulation current is below $I_{thresh}$, it will not recruit. As such, the third bracket will be reduced to the upper half thereof (5.50 mA to 6 mA), forming a fourth bracket. A fourth bisection stimulation current forming the mid-point of the fourth bracket (5.75 mA in this case) will then be applied. Because the fourth bisection stimulation current is above $I_{thresh}$, it will recruit. The final bracket is therefore between 5.50mA and 5.75 mA. Due to the "response" or recruitment at 5.50 mA and "no response" or lack of recruitment at 5.75 mA, it can be inferred that $I_{tresh}$ is within this range. In one embodiment, the midpoint of this final bracket may be defined $I_{thresh}$, however, any value falling within the final bracket may be selected as $I_{thresh}$ without departing from the scope of the present invention. Depending on the active mode, the algorithm may stop after finding $I_{thresh}$ for the first responding channel (i.e. the channel with the lowest $I_{thresh}$) or the bracketing and bisection steps may be repeated for each channel to determine $I_{thresh}$ for each channel. In one embodiment, this multiple channel $I_{thresh}$ determination may be accomplished by employing the additional steps of the multi-channel threshold detection algorithm, described below.

Additionally, in the "dynamic" functional modes, including, but not necessarily limited to Dynamic Stimulation EMG and XLIF, the system may continuously update the stimulation threshold level and indicate that level to the user. To do so, the threshold hunting algorithm does not repeatedly determine the $I_{thresh}$ level anew, but rather, it determines whether stimulation current thresholds are changing. This is accomplished, as illustrated in FIG. 32D, by a monitoring phase that involves switching between stimulations at lower and upper ends of the final bracket. If the threshold has not changed then the lower stimulation current should not evoke a response, while the upper end of the bracket should. If either of these conditions fail, the bracket is adjusted accordingly. The process is repeated for each of the active channels to continue to assure that each threshold is bracketed. If stimulations fail to evoke the expected response three times in a row, then the algorithm transitions back to the bracketing state in order to reestablish the bracket. In the event a change in $I_{thresh}$ is detected during the monitoring phase, the user may be alerted immediately via the screen display and/or audio feedback. By way of example only, the color shown on the display corresponding to the previous $I_{thresh}$ can be altered to a neutral color (e.g. black, grey, etc . . . ) as soon as the change in $I_{thresh}$ is detected but before the new $I_{thresh}$ value is determined. If an audio tone is used to represent a particular safety level, the tone can ceased as soon as the change in detected. Once the new $I_{thresh}$ value is determined the color and/or audio tone can be altered again to signify the value.

Figure 33:
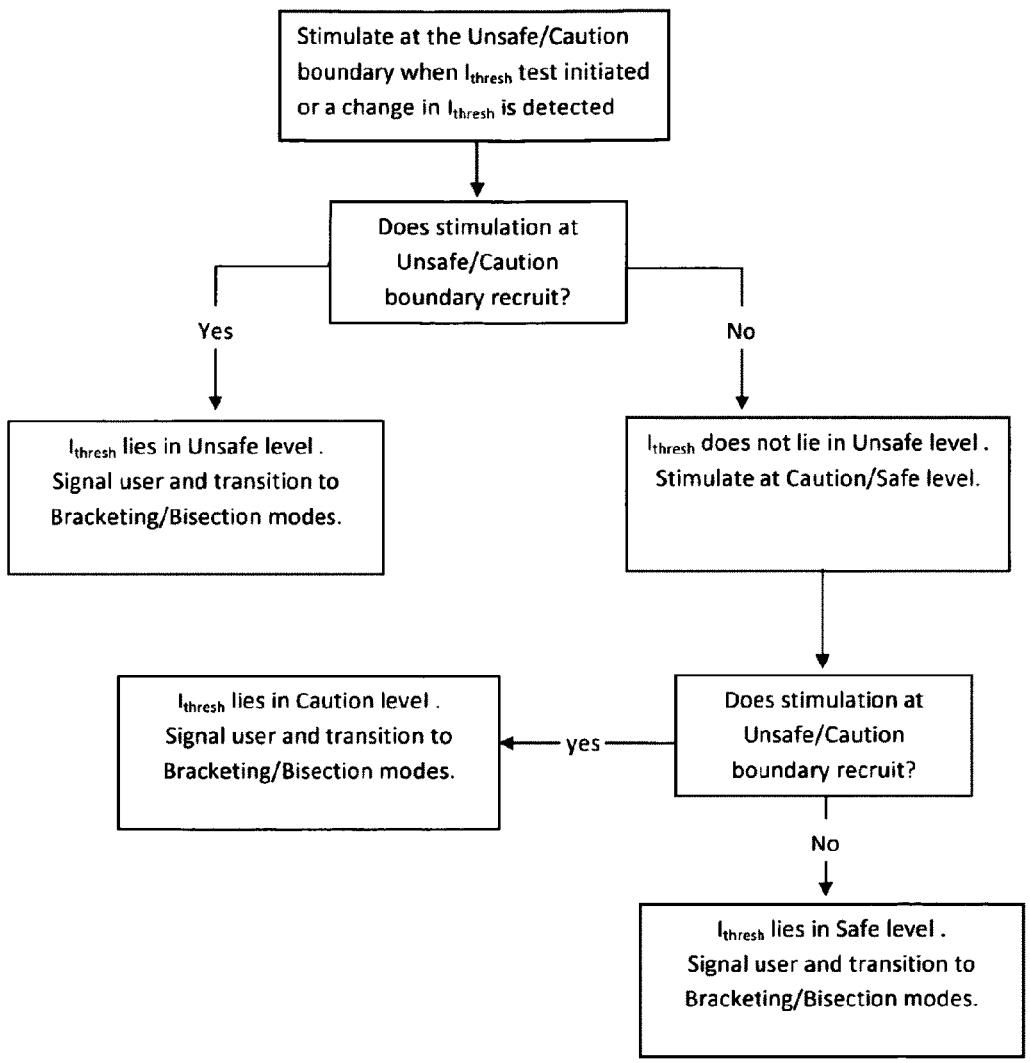
FIG. 33 is block diagram illustrating the steps of an initiation sequence for determining a relevant safety level prior to determining a precise threshold value according to an alternate embodiment of the threshold hunting algorithm of FIG. 7A-7D.

In an alternative embodiment, rather than beginning by entering the bracketing phase at the minimum stimulation current and bracketing upwards until $I_{thresh}$ is bracketed, the threshold hunting algorithm may begin by immediately determining the appropriate safety level and then entering the bracketing phase. The algorithm may accomplish this by initiating stimulation at one or more of the boundary current levels. By way of example only, and with reference to FIG. 33, the algorithm may begin by delivering a stimulation signal at the boundary between the unsafe (e.g. red) and caution (e.g. yellow) levels. If the safety level is not apparent after the first stimulation, the algorithm may stimulate again at the boundary between the caution (e.g. yellow) and safe (e.g. green) levels. Once the safety level is known (i.e. after the first stimulation if the safety level is red, or, after the second stimulation if the safety level is yellow or green) the screen display may be updated to the appropriate color and/or coded audio signals may be emitted. As the screen display is updated, the algorithm may transition to the bracketing and bisection phases to determine the actual $I_{thresh}$ value. When the $I_{thresh}$ value is determined the display may be updated again to reflect the additional information. In dynamic modes, if the monitoring phase detects a change in $I_{thresh}$, the algorithm will again stimulate at the boundary level(s) as necessary and update the color and/or audio signals before transitioning to the bracketing and bisection phases to determine the new $I_{thresh}$.

For some functions, such as (by way of example) MEP, it may be desirable to obtain $I_{thresh}$ for each active channel each time the function is performed. This is particularly advantageous when assessing changes in $I_{thresh}$ over time as a means to detect potential problems (as opposed to detecting an $I_{thresh}$ below a predetermined level determined to be safe, such as in the Stimulated EMG modes). While $I_{thresh}$ can be found for each active channel using the algorithm as described above, it requires a potentially large number of stimulations, each of which is associated with a specific time delay, which can add significantly to the response time. Done repeatedly, it could also add significantly to the overall time required to complete the surgical procedure, which may present added risk to the patient and added costs. To overcome this drawback, a preferred embodiment of the neuromonitoring system 10 boasts a multi-channel threshold hunting algorithm so as to quickly determine $I_{thresh}$ for each channel while minimizing the number of stimulations and thus reduce the time required to perform such determinations.

The multi-channel threshold hunting algorithm reduces the number stimulations required to complete the bracketing and bisection steps when $I_{thresh}$ is being found for multiple channels. The multi-channel algorithm does so by omitting stimulations for which the result is predictable from the data already acquired. When a stimulation signal is omitted, the algorithm proceeds as if the stimulation had taken place. However, instead of reporting an actual recruitment result, the reported result is inferred from previous data. This permits the algorithm to proceed to the next step immediately, without the time delay associated with a stimulation signal.

Regardless of what channel is being processed for $I_{thresh}$, each stimulation signal elicits a response from all active channels. That is to say, every channel either recruits or does not recruit in response to a stimulation signal (again, a channel is said to have recruited if a stimulation signal evokes an EMG response deemed to be significant on that channel, such as $V_{pp}$ of approximately 100 uV). These recruitment results are recorded and saved for each channel. Later, when a different channel is processed for $I_{thresh}$, the saved data can be accessed and, based on that data, the algorithm may omit a stimulation signal and infer whether or not the channel would recruit at the given stimulation current.

There are two reasons the algorithm may omit a stimulation signal and report previous recruitment results. A stimulation signal may be omitted if the selected stimulation current would be a repeat of a previous stimulation. By way of example only, if a stimulation current of 1 mA was applied to determine $I_{thresh}$ for one channel, and a stimulation at 1 mA is later required to determine $I_{thresh}$ for another channel, the algorithm may omit the stimulation and report the previous results. If the specific stimulation current required has not previously been used, a stimulation signal may still be omitted if the results are already clear from the previous data. By way of example only, if a stimulation current of 2 mA was applied to determine $I_{thresh}$ for a previous channel and the present channel did not recruit, when a stimulation at 1 mA is later required to determine $I_{thresh}$ for the present channel, the algorithm may infer from the previous stimulation that the present channel will not recruit at 1 mA because it did not recruit at 2 mA. The algorithm may therefore omit the stimulation and report the previous result.

Figure 34:
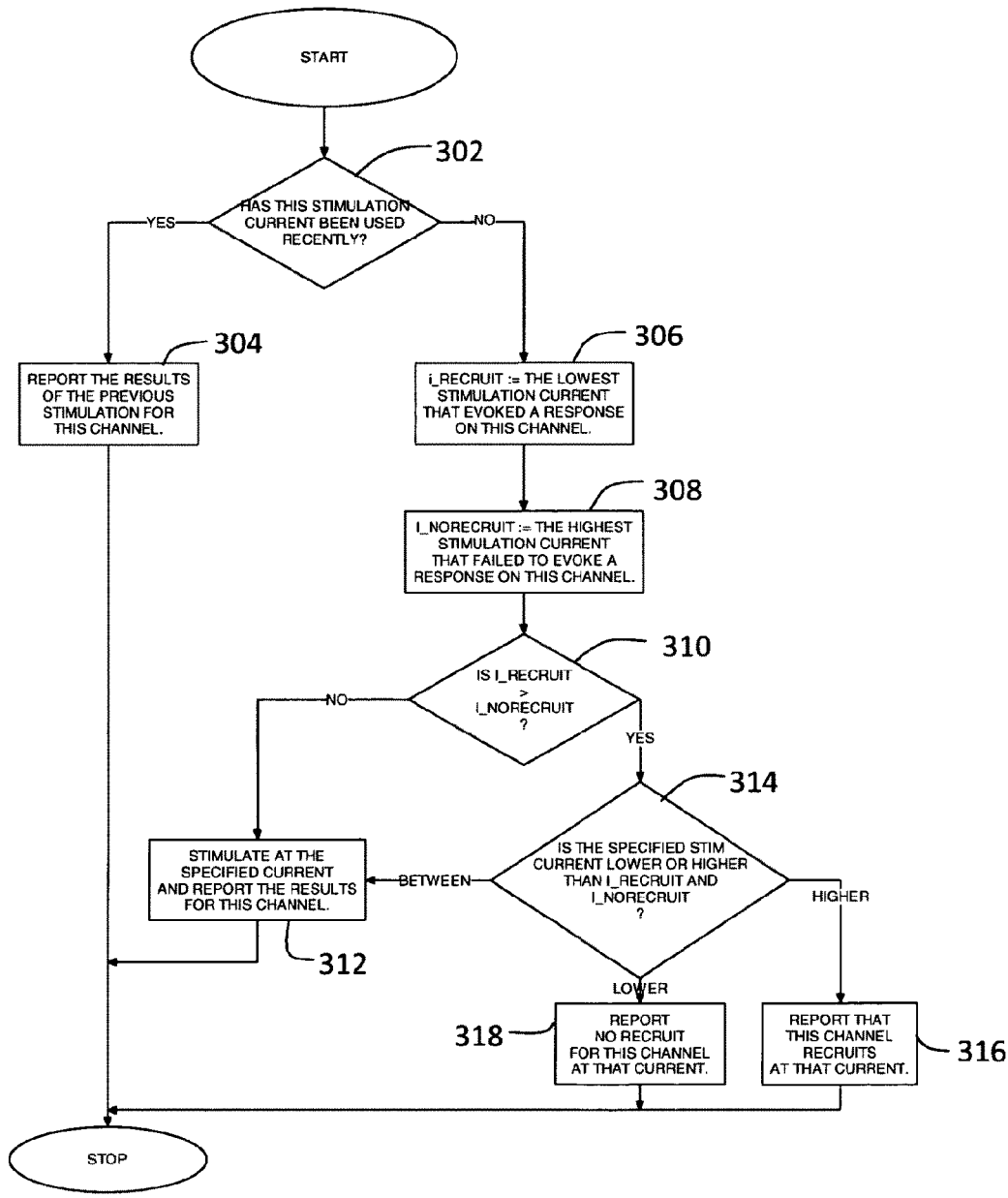
FIG. 34 is a flowchart illustrating the method by which a multi-channel hunting algorithm determines whether to perform or omit a stimulation.

FIG. 34 illustrates (in flowchart form) a method by which the multi-channel threshold hunting algorithm determines whether to stimulate, or not stimulate and simply report previous results. The algorithm first determines if the selected stimulation current has already been used (step 302). If the stimulation current has been used, the stimulation is omitted and the results of the previous stimulation are reported for the present channel (step 304). If the stimulation current has not been used, the algorithm determines $I_{recruit}$ (step 306) and $I_{norecruit}$ (step 308) for the present channel. $I_{recruit}$ is the lowest stimulation current that has recruited on the present channel. $I_{norecruit}$ is the highest stimulation current that has failed to recruit on the present channel. The algorithm next determines whether $I_{recruit}$ is greater than $I_{norecruit}$ (step 310). An $I_{recruit}$ that is not greater than $I_{norecruit}$ is an indication that changes have occurred to $I_{thresh}$ on that channel. Thus, previous results may not be reflective of the present threshold state and the algorithm will not use them to infer the response to a given stimulation current. The algorithm will stimulate at the selected current and report the results for the present channel (step 312). If $I_{recruit}$ is greater than $I_{norecruit}$, the algorithm determines whether the selected stimulation current is higher than $I_{recruit}$, lower than $I_{norecruit}$, or between $I_{recruit}$, and $I_{norecruit}$ (step 314). If the selected stimulation current is higher than $I_{recruit}$, the algorithm omits the stimulation and reports that the present channel recruits at the specified current (step 316). If the selected stimulation current is lower than $I_{norecruit}$, the algorithm infers that the present channel will not recruit at the selected current and reports that result (step 318). If the selected stimulation current falls between $I_{recruit}$ and $I_{norecruit}$, the result of the stimulation cannot be inferred and the algorithm stimulates at the selected current and reports the results for the present channel (step 312). This method may be repeated until $I_{thresh}$ has been determined for every active channel.

In the interest of clarity, FIGS. 35A-35C demonstrate use of the multi-channel threshold hunting algorithm to determine $I_{thresh}$ on only two channels. It should be appreciated, however, that the multi-channel algorithm is not limited to finding $I_{thresh}$ for two channels, but rather it may be used to find $I_{thresh}$ for any number of channels, such as (for example) eight channels according to a preferred embodiment of the neuromonitoring system 10. With reference to FIG. 35A, channel 1 has an $I_{thresh}$ to be found of 6.25 mA and channel 2 has an $I_{thresh}$ to be found of 4.25 mA. $I_{thresh}$ for channel 1 is found first as illustrated in FIG. 35B, using the bracketing and bisection methods discussed above. Bracketing begins at the minimum stimulation current (for the purposes of example only) of 1 mA. As this is the first channel processed and no previous recruitment results exist, no stimulations are omitted. The stimulation current is doubled with each successive stimulation until a significant EMG response is evoked at 8 mA. The initial bracket of 4-8 mA is bisected, using the bisection method described above, until the stimulation threshold, $I_{thresh}$, is contained within a final bracket separated by the selected width or resolution (again 0.25 mA). In this example, the final bracket is 6 mA-6.25 mA. $I_{thresh}$ may be defined as any point within the final bracket or as the midpoint of the final bracket (6.125 mA in this case). In either event, $I_{thresh}$ is selected and reported as $I_{thresh}$ for channel 1.

Once $I_{thresh}$ is found for channel 1, the algorithm turns to channel 2, as illustrated in FIG. 35C. The algorithm begins to process channel 2 by determining the initial bracket, which is again 4-8 mA. All the stimulation currents required in the bracketing state were used in determining $I_{thresh}$ for channel 1. The algorithm refers back to the saved data to determine how channel 1 responded to the previous stimulations. From the saved data, the algorithm may infer that channel 2 will not recruit at stimulation currents of 1, 2, and 4 mA, and will recruit at 8 mA. These stimulations are omitted and the inferred results are displayed. The first bisection stimulation current selected in the bisection process (6 mA in this case), was previously used and, as such, the algorithm may omit the stimulation and report that channel 2 recruits at that stimulation current. The next bisection stimulation current selected (5 mA in this case) has not been previously used and, as such, the algorithm must determine whether the result of a stimulation at 5 mA may still be inferred. In the example shown, $I_{recruit}$ and $I_{norecruit}$ are determined to be 6 mA and 4 mA, respectively. Because 5 mA falls in between $I_{recruit}$ and $I_{norecruit}$, the algorithm may not infer the result from the previous data and, as such, the stimulation may not be omitted. The algorithm then stimulates at 5 mA and reports that the channel recruits. The bracket is reduced to the lower half (making 4.50 mA the next bisection stimulation current). A stimulation current of 4.5 mA has not previously been used and, as such, the algorithm again determines $I_{recruit}$ and $I_{norecruit}$ (5 mA and 4 mA in this case). The selected stimulation current (4.5 mA) falls in between $I_{recruit}$ an $I_{norecruit}$ and, as such, the algorithm stimulates at 4.5 mA and reports the results. The bracket now stands at its final width of 0.25 mA (for the purposes of example only). $I_{thresh}$ may be defined as any point within the final bracket or as the midpoint of the final bracket (4.125 mA in this case). In either event, $I_{thresh}$ is selected and reported as $I_{thresh}$ for channel 2.

Although the multi-channel threshold hunting algorithm is described above as processing channels in numerical order, it will be understood that the actual order in which channels are processed is immaterial. The channel processing order may be biased to yield the highest or lowest threshold first (discussed below) or an arbitrary processing order may be used. Furthermore, it will be understood that it is not necessary to complete the algorithm for one channel before beginning to process the next channel, provided that the intermediate state of the algorithm is retained for each channel. Channels are still processed one at a time. However, the algorithm may cycle between one or more channels, processing as few as one stimulation current for that channel before moving on to the next channel. By way of example only, the algorithm may stimulate at 10 mA while processing a first channel for $I_{thresh}$. Before stimulating at 20 mA (the next stimulation current in the bracketing phase), the algorithm may cycle to any other channel and process it for the 10 mA stimulation current (omitting the stimulation if applicable). Any or all of the channels may be processed this way before returning to the first channel to apply the next stimulation Likewise, the algorithm need not return to the first channel to stimulate at 20 mA, but instead may select a different channel to process first at the 20 mA level. In this manner, the algorithm may advance all channels essentially together and bias the order to find the lower threshold channels first or the higher threshold channels first. By way of example only, the algorithm may stimulate at one current level and process each channel in turn at that level before advancing to the next stimulation current level. The algorithm may continue in this pattern until the channel with the lowest $I_{thresh}$ is bracketed. The algorithm may then process that channel exclusively until $I_{thresh}$ is determined, and then return to processing the other channels one stimulation current level at a time until the channel with the next lowest $I_{thresh\ is}$ bracketed. This process may be repeated until $I_{thresh}$ is determined for each channel in order for of lowest to highest $I_{thresh}$. If $I_{thresh}$ for more than one channel falls within the same bracket, the bracket may be bisected, processing each channel within that bracket in turn until it becomes clear which one has the lowest $I_{thresh}$. If it becomes more advantageous to determine the highest $I_{thresh}$ first, the algorithm may continue in the bracketing state until the bracket is found for every channel and then bisect each channel in descending order.

Figure 36A:
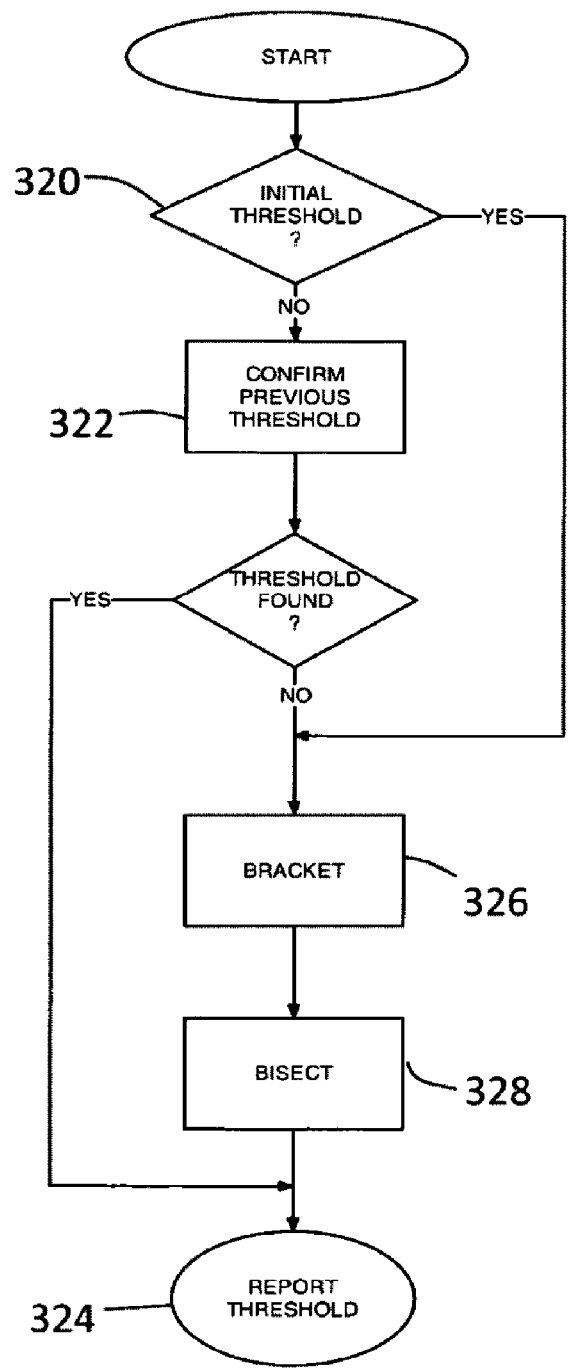
FIG. 36A is a flowchart illustrating the sequence employed by the algorithm to determine and monitor $I_{thresh}$.
Figure 36B:
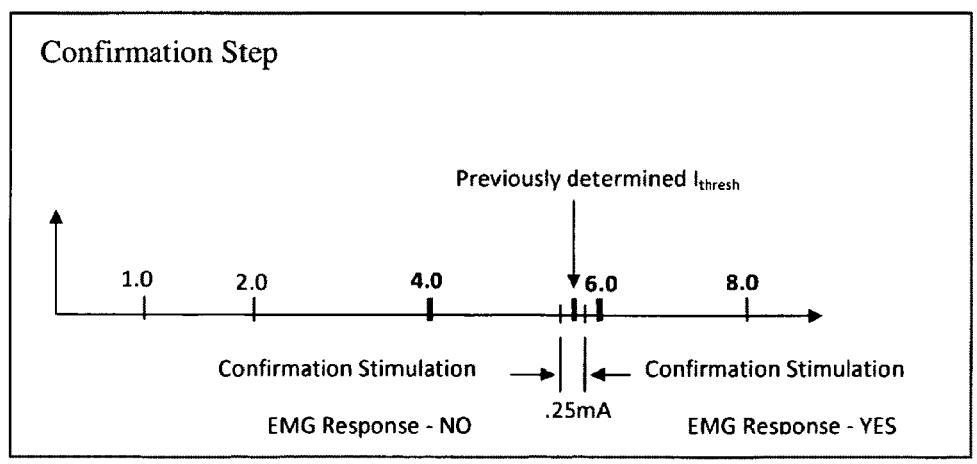
FIG. 36B is a graph illustrating the confirmation step employed by the algorithm to determine whether $I_{thresh}$ has changed from a previous determination.

FIG. 36 illustrates a further feature of the threshold hunting algorithm of the present invention, which advantageously provides the ability to further reduce the number of stimulations required to find $I_{thresh}$ when an $I_{thresh}$ value has previously been determined for a specific channel. In the event that a previous $I_{thresh}$ determination exists for a specific channel, the algorithm may begin by merely confirming the previous $I_{thresh}$ rather than beginning anew with the bracketing and bisection methods. The algorithm first determines whether it is conducting the initial threshold determination for the channel or whether there is a previous $I_{thresh}$ determination (step 320). If it is not the initial determination, the algorithm confirms the previous determination (step 322) as described below. If the previous threshold is confirmed, the algorithm reports that value as the present $I_{thresh}$ (step 324). If it is the initial $I_{thresh}$ determination, or if the previous threshold cannot be confirmed, then the algorithm performs the bracketing function (step 326) and bisection function (step 328) to determine $I_{thresh}$ and then reports the value (step 324).

FIG. 36 illustrates, by way of example only, a method employed by the threshold hunting algorithm for confirming a previous threshold. The confirmation step attempts to ascertain whether $I_{thresh}$ has moved from its last known value. To do this, the algorithm applies two stimulation currents, one at or just above the threshold value and the other just below the threshold value. If the stimulation at or above $I_{thresh}$ recruits and the stimulation just below $I_{thresh}$ does not recruit, then the threshold has not moved and the algorithm may report that value as Fresh and proceed to process another channel. If the stimulation just below $I_{thresh}$ recruits, it may be concluded that $I_{thresh}$ has decreased and likewise if the stimulation at or just above $I_{thresh}$ fails to recruit, it may be concluded that $I_{thresh}$ has increased.

If $I_{thresh}$ cannot be confirmed, the algorithm enters the bracketing state. Rather than beginning the bracketing state from the minimum stimulation current, however, the bracketing state may begin from the previous $I_{thresh}$. The bracketing may advance up or down depending on whether $I_{thresh}$ has increased or decreased. By way of example only, if the previous value of $I_{thresh}$ was 4 mA, the confirmation step may stimulate at 4 mA and 3.75 mA. If the stimulation at 4 mA fails to evoke a significant response, it may be concluded that the $I_{thresh}$ has increased and the algorithm will bracket up from 4 mA. When the algorithm enters the bracketing state, the increment used in the confirmation step (i.e. .25 mA in this example) is doubled. Thus, in this example, the algorithm stimulates at 4.50 mA. If the channel fails to recruit at this current level, the increment is doubled again (1 mA in this example) and the algorithm stimulates at 5.50 mA. This process is repeated until the maximum stimulation current is reached or the channel recruits, at which time the bisection function may be performed. If, during the confirmation step, the stimulation current just below the previously determined $I_{thresh}$ recruits, it may be concluded that $I_{thresh}$ for that channel has decreased and the algorithm may bracket down from that value (3.75 mA in this case). Thus, in this example, the algorithm would double the increment to .50 mA and stimulate at 3.25 mA. If the channel still recruits at this stimulation current, the increment is doubled again to 1 mA such that the algorithm stimulates at 2.25 mA. This process is repeated until the minimum stimulation current is reached or the channel fails to recruit, at which time the algorithm may perform the bisection function. When determining $I_{thresh}$ for multiple channels with previously determined $I_{thresh}$ values, this technique may be performed for each channel, in turn, in any order. Again stimulations may be omitted and the algorithm may begin processing a new channel before completing the algorithm for another channel, as described above.

Although the hunting algorithm is discussed herein in terms of finding $I_{thresh}$ (the lowest stimulation current that evokes a predetermined EMG response), it is contemplated that alternative stimulation thresholds may be useful in assessing the health of the spinal cord or nerve monitoring functions and may be determined by the hunting algorithm. By way of example only, the hunting algorithm may be employed by the system 10 to determine a stimulation voltage threshold, $Vstim_{thresh}$. This is the lowest stimulation voltage (as opposed to the lowest stimulation current) necessary to evoke a significant EMG response, $V_{thresh}$. Bracketing, bisection and monitoring states are conducted as described above for each active channel, with brackets based on voltage being substituted for the current based brackets previously described. Moreover, although described above within the context of MEP monitoring, it will be appreciated that the algorithms described herein may also be used for determining the stimulation threshold (current or voltage) for any other EMG related functions, including but not limited to pedicle integrity (screw test), nerve detection, and nerve root retraction.

The neurophysiology system 10 has been described above according to a preferred embodiment. Nevertheless, various components could be added and/or existing components could be altered without departing from the scope of the invention. Some of these contemplated alterations and/or additions are disclosed hereafter.

Figure 38:
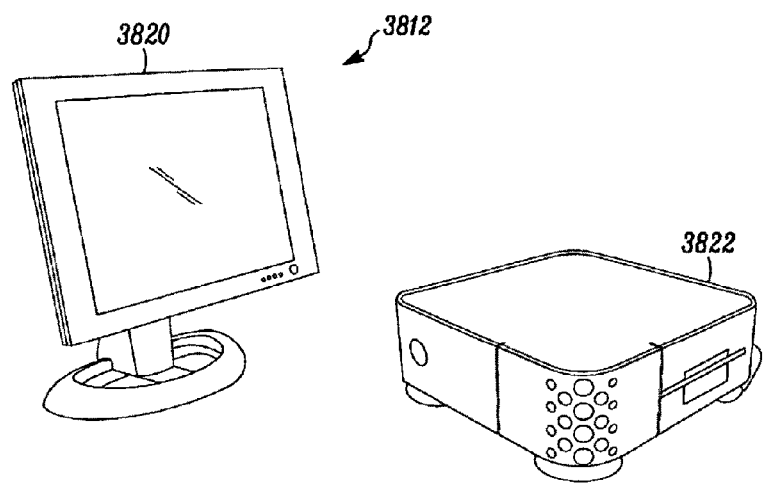
FIG. 38 is a perspective view of an example of a control unit according to an alternate embodiment of the present invention.

FIGS. 38-47 illustrate various example embodiments of the control unit. In FIG. 38 there is shown a control unit 3812 wherein the processing unit 3822 and the main display 3820 are separate devices. Processing unit 3822 and main display 3820 may be linked via wired or wireless technology. Having an uncoupled processing unit 3822 and main display 3820 may add flexibility to the neurophysiology system 10 in that the individual components may be maintained, upgraded, shipped, or replaced, as needed.

Figures 39A, 39B, 39C:
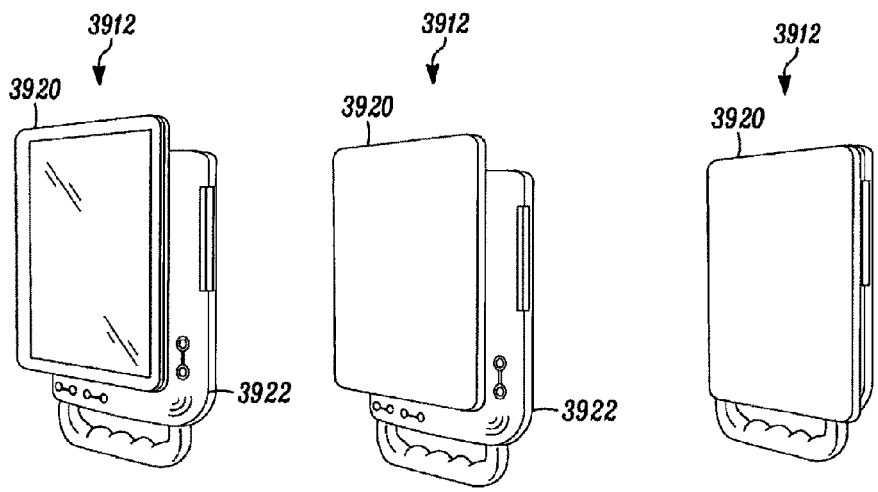
FIGS. 39A-39C are a perspective view of an example of a control unit according to a another alternate embodiment of the present invention.

FIGS. 39A-39C illustrate a control unit 3912 wherein the processing unit 3922 and display 3920 are integrated in a single device. Main display 3920 may be attached to processing unit 3922 such that it may rotate from an open position (FIG. 39A) to a closed position (FIG. 39C). The closed position may help protect the screen from damage when not in use. A built-in handle may be provided for simplified travel of the control unit 3912. A wireless antenna may be provided inside the handle to assist in wireless communication with other components of the neurophysiology system 10 while limiting the profile of the main bodies of the display 3920 and processing unit 3922. The control unit 3912 may be configured to mount on a pole stand, similar to that shown in FIG. 41, or an operating light, similar to that shown in FIG. 42. The control unit 3912 may also be configured to mount on various other OR objects including, but not necessarily limited to, an IV pole, bed, table, etc . . . ). The touch screen of main display 3920 may be replaced with buttons for inputting user controls. Alternatively, buttons may be used for inputting user controls in addition to the touch screen.

Figure 40:
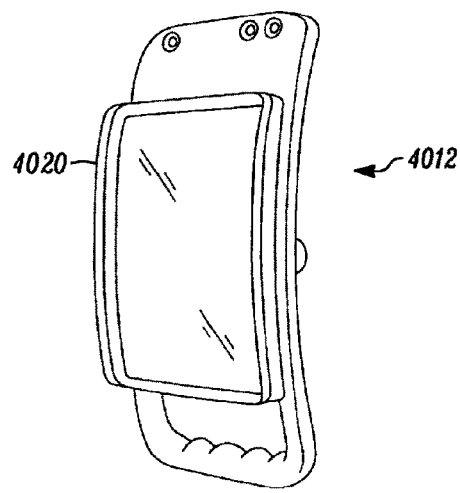
FIGS. 40-42 are perspective views a perspective view of an example of a control unit according to an alternate embodiment of the present invention
Figure 41:
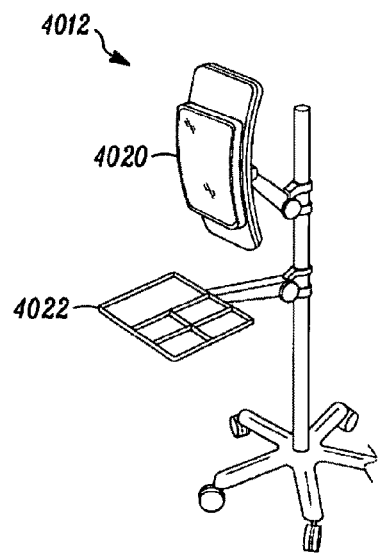
Figure 42:
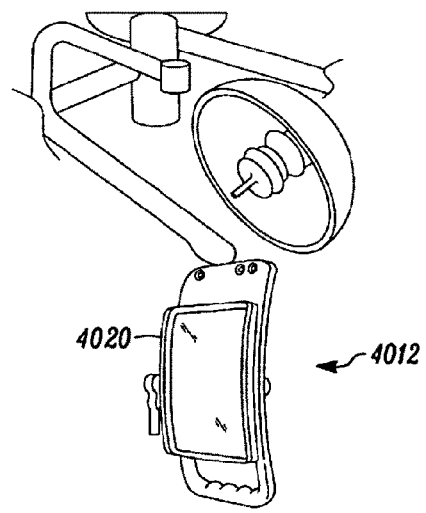

FIG. 40 illustrates a control unit 4012 similar to the control unit shown in FIGS. 39A-39C, but smaller. A built-in handle may be provided for simplified travel of the control unit 4012. A wireless antenna may be provided inside the handle to assist in wireless communication with other components of the neurophysiology system 10 while limiting the profile of the control unit 4012. The control unit 4012 may be configured to mount on a pole stand, as in FIG. 41, or an operating light as in FIG. 42. The control unit 4012 may also be configured to mount on various other OR objects including, but not necessarily limited to, an IV pole, bed, table, etc . . . ). FIG. 41 also shows a disposables tray 4022 for holding and organizing disposables (e.g. electrodes, probes, etc . . . ) used with the system 10. The tray 4022 may preferably be mounted just below the control unit 4012 such that the display may provide instructions for use of the disposables (e.g. electrode placement, probe attachment, etc . . . ) that point directly to the disposables in the tray. The touch screen of main display 4020 may be replaced with buttons for inputting user controls. Alternatively, buttons may be used for inputting user controls in addition to the touch screen. It is also contemplated that the control unit 4012 may be used only as a main display 4020 and may be connected to a separate processing unit 4022, such as that shown in FIG. 38.

Figure 43:
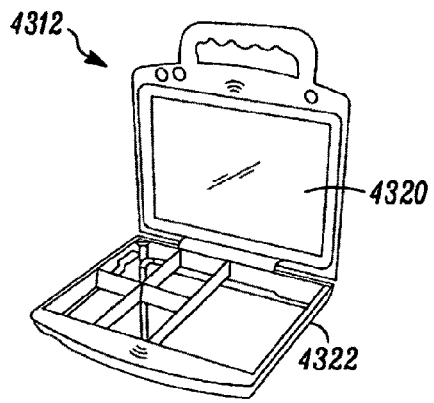
FIGS. 43-44 are perspective views of an example of a control unit according to yet another alternate embodiment of the present invention.
Figure 44:
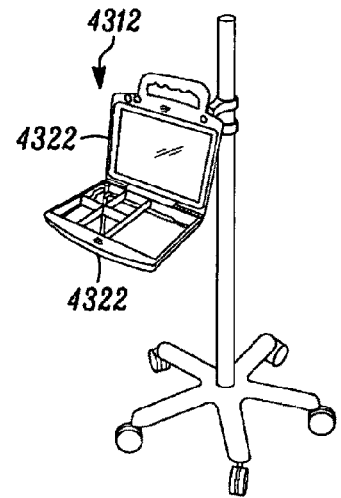

FIG. 43 illustrates an example of a control unit 4312 exhibiting a clamshell shape. The clamshell allows the control unit 4312 to be quickly and easily closed and protected for movement. In the open position, the bottom portion of the clamshell may include a tray 4322 for holding and organizing disposables (e.g. electrodes, probes, etc . . . ) used with the system 10. The display 4320 may provide instructions for use of the disposables (e.g. electrode placement, probe attachment, etc . . . ) that point directly to the disposables in the tray 4322. A built-in handle may be provided and the handle may include a wireless antenna to assist in wireless communication with other components of the neurophysiology system 10.

Figure 45:
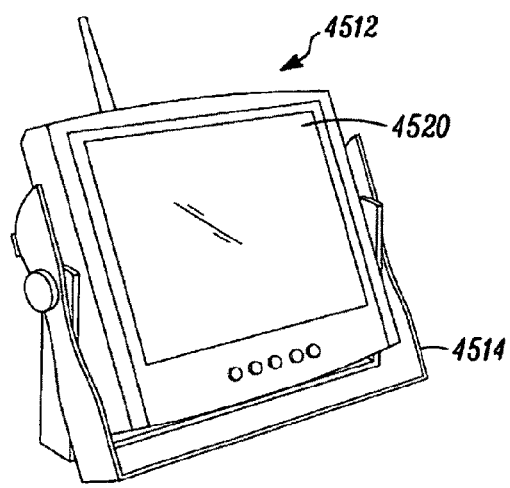
FIGS. 45-47 are perspective views of an example of a control unit according to still yet another alternate embodiment of the present invention.
Figure 46:
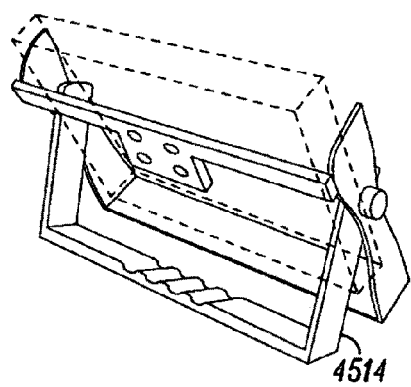
Figure 47:
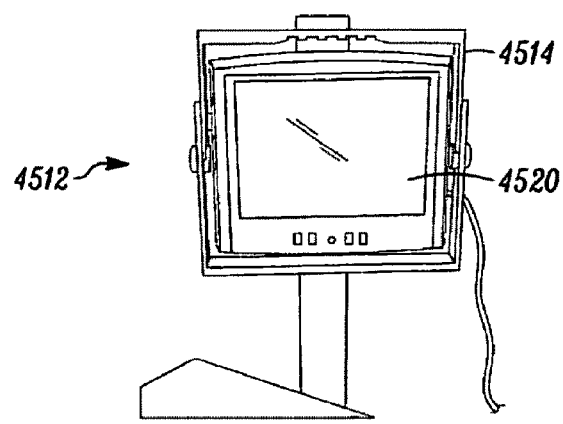

FIG. 45 shows yet another example embodiment of a control unit 4512. The control unit 4512 may be configured to engage with a bracket 4514 shown in FIG. 46. The bracket 4514 may be used as a stand as shown in FIG. 45, or the bracket may be mounted to various objects in the OR, such as for example, the pole illustrated in FIG. 47. An integrated wireless antenna may be provided to assist in wireless communication with other components of the neurophysiology system 10 and is viewable in FIG. 45. The touch screen of main display 4520 may be replaced with buttons for inputting user controls. Alternatively, buttons may be used for inputting user controls in addition to the touch screen. It is also contemplated that the control unit 4512 may be used only as a main display 4520 and may be connected to a separate processing unit 4522, such as that shown in FIG. 38.

Figure 48:
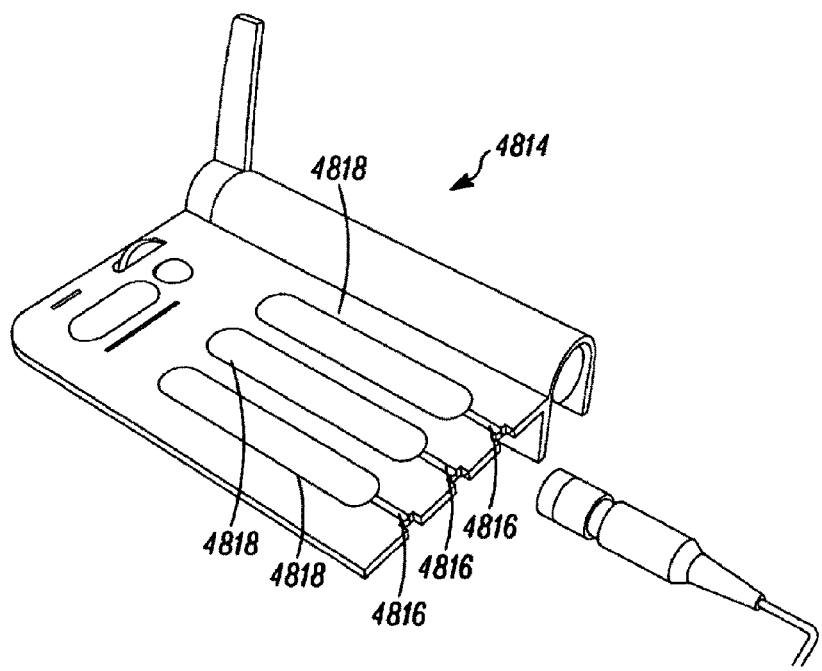
FIG. 48 is a perspective view of a hub device that may be used with the neurophysiology system of FIG. 1.

One embodiment of a patient module 4814 is illustrated in FIG. 48. The patient module 14 includes multiple electrode input connections 4816 for linking several electrode harnesses at once. This way electrode coverage may be obtained over different parts of the body (e.g. arms, legs, head, and trunk) without changing connections. The patient module 4814 may be configured to conduct impedance testing of attached electrodes. The electrode connections may be tested individually or en masse. Buttons may be provided on the patient module 14 to receive user input, such as for example only, to conduct the impedance test on a specific electrode or all electrodes. One or more display windows 4818 may also be provided which may act as a secondary feedback device. Procedure data including, but not necessarily limited to, a stimulation threshold result, current stimulation level, selected function, etc . . . may be viewed on the patient module 4814, which may be positioned closer to the user than the main display. The display window may also display patient module specific data, such as, by way of example only, the number of electrodes or electrode harnesses attached, the number of hubs attached, and impedance data. The patient module 4814 may contain a wireless antenna to assist in wireless communication with the control unit 12 and other components of the neurophysiology system 10. By way of example only, the electrodes and/or stimulation accessories may be configured as standalone devices that communicate with the patient module through wireless communication.

Figure 49A:
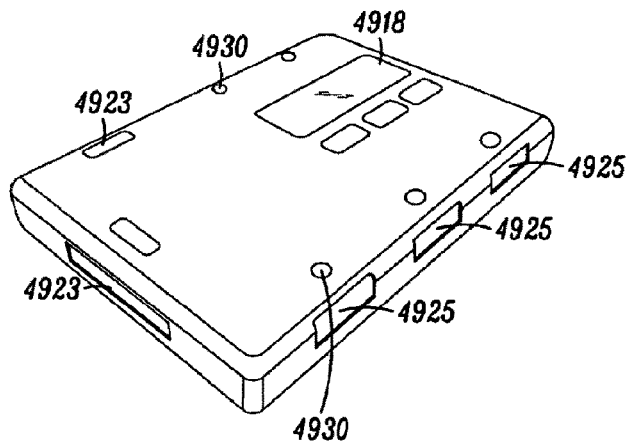
FIGS. 49A-49B are perspective and side views of an example of a hub that may be used with the neurophysiology system of FIG. 1, according to an alternate embodiment of the present invention.
Figure 49B:
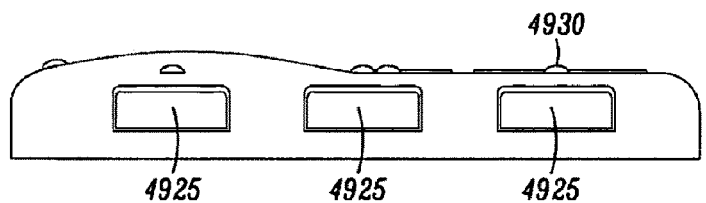
Figure 50:
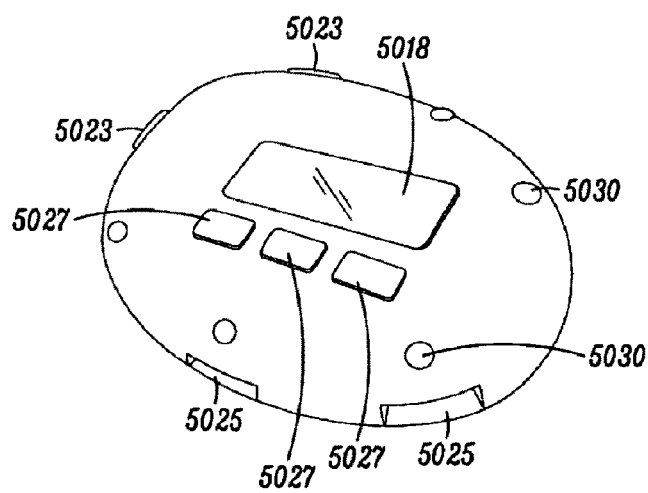
FIG. 50 is a perspective view of an example of a hub that may be used with the neurophysiology system of FIG. 1, according to another alternate embodiment of the present invention.

FIGS. 49A-49B illustrate another example embodiment of a patient module 4914 and FIG. 50 illustrates yet another example embodiment of the patient module 5014. The patient module 4914, 5014 includes multiple electrode input connections 4925, 5025 for linking several electrode harnesses at once. This way electrode coverage may be obtained over different parts of the body (e.g. arms, legs, head, and trunk) without changing connections. Additional connection ports are provided for stimulation accessories 4923, 5023 as well. The patient module 4914, 5014 may be configured to conduct impedance testing of attached electrodes. The electrode connections may be tested individually or en masse. Buttons 5027 may be provided on the patient module 4914, 5014 to receive user input, such as for example only, to conduct the impedance test on a specific electrode or all electrodes. One or more display windows 4918, 5018 may also be provided which may act as a secondary feedback device. Procedure specific data, including, but not necessarily limited to, a stimulation threshold result, current stimulation level, selected function, etc . . . may be viewed on the patient module 4914, 5014, which may be positioned closer to the user than the main display. The display window 4918, 5018 may also display patient module specific data, such as, by way of example only, the number of electrodes or electrode harnesses attached, the number of hubs attached, the surgical accessory attached, and impedance data. LED lights 4930, 5030 may also be dispersed about the patient module to indicate the status of electrodes and/or surgical accessories attached. The shape of the LED may vary depending upon the function of the port plug associated with it. By way of example only, the LED may be circular for electrode connections and rectangular for plugs equipped to deliver stimulation (e.g. for stimulation accessory connection or connection of a hub). The patient module may contain a wireless antenna to assist in wireless communication with the control unit 12 and other components of the neurophysiology system 10. By way of example only, the electrodes and/or stimulation accessories may be configured as standalone devices that communicate with the patient module through wireless communication.

The patient module 4914, 5014 is preferably positioned outside of the surgical field but close enough so that all electrode connections can be made without tension on the wires, should a wired connection be used. Optionally, one or more hub stations (hubs) 5124 may be communicatively linked to the patient module 14 and are provided for placement inside the surgical field and/or at the opposite end of the patient from the patient module 14. The addition of hubs 5124 may reduce the presence of wires in wired system or partially wired systems. By way of example only, the patient module 14 may be placed on the edge of the bed near the patient's feet. A wired electrode harness may be connected to the module 14 and individual electrodes may be dispersed over the muscles of the legs. A hub 5124 may be wirelessly connected to the patient module 14 and positioned near the patient's head. Another wired electrode harness may be connected to the hub 5124 and stimulation and/or recoding electrodes may be dispersed over the patient's head (e.g. for MEP and SSEP monitoring). A second hub may be provided and wirelessly connected to the patient module 14. The second hub may be placed near the stimulation site and a stimulation accessory may be connected to it via a wire.

Figure 51A:
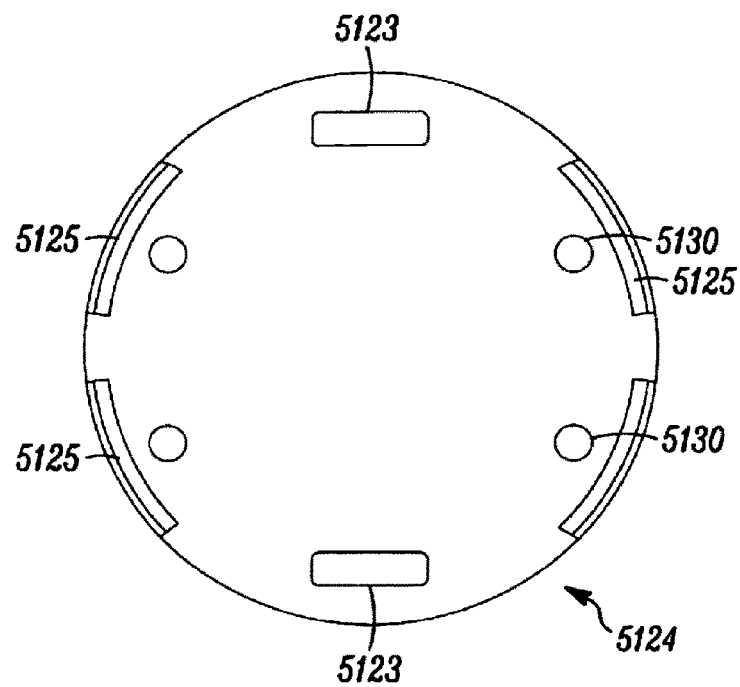
FIGS. 51A-51B are top and side views of an example of a hub that may be used with the neurophysiology system of FIG. 1, according to still another alternate embodiment of the present invention.
Figure 51B:
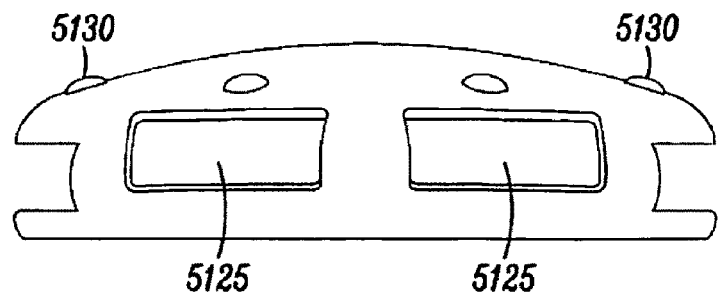

FIGS. 51A-51B depict one example embodiment of a hub 5124. The hub 5124 may be generally smaller than the patient module and has substantially rounded edges to allow placement near the patient. The hub contains a stimulation source such that it may be used to connect stimulation accessories as well as electrodes. Multiple connection ports are provided for both electrode connection and stimulation accessory connection. LED lights 5130 may also be dispersed about the hub 5124 to indicate the status of electrodes and/or surgical accessories attached at connection ports corresponding to the LED lights. The shape of the LED 5130 may vary depending upon the function of the port plug associated with it. By way of example only, the LED may be circular for electrode connections and rectangular for plugs equipped to deliver stimulation (e.g. for stimulation accessory connection or connection of a patient module). The hub 5124 may contain a wireless antenna to assist in wireless communication with the patient module 24 and other components of the neurophysiology system 10.

Figure 52:
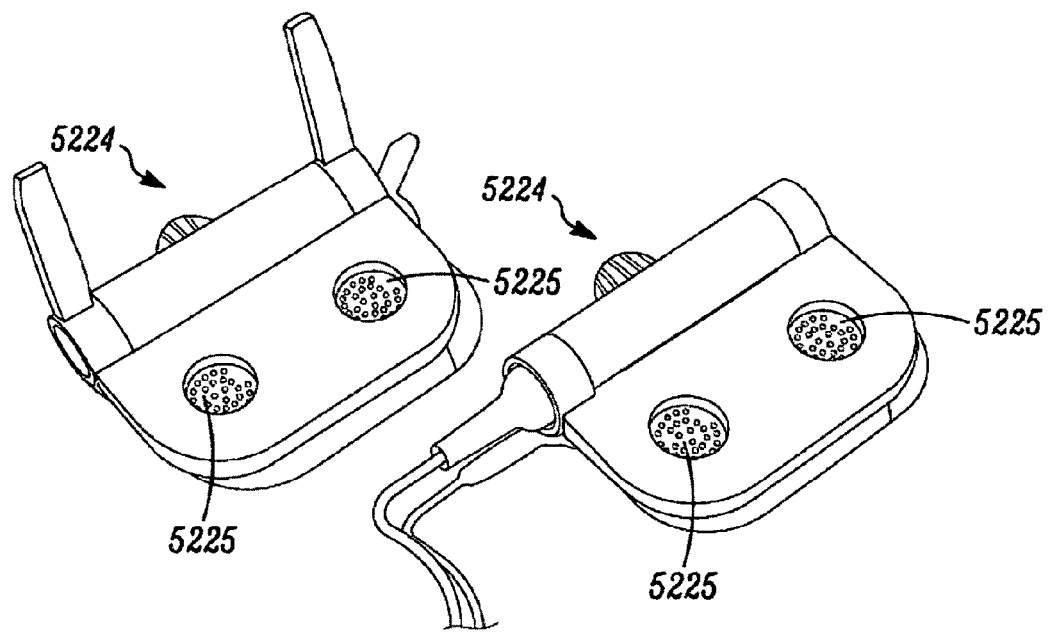
FIG. 52 is a perspective view of an example of a pair of hubs that may be used with the neurophysiology system of FIG. 1, according to yet one more alternate embodiment of the present invention.

FIG. 52 illustrates another example embodiment of the hub 5214. The hub 5224 may be generally smaller than the patient module 5214 and has substantially rounded edges to allow placement near the patient. Multiple connection ports 5225 are again provided for both electrode connection and stimulation accessory connection. The hub 5224 may contain a wireless antenna to assist in wireless communication with the patient module 5224 and other components of the neurophysiology system 10.

Figure 53A:
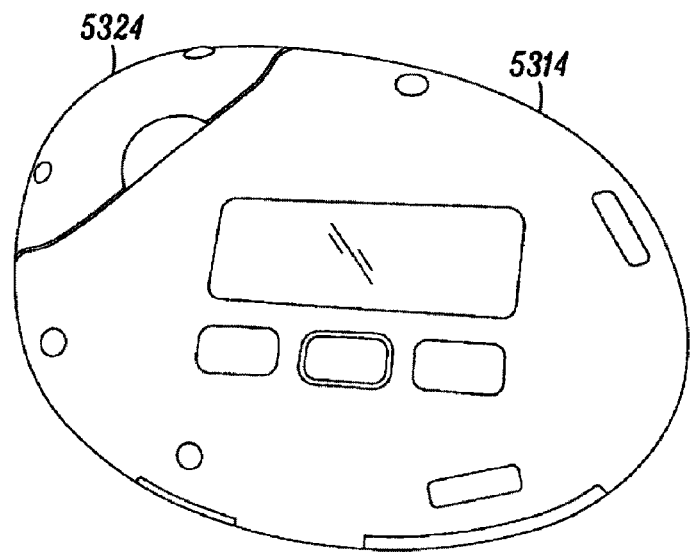
FIGS. 53A-53B are perspective views of a patient module and hub combination that may be used with the neurophysiology system of FIG. 1, according to an alternate embodiment of the present invention.
Figure 53B:
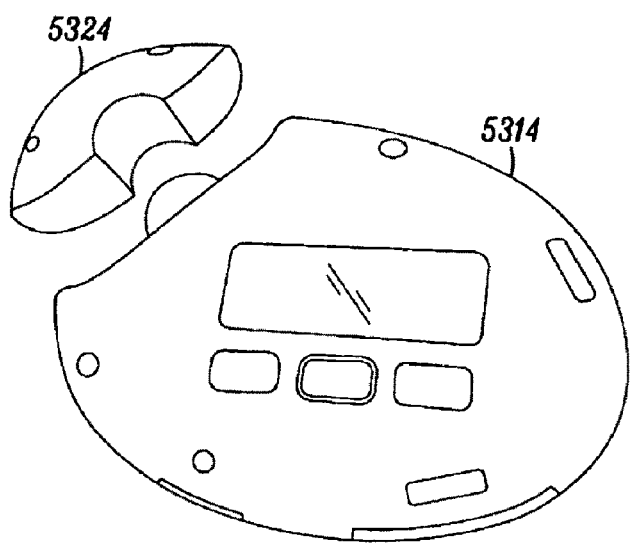
Figure 54:
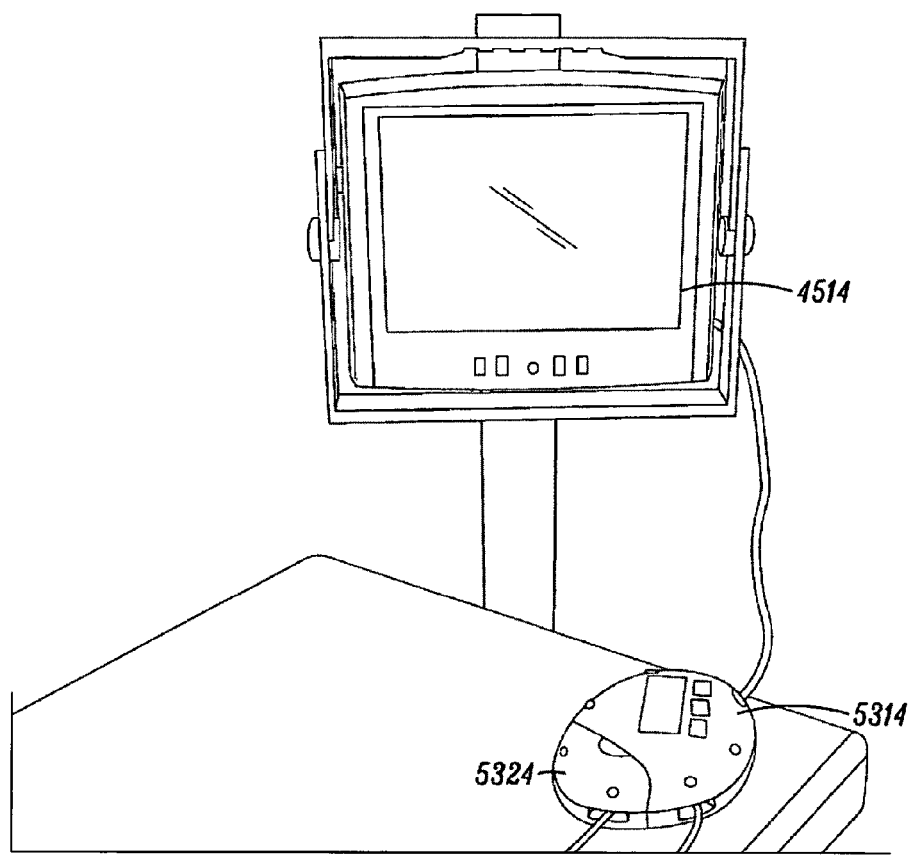
FIG. 54 is a perspective view of the hub and patient module combination of FIGS. 53A-53B in use with the control unit of FIG. 47; according to an alternate embodiment of the present invention.

FIGS. 53A-53B illustrate an embodiment of a patient module 5314 with a detachable hub 5324. The combined patient module/hub combines all the features of the above described patient modules and hubs into a single device. In use, the detachable hub 5324 can be detached from the patient module 5314 and placed within the surgical field closer to a desired position. FIG. 19 depicts the combined patient module/hub connected to the control unit 4512 of FIG. 45.

Figure 55:
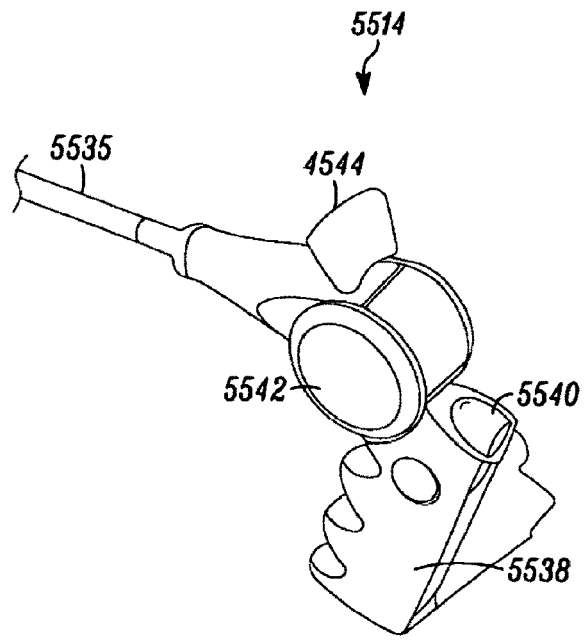
FIGS. 55-56 are perspective views of a stimulation probe that may be used with the neurophysiology system of FIG. 1, according to an alternate embodiment of the present invention.
Figure 56:
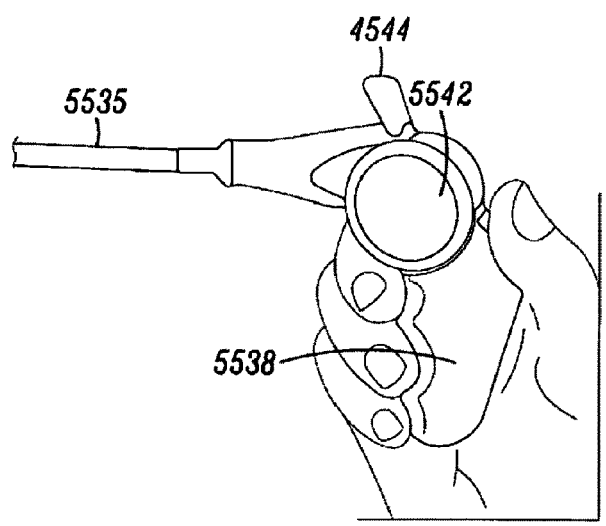

The neurophysiology system 10 utilizes stimulation accessories to deliver stimulation signals to the stimulation target site. The stimulation accessories may be in the form of various probe devices that are themselves inserted to the stimulation site, clips that attach to and deliver stimulation signals to standard instruments that are used at various times throughout a procedure (e.g. pedicle access needle, tap, dilators, tissue retractor, etc . . . ), and surface electrodes. FIG. 55 depicts one embodiment of a stimulation accessory 5514. The stimulation probe 5514 shown is designed to deliver a stimulation signal to a site within the patient. The probe tip 5535 may be interchangeable between various tips. By way of example, the tip may comprise a probe member that is advancable to the stimulation target site, or the tip may comprise a wire with a clip on the end (not shown) for attaching to a standard surgical instrument. A button 5540 at the thumb allows the stimulation current to be easily turned on and off. An additional button may be provided on the handle to toggle between different modes of the neurophysiology system 10. The probe handle 5538 includes finger indentations to increase comfort and grip as seen in FIG. 56. The probe handle is useable by both left-handed and right-handed users. The angle of the handle relative to the probe tip may be adjustable allowing individual users to select the most comfortable and appropriate position. To accomplish this, the probe handle 5538 includes an adjustable wheel 5542 between distal and proximal ends. The probe tip 5535 is preferably disposable and the probe handle 5538 is preferably reusable. The disposable probe tip 5535 may be attached to the probe handle 5538 via any suitable attachment mechanism. By way of example, a "push in and twist" mechanism may be used to allow for quick installation of the tips. The probe may be connected to the patient module 5114 or hub 5124 via wired or wireless technology. For wireless technology the probe handle includes a wireless antenna. Rechargeable batteries may be provided to power the stimulation signals. The probe handle may be further configured to receive and display results and/or other data from the neurophysiology system 10. By way of example, the probe handle may include a backless LCD display 5544, which is effectively transparent for viewing data without obscuring the user's view of the patient.

Figure 57:
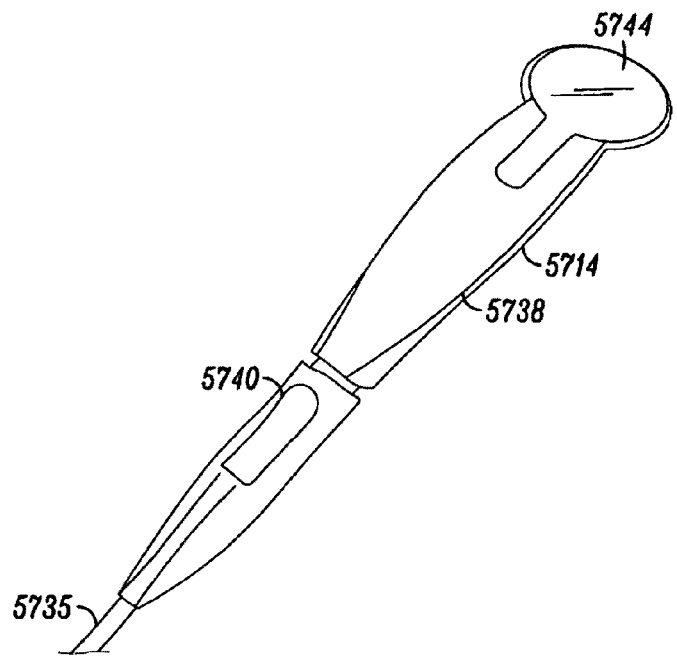
FIGS. 57-58 are perspective views of a pair of stimulation probes that may be used with the neurophysiology system of FIG. 1, according to another alternate embodiment of the present invention.
Figure 58:
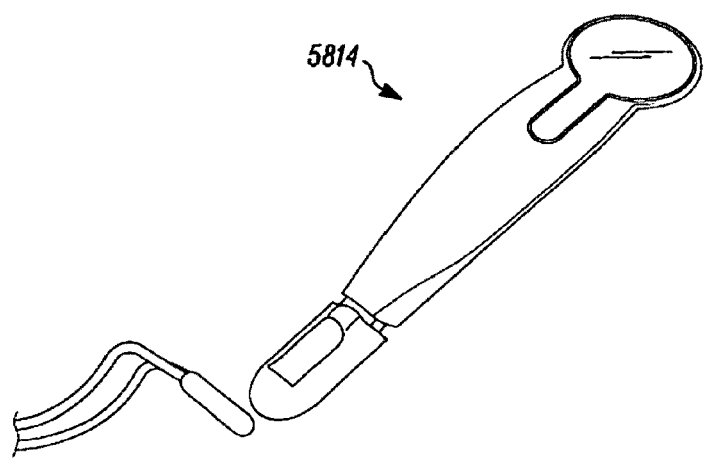
Figure 59A:
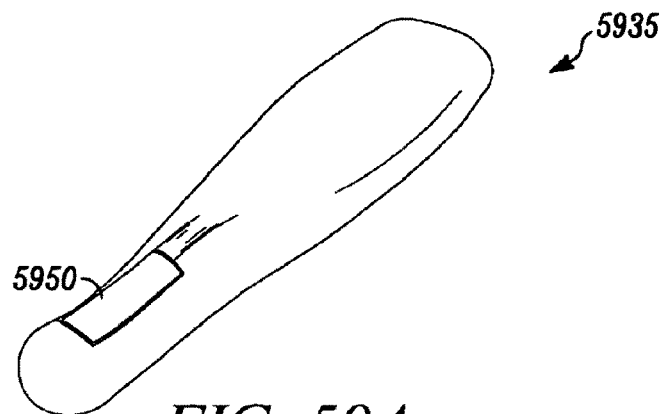
FIGS. 59A-59C are perspective, top, and side views of a probe handle that may be attached to a probe and used with the neurophysiology system of FIG. 1, according to an alternate embodiment of the present invention.
Figure 59B:
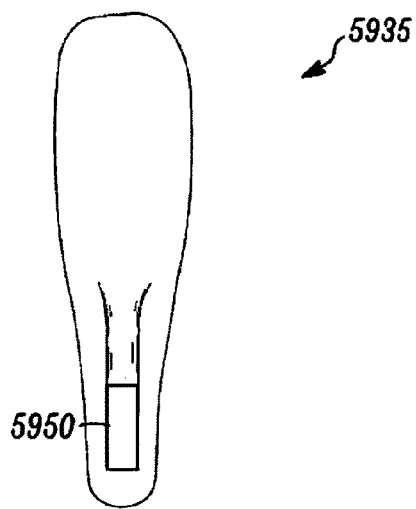
Figure 59C:
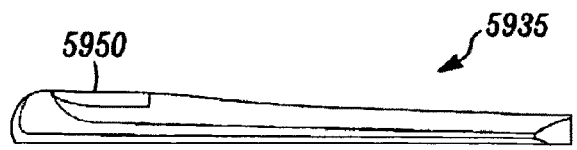

FIGS. 57-58 illustrate another embodiment of a stimulation accessory 5714, 5814. Both the probe handle 5738 and the probe tip 5735 may be disposable. The probe tip 5735 may be interchangeable between various tips. By way of example, the tip may comprise a probe member that is advancable to the stimulation target site, or the tip may comprise a wire with a clip on the end (not shown) for attaching to a standard surgical instrument. The probe tip may include an integrated button 5740 for control of the stimulation signal. The probe handle may include a wireless display 5744 for receiving and displaying results and/or other data from the neurophysiology system 10. The display may be hinged to allow the display to be seen whether the probe is positioned vertically or horizontally. The shape of the probe allows it to be held comfortably or rested on a flat surface such as, for example, the bed or table, without moving if the button is pressed from above.

FIGS. 59-65 illustrate various other example embodiments of probe handles that may be fitted with probe tips to form stimulation accessories. The embodiment of the probe handle 5935 shown in FIGS. 59A-59C is similar to that shown in FIGS. 57-58. The probe handle may include an integrated button 5950 for control of the stimulation signal. The shape of the probe allows it to be held comfortably or rested on a flat surface such as, for example, the bed or table, without moving if the button is pressed from above.

Figure 60A:
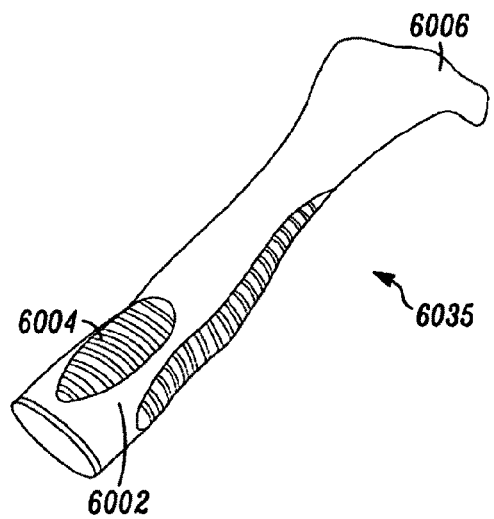
FIGS. 60A-60C are perspective, top, and side views of a probe handle that may be attached to a probe and used with the neurophysiology system of FIG. 1, according to another alternate embodiment of the present invention.
Figure 60B:
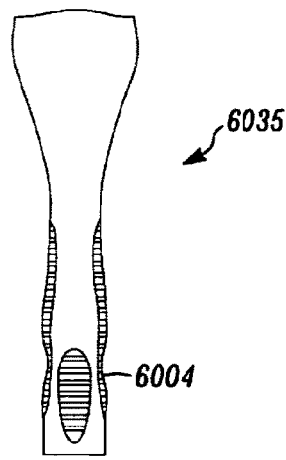
Figure 60C:
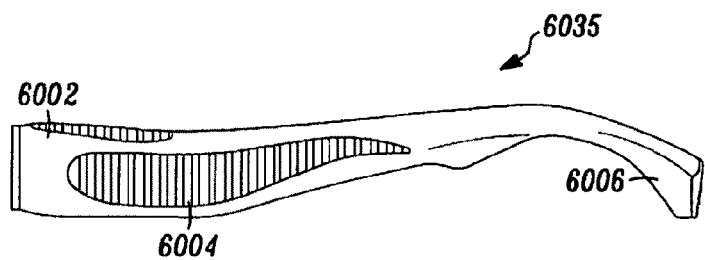

The probe handle 6035 shown, by way of example only, in FIGS. 60A-60C includes a front portion 6002 with an ergonomically designed grip 6004 and a tail portion 6006. The front portion is outfitted with textured material to enhance the grip even further. A stimulation button is provided for controlling stimulation. The tail portion forms a hook like structure, which steadies the probe and allows the button to be pressed from above while the probe is rested on a flat surface.

Figure 61A:
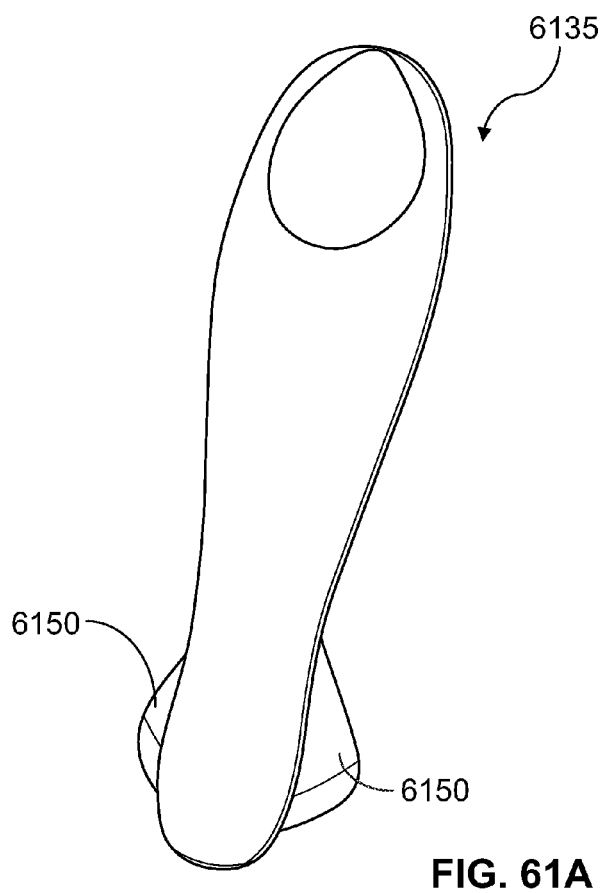
FIGS. 61A-61B are perspective and side views of a probe handle that may be attached to a probe and used with the neurophysiology system of FIG. 1, according to still another alternate embodiment of the present invention.
Figure 61B:
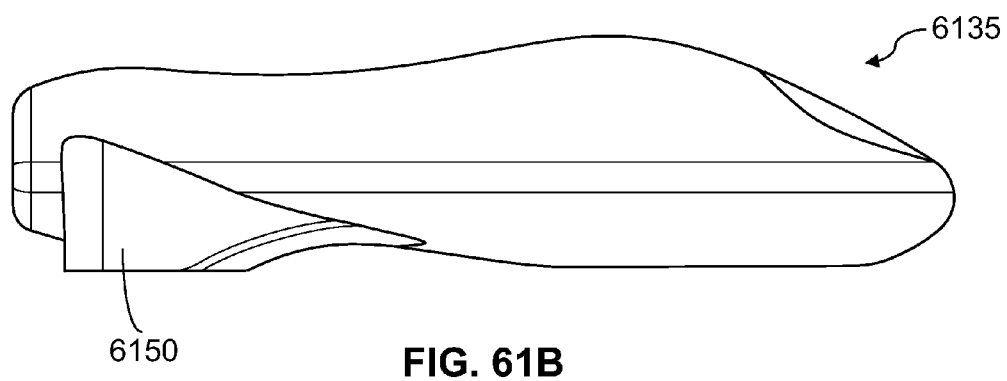

The probe handle 6135 shown, by way of example only, in FIGS. 61A-61B is designed to allow the user to maintain a neutral hand position (palm facing inward) during use. A thumb button is provided and positioned at an angle to correspond to the natural motion of the thumb when a first is made in the neutral position. The thumb button may be used to control the stimulation. The flat back of the probe allows it to be used while it is lying on the table. That is, the flat back steadies the probe while it is lying on the table such that the button may be pushed without the probe moving.

Figure 62A:
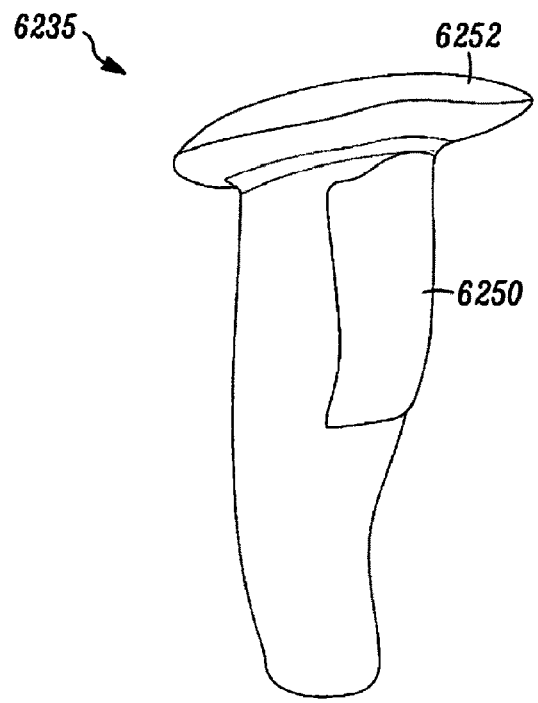
FIGS. 62A-62B are perspective and side views of a probe handle that may be attached to a probe and used with the neurophysiology system of FIG. 1, according to still one more alternate embodiment of the present invention.
Figure 62B:
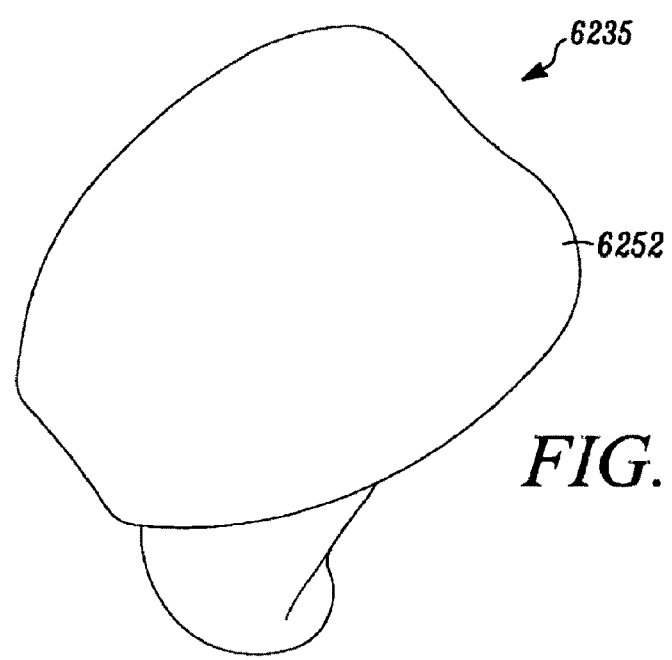

An example embodiment of a joystick probe handle 6235 is illustrated in FIGS. 62A-62B. The joystick design allows the handle to be manipulated from a neutral hand position. A rim 6252 is provided at the top of the handle to prevent downward slippage during use. A large stimulation button 6250 is provided on the front of the probe handle for controlling stimulation. The button 6250 is provided such that it may be utilized by squeezing of the hand. The probe handle has a generally flat back, which allows it to be used while it is lying on the table.

Figure 63A:
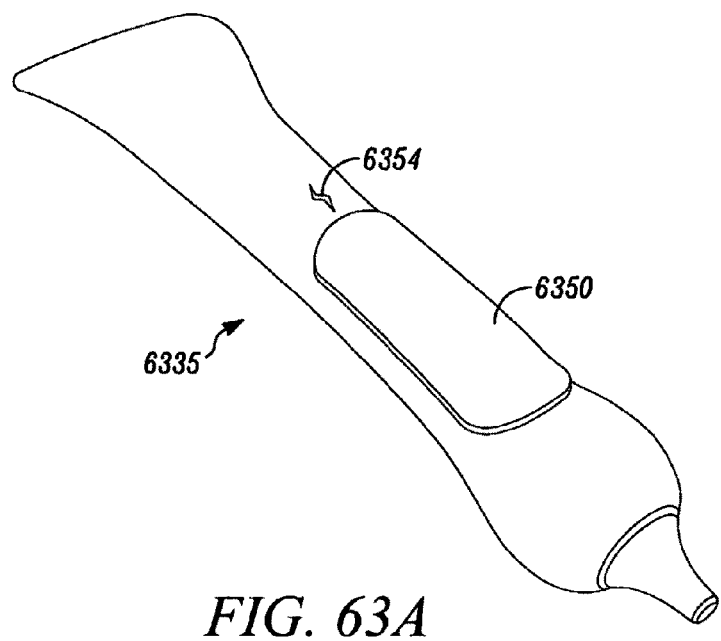
FIGS. 63A-63C are perspective, top, and side views of a probe handle that may be attached to a probe and used with the neurophysiology system of FIG. 1, according still yet another alternate embodiment of the present invention.
Figure 63B:
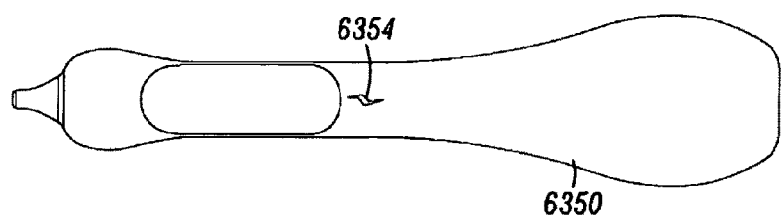
Figure 63C:
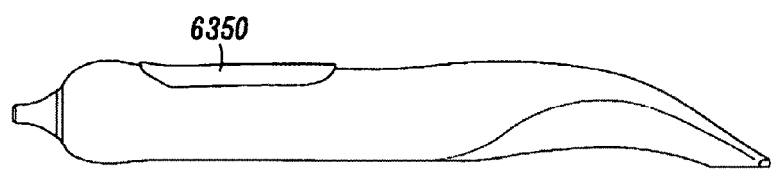

Yet another ergonomic probe handle is illustrated, by way of example only in FIGS. 63A-63C. The probe handle 6335 has a large button 6350 for controlling stimulation. When the neurophysiology system 10 is activated a light on or near the button lights up 6354 to indicate the readiness of the probe to deliver a stimulation current. The hook design at the tail end of the probe allows it to be used while it is lying on the table. A receptacle may be provided on the tail end for receiving a wire connector of an electric coupling device. This allows a probe tip and a separate electric coupling device to be attached to the probe handle at the same time, alleviating the need to switch probe tips.

Figure 64A:
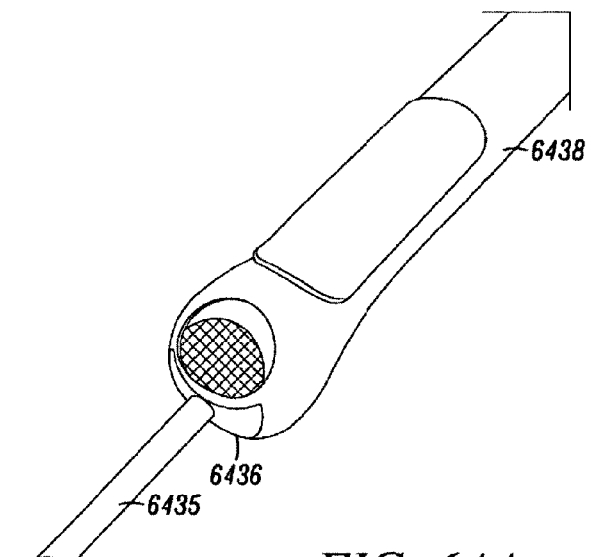
FIGS. 64A-64C are perspective, top, and side views of a probe handle with a removable probe that may be used with the neurophysiology system of FIG. 1, according to an alternate embodiment of the present invention.
Figure 64B:
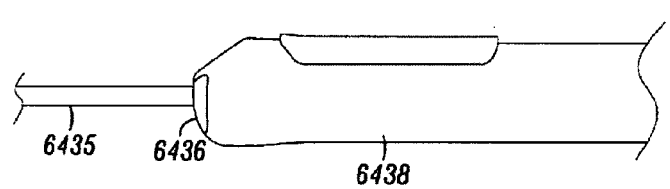
Figure 64C:
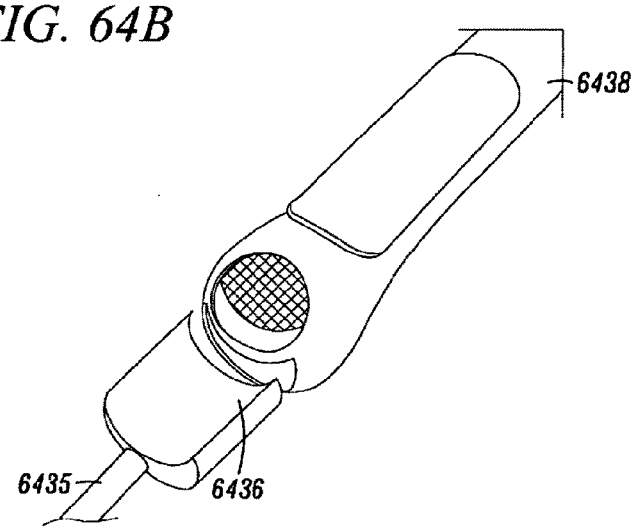
Figure 65A:
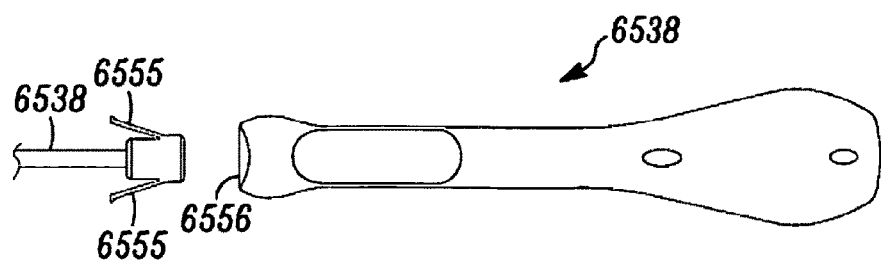
FIGS. 65A-65D are side and perspective views of a probe handle and a removable probe that may be used with the neurophysiology system of FIG. 1, according to an another alternative embodiment of the present invention.
Figure 65B:
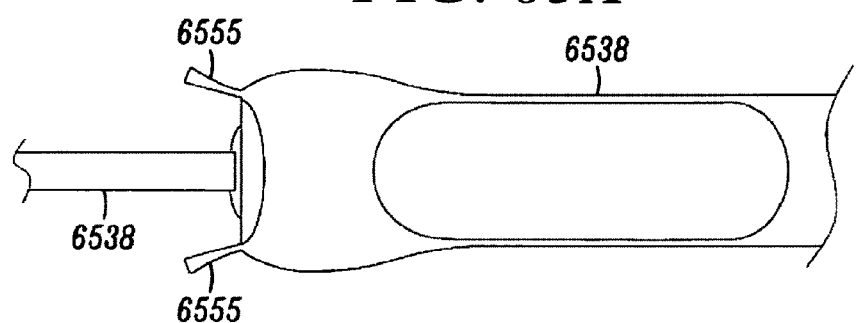
Figure 65C:
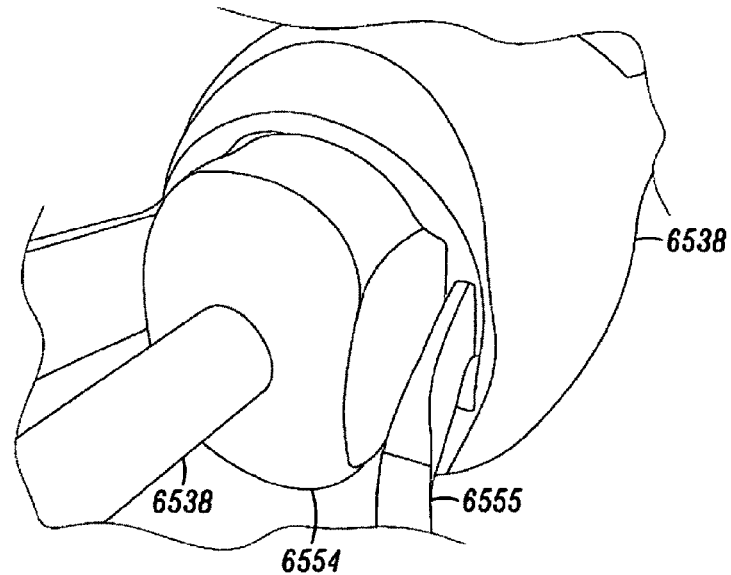
Figure 65D:
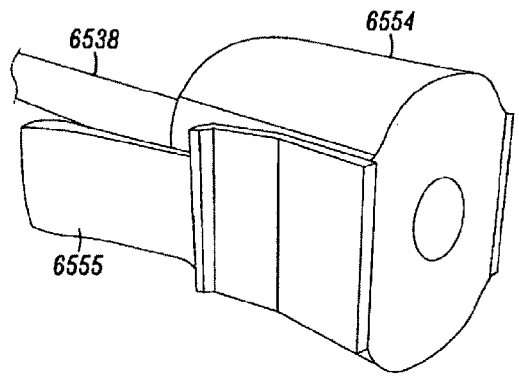

FIGS. 64-65 demonstrate example embodiments of probe tips that may be utilized with various probe handles, such as, by way of example only, those probe handles shown in FIGS. 59-63. FIGS. 64A-64B illustrate a probe tip 6435 with a mating body 6436 dimensioned for receipt in a mating aperture of the probe handle 6438. The mating aperture includes a spring-loaded mechanism that automatically locks the probe tip in place when it is inserted. To release the probe tip, a release switch may be manipulated with the thumb while the probe tip is pulled out. FIGS. 65A-65D, illustrate a probe tip 6538 that employs a locking mechanism based on the elastic properties of wings 6555 provided on the mating body 6554. The wings 6555 deflect inward as the mating body 6554 is inserted into the mating aperture 6556. When the mating body 6554 is fully inserted the wings 6555 snap back to their natural position, locking the probe tip in place. To release the probe, pressure may be applied to both wings 6555 and the probe tip pulled out. In each of the above described example embodiments, the probe tip may comprise a number of different types, including but not necessarily limited to, a ball tipped probe, a nerve retractor, and an electric coupling device for attaching to standard surgical instruments.

Attaching an electric coupling device to the neurophysiology system 10, either directly or via a probe handle, allows the neurophysiologic assessments performed by the system 10 to be conducted through various surgical instruments used during a surgical procedure. By way of example only, the coupling device may connect instruments including, but not necessarily limited to, a tap, dilator, tissue retractor, and k-wire, to the neurophysiology system 10. Various example embodiments of electric coupling devices will now be described.

Figures 66, 67:
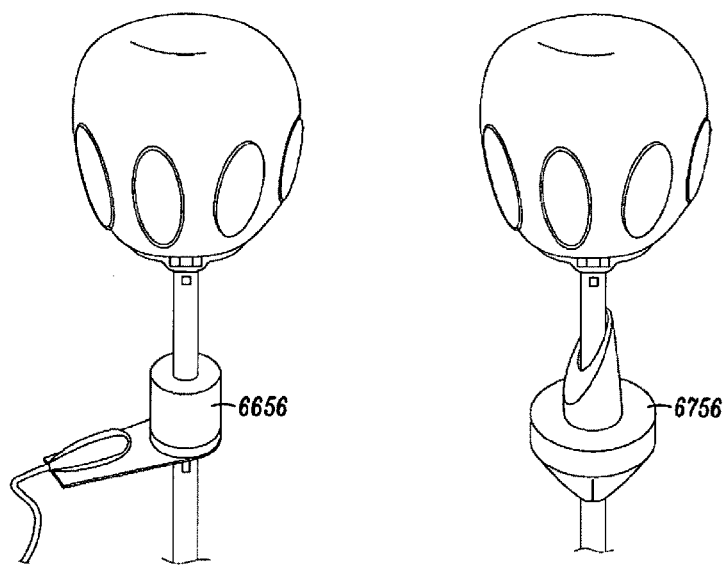
FIGS. 66-68 are embodiments of an electric coupling device that may be used with the neurophysiology system of FIG. 1, according to an alternate embodiment of the present invention.
Figure 68:
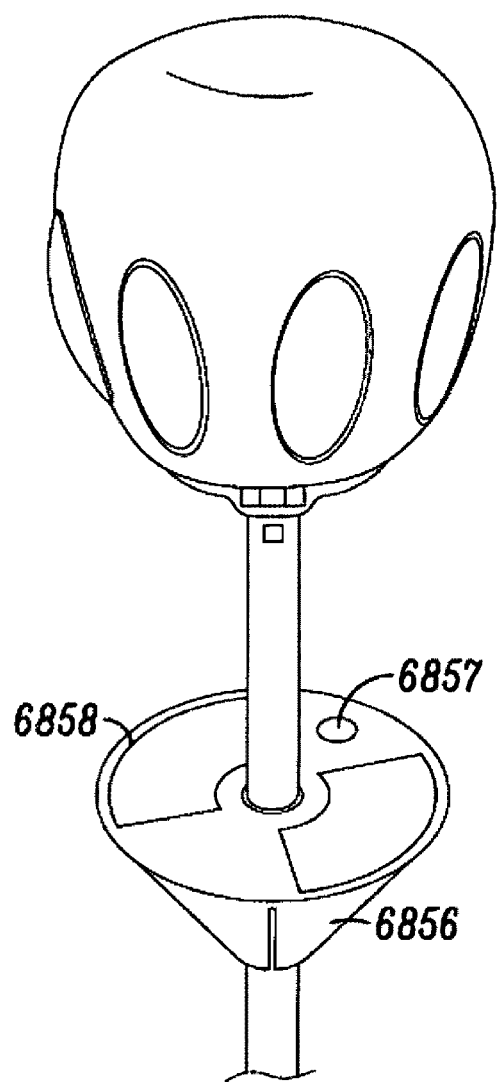

FIG. 66 illustrates a wired coupling device 6656, according to one embodiment. The device includes an internal cylinder that is configured to snugly receive the shaft of an instrument, as pictured. The internal cylinder contains two small rotating electrical conductors that allow the instrument to rotate free of the coupling device while still maintaining electrical contact. This prevents the wire from wrapping around the instrument during use. Stimulation may be triggered from either the probe handle to which the device is attached, or from the main display 34, if (for example) the coupling device is attached directly to the patient module 14. FIG. 67 illustrates an example of a wireless electric coupling device 6756. The wireless coupling device contains a wireless receiver for communicating with the neurophysiology system 10. Batteries are provided inside the wireless coupling device for powering the stimulation signals. FIG. 68 illustrates by way of example only, another embodiment of a wireless electric coupling device 6856. A wireless receiver is provided for communicating with the neurophysiology system 10. An activation button 6857 is also provided directly on the coupling device 6856 to allow stimulation to be initiated directly from the device. Disposable LED displays 6858 are also provided for displaying neurophysiologic data, such as for example, neurophysiologic test results (e.g. stimulation thresholds, etc . . . ). The dual displays ensure the reading never has to be read at greater than 90°.

Figure 69A:
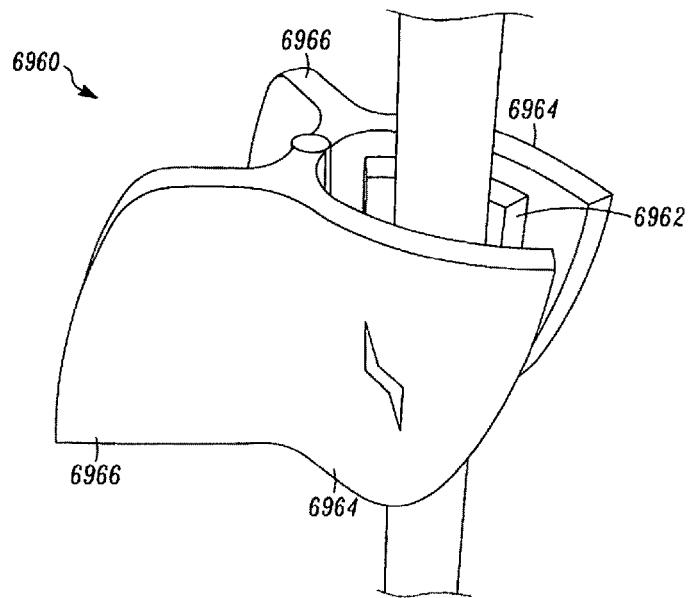
FIGS. 69A-69B are embodiments of an electric coupling device that may be used with the neurophysiology system of FIG. 1, according to another alternate embodiment of the present invention.
Figure 69B:
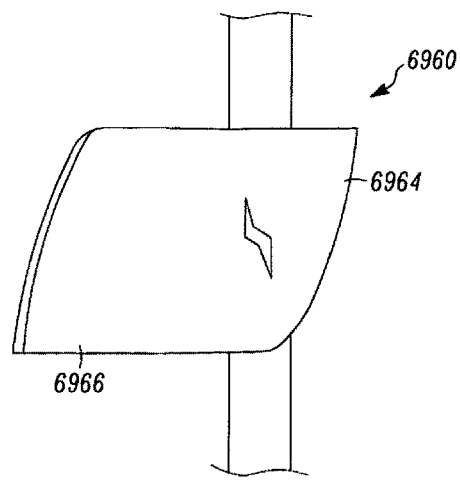
Figure 70A:
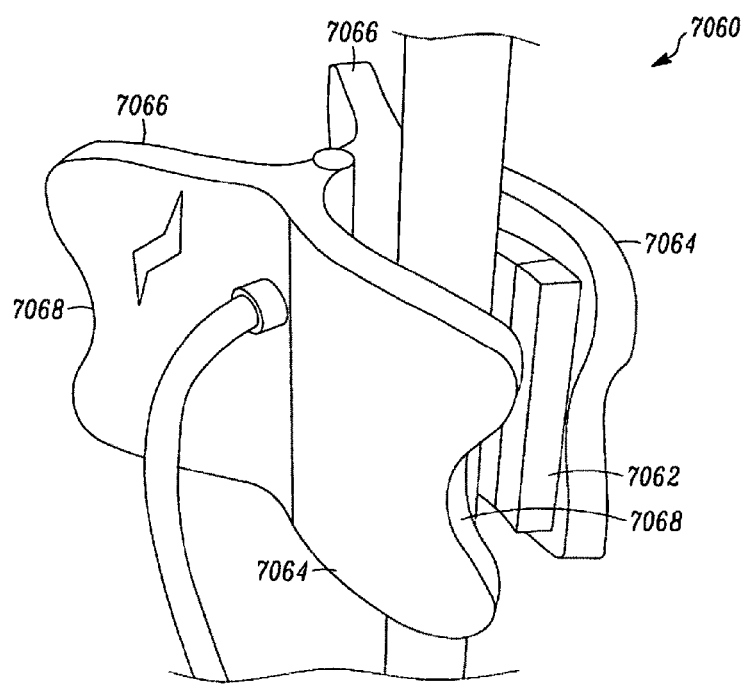
FIGS. 70A-70B are embodiments of an electric coupling device that may be used with the neurophysiology system of FIG. 1, according to an still another alternate embodiment of the present invention.
Figure 70B:
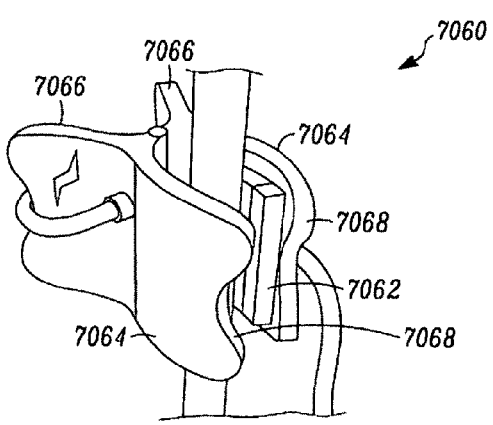

FIGS. 69-70 illustrate different example embodiments of electric coupling devices employing a "butterfly" clip 6960 design. In the embodiment of FIGS. 69A-69B, metal contacts 6962 are provided on the inside of each of the front wings 6964. The front wings are spring biased towards each other such that the metal contacts 6962 maintain contact with the instrument in use. Squeezing the back wings 6966 toward each other separates the front wings allowing the instrument to be inserted between the metal contacts. Although not shown, the butterfly clip may be attached to a probe handle, patient unit, or hub, via a wire. The example embodiment shown in FIG. 70A-70B includes features like those just described, including front wings 7064, back wings 7066, and metal contacts 7062, along with an additional pair of grooves 7068 provided in the front and back wings. The grooves allow the wire to coil around the clip in an orderly fashion.

Figure 71A:
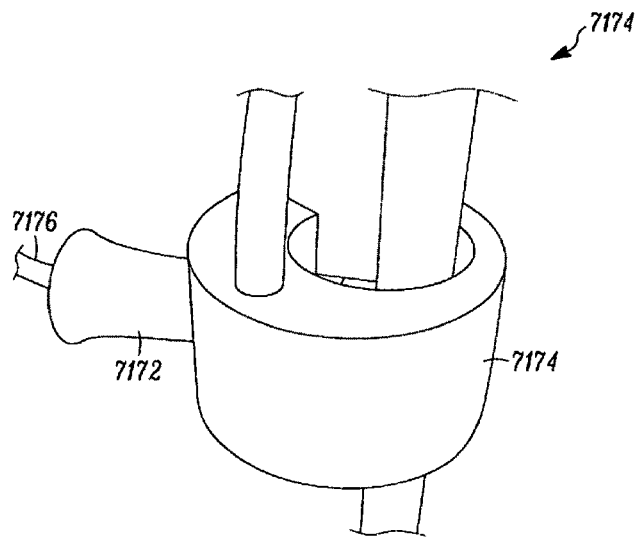
FIGS. 71A-71B are embodiments of an electric coupling device that may be used with the neurophysiology system of FIG. 1, according to one more alternate embodiment of the present invention.
Figure 71B:
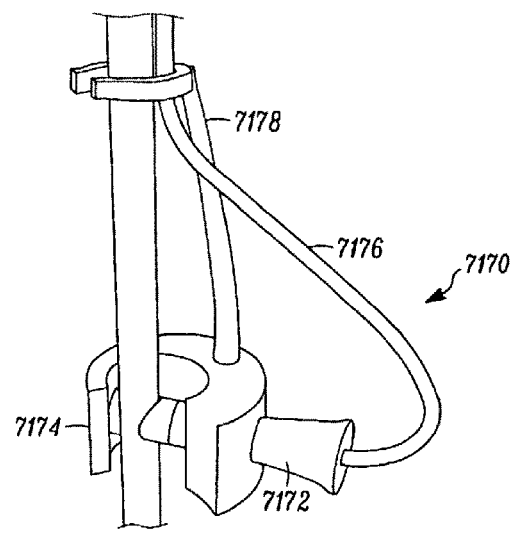
Figure 72A:
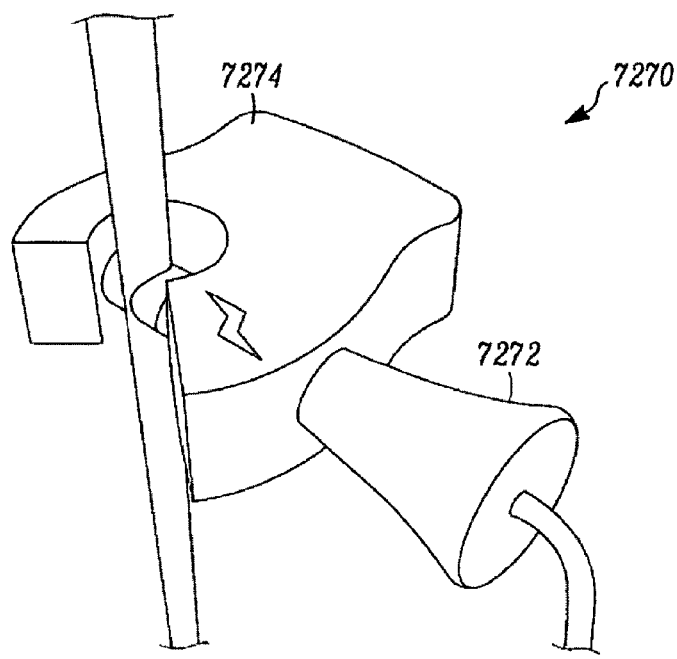
FIGS. 72A-72B are embodiments of an electric coupling device that may be used with the neurophysiology system of FIG. 1, according to still one more alternate embodiment of the present invention.
Figure 72B:
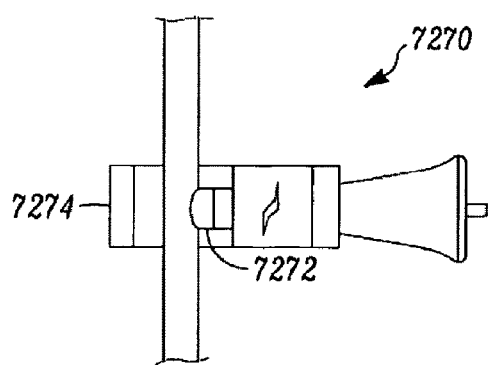
Figure 73:
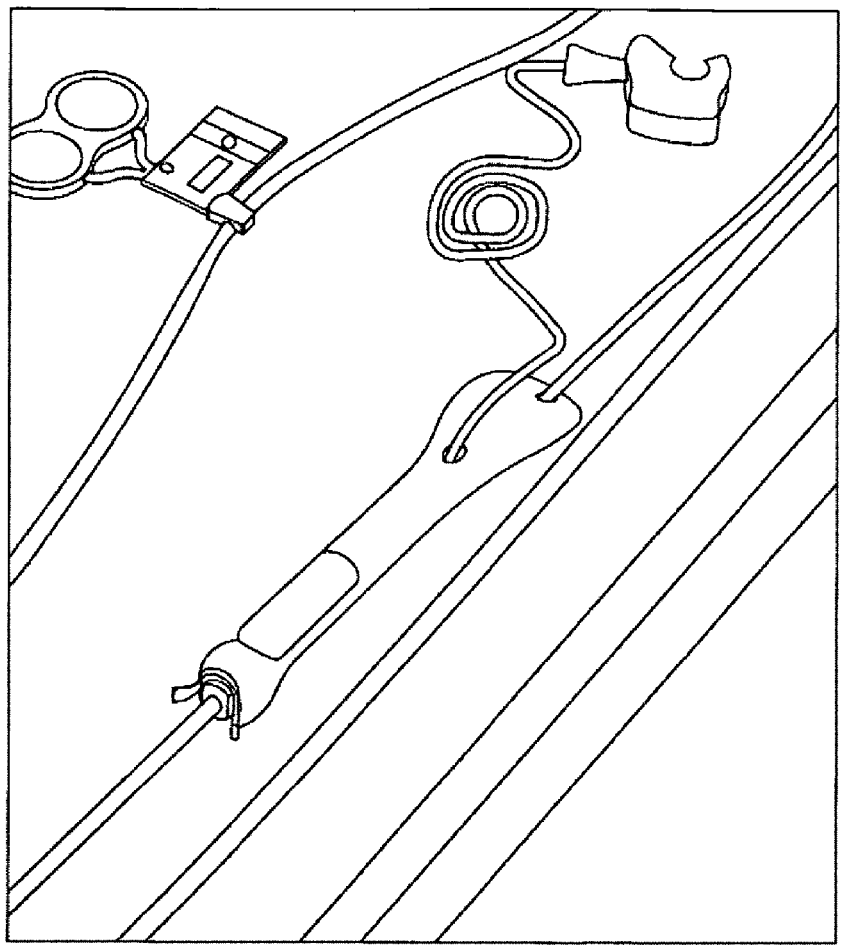
FIG. 73 is a perspective view of the electric coupling device of FIG. 72A-72B plugged into the probe of FIG. 65.

FIGS. 71-72 illustrate example embodiments of electric coupling devices employing a "plunger" style clip 7170 design. In the embodiment pictured in FIGS. 71A-71B, a spring-loaded plunger 7172 is provided to hold the surgical tool and transmit the stimulation signal. The plunger 7172 is composed of a conductive material such as metal. At least a portion of the conductive material of the plunger may be insulated such that only the tip used for contacting the tool is uncoated. A wire 7176 connects the plunger to a stimulation handle, patient module or hub. Pulling on the tail end of the plunger exposes an opening between the nonconductive housing 7174 and the uninsulated end of the plunger. The shaft of the surgical instrument may be placed in this opening and the plunger released. This will attach clip to the instrument. A wire fixator 7178 may also be provided that allows the wire coil to move away from the area of electrical contact and thereby reduces the risk that uncoiling the wire will have an impact on the contact. The example embodiment pictured in FIGS. 72A-72B includes the features just described but the shape of the nonconductive housing is different. An enlarged handle area is provided for easy handling during attachment and detachment. The area adjacent the handle is shaped so that fingers adding counter pressure will have less slippage when the clip is being used with a single hand. FIG. 73 illustrates the electric coupling device of FIG. 72 attached to a probe handle at a rear receptacle, allowing the coupling device to be attached to the handle at the same time as another probe tip.

As previously discussed, the neurophysiology system 10 may employ various electrodes to conduct the different the neurophysiologic assessments it performs. By way of example only, the system may employ EMG recording electrodes positioned over various muscles of the body to detect muscle response to stimulation signals. The placement of electrodes depends upon various factors including, for example, the function being performed and the applicable spinal level. By way of example, during lumbar surgery recording electrodes may be positioned over muscles of the lower extremities. For cervical procedures and/or during cord monitoring (e.g. via MEP mode) electrodes may be positioned over muscles of the upper extremities, or a combination of upper extremities and lower extremities. Recording electrodes may also be dispersed over the scalp for monitoring during SSEP mode. In addition to recording electrodes, the neurophysiology system 10 may also utilize stimulation electrodes to deliver stimulation signals to a selected target site. By way of example only, stimulation electrodes may be positioned on the scalp for MEP stimulation. Stimulation electrodes may also be placed over one or more peripheral nerves for SSEP stimulation and/or neuromuscular pathway assessment. While the electrodes have been described as being surface electrodes, it should be appreciated that various other types of electrodes may be used as well, such as, by way of example only, needle electrodes and corkscrew electrodes.

Figure 74:
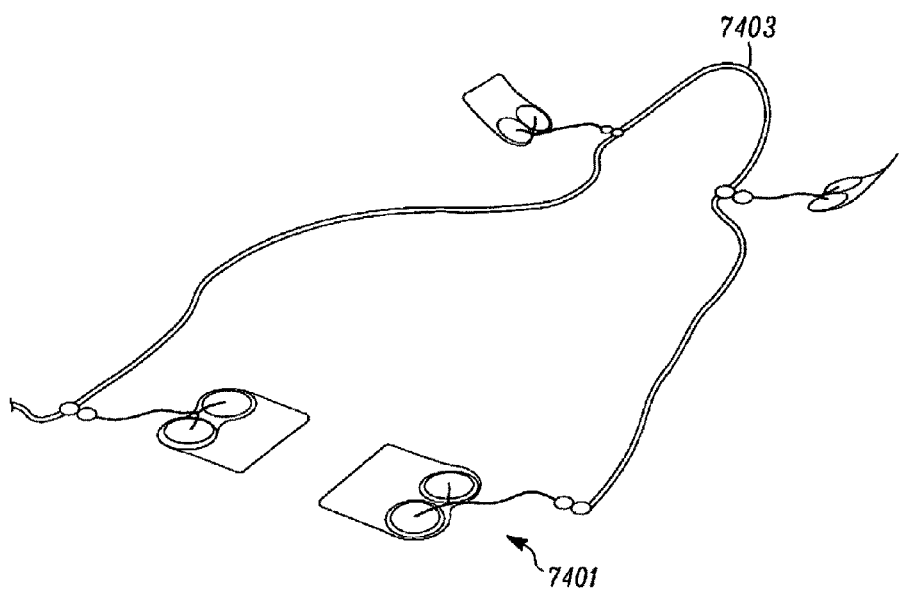
FIG. 74 is a perspective view of an electrode harness for use with the neurophysiology system of FIG. 1, according to another alternate embodiment of the present invention.
Figure 75:
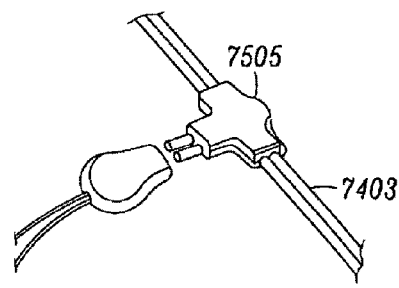
FIG. 75 is a perspective view of an electrode connector for use with the electrode harness of FIG. 74.

FIG. 74 depicts, by way of example only, and electrode harness 7401. The harness may connect to the patient module 14 at a single connection point. The various wires of the harness are bound throughout to create the appearance of a serial wire 7403 and eliminate wire clutter. Connectors 7501, such as that shown by way of example only, in FIG. 75 may be positioned about the serial-like wire so that when the wire is wrapped around the correct portion of the patient's body the electrode connectors 7505 are aligned in the proper position for placement of the electrodes. It should be understood that while four pairs of electrodes are shown attached to the harness in FIG. 74, the number of electrode pairs may vary and in a preferred embodiment the number of paired electrodes may be 16.

Figure 76:
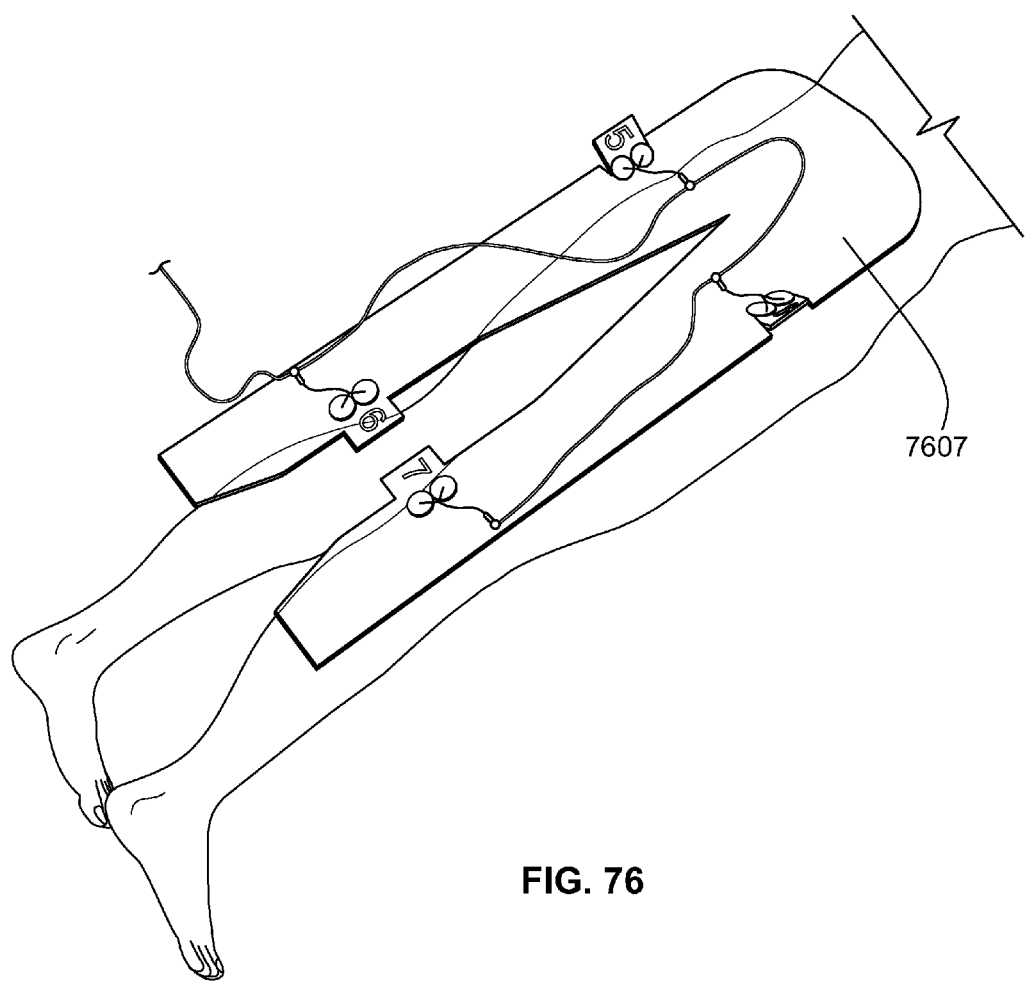
FIG. 76 is a perspective view of an electrode template that may be used with the electrode harness of FIG. 74.

FIG. 76 illustrates an embodiment of an electrode placement template 7607, shown by way of example only. The template 7607 may be made from light plastic sheeting. The shape of the template corresponds to that of the body portion to which the electrodes will be attached. The template 7607 may thus be spread over the corresponding body portion to position the attached electrodes in the proper position. The electrodes may be attached to the template as perforated tabs such that the template sheet may be torn off after the electrodes are positioned. The template sheet may also be used to print additional written or graphic information, such as, by way of example only, the label code and/or body graphic (corresponding to the labels 86 described previously).

Figure 77:
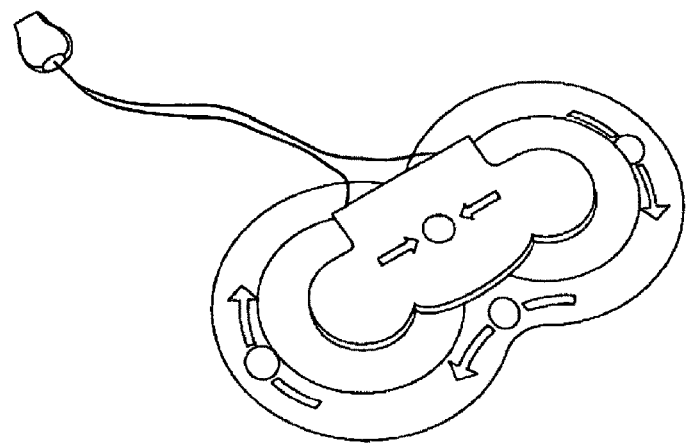
FIG. 77 is an electrode that that may be used with the neurophysiology system of FIG. 1, according to an alternate embodiment of the present invention.
Figure 78:
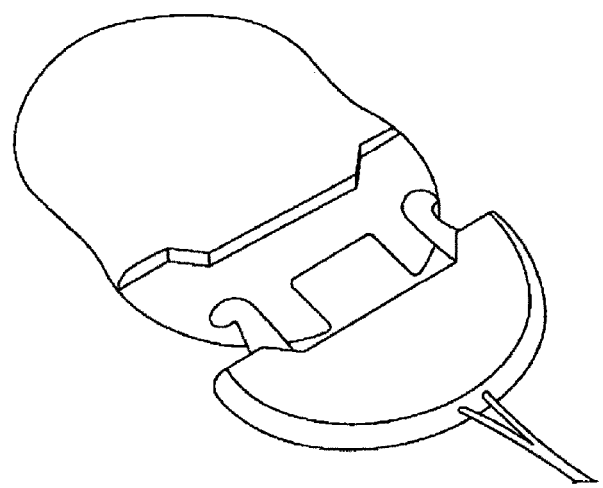
FIG. 78 is an electrode that that may be used with the neurophysiology system of FIG. 1, according to another embodiment of the present invention.

FIGS. 77-78 illustrate, by way of example only, embodiments of alternate electrodes for use with the neurophysiology system 10. The electrode in FIG. 77 is a self-prepping dual electrode. Instructions for prepping the electrodes are preferably implemented into the design scheme of the electrodes themselves. The electrode embodiment shown in FIG. 78 is a safety inspired needle electrode. The needles are hidden inside the casing until the electrode is snapped into the electrode harness connector, preferably after placement of the electrode on the skin. The snapping in of the connector drives the needles under the skin, preferably at a shallow angle. An adhesive may be applied to the electrode casing to anchor placement on the skin. The slim design of the casing makes it possible for the patient to roll on the electrode without disturbing or pulling out the needles. By ejecting the needles after the electrode is placed on the skin, the risk of accidental injury to the user is diminished.

Figure 79A:
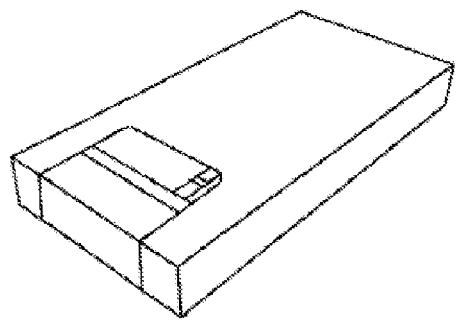
FIGS. 79A-79C are perspective views of a group of color coded accessory packages that may be used with the neurophysiology system of FIG. 1, according to an alternate embodiment of the present invention.
Figure 79B:
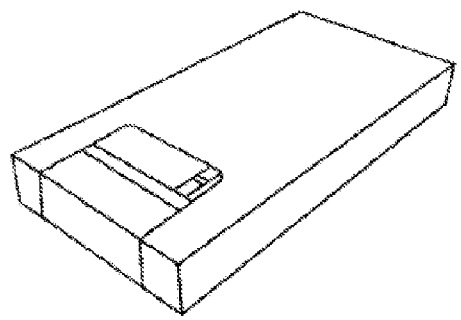
Figure 79C:
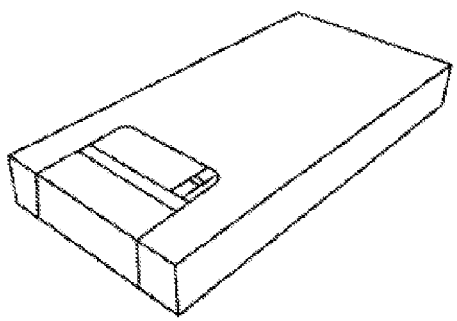
Figure 80:
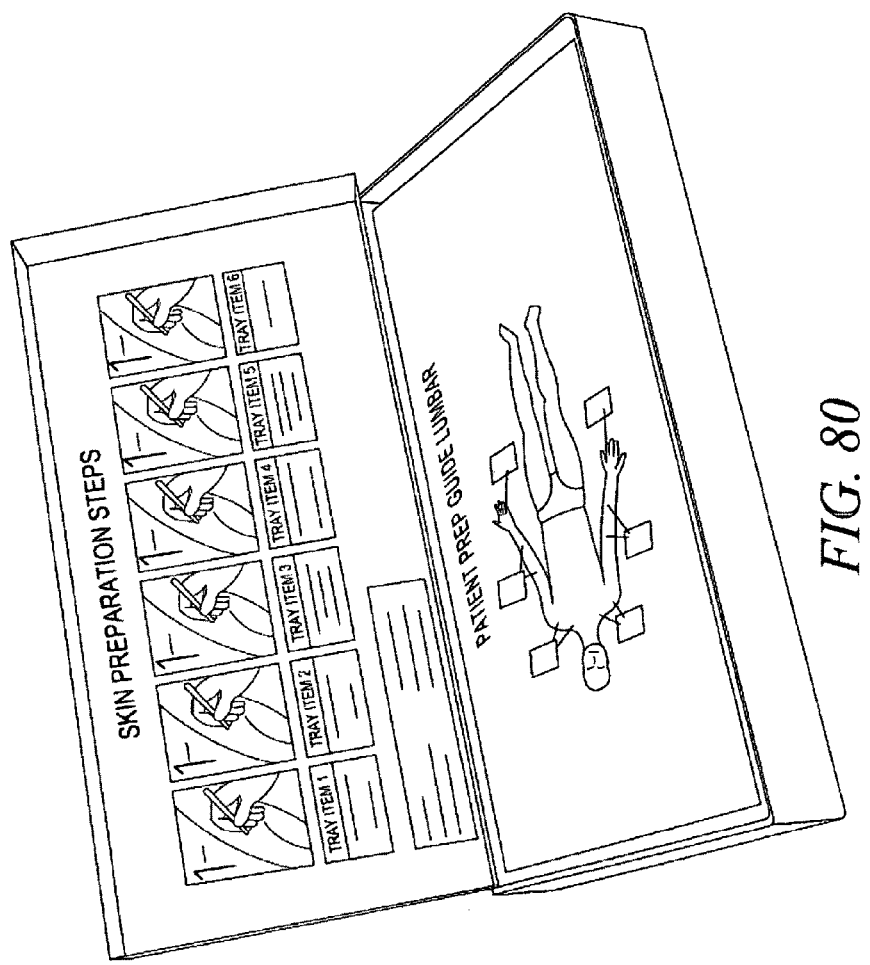
FIG. 80 is a perspective view of the inside of the box of FIG. 79A.

As previously described, the neurophysiology system 10 may preferably employ a color code system wherein each modality has a unique color associated with it. By way of example only and as shown herein, EMG monitoring may be associated with the color green, MEP monitoring with the color blue, and SSEP monitoring with the color orange. Utilizing this color code (or any other possible code, e.g. numerical, etc . . . ), disposables (i.e. electrodes and harnesses, stimulation accessories, etc . . . ) may be efficiently packaged for specific modalities. The electrodes within the package may be tagged accordingly and unnecessary components may be left out. In one embodiment, illustrated by way of example in FIGS. 79A-79C the entire package is colored according to the color code. Labels may include additional information such as for example, the spinal level (e.g. lumbar, cervical, or thoracolumbar), and whether the box contains needles or surface electrodes. FIG. 80 illustrates by way of example only, the interior of the disposable package of FIG. 79A. The interior of the box may contain instructions matching the graphical style of the GUI display. An instruction card is included with a first side of the card illustrating electrode placement from an anterior view and the other side of the card illustrating placement of the electrodes from a posterior view. The sides of the card and each individual site are numbered to make the order and placement clear. Instructions may also be positioned on the interior lid of the box that may open halfway to present a sort of stand for the instructions, such that they are easily viewable without needing to hold the instruction card or stand over top of it.

Figure 81:
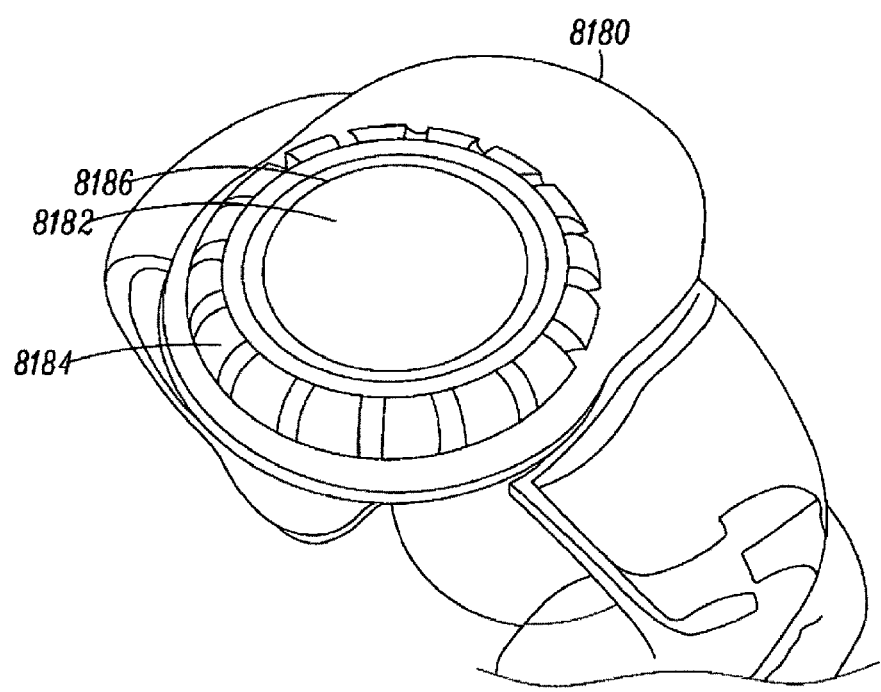
FIG. 81 is a perspective view of a forearm controller that may be used with the neurophysiology system of FIG. 1, according to an alternate embodiment of the present invention.

A variety of secondary feedback devices may be provided with the system 10. With reference to FIG. 81 there is shown (by way of example only) a wireless forearm controller 8180 preferably used to augment the functions of the control unit 12 and display 34. The forearm controller is designed to be worn on the arm of the surgeon or other OR personnel and includes a display piece 8182, a control dial 8184, and a selector button 8186. Multiple forearm controllers may be linked to the system 10 and worn by multiple OR personnel. The display piece 8182 may be an LED based display and can be used to show data such as the present stimulation current level and threshold results. Multiple colored LEDS may be included to indicate the data function and/or significance. By way of example only, red, yellow, and, green LEDS may be included and threshold results may be displayed according to the color code (e.g. green for results at predetermined safe levels, red for results at predetermined unsafe levels, and yellow for results in-between the predetermined safe and unsafe levels). Stimulation current levels can be displayed using a combination of all three LED colors to distinguish them from threshold levels. The control dial 8184 may be rotated to cycle through and highlight selection possibilities on a main display, such as GUI display 34, or, alternatively to actively change selected settings. The display piece 8182 may be depressible and thus embody the selector button 8186. Alternatively, a separate button (not shown) may be positioned elsewhere on the forearm controller. Together the control dial 8184 and selector button 8186 allow the wearer to navigate the different functions available on the system 10 regardless of their proximity to the control unit 12 and main display 34. When worn by the surgeon the forearm controller also allows the surgeon to view results and change settings without removing his hands or looking away from the surgical field. The forearm controller may be equipped to emit auditory or tactile feedback similar to that described earlier for probe 116. The forearm controller is sterilizable to allow use in the surgical field and adjustable to fit different users. In one example, the display piece may be disposable and the reminder of the controller may be autoclavable.

Figure 82:
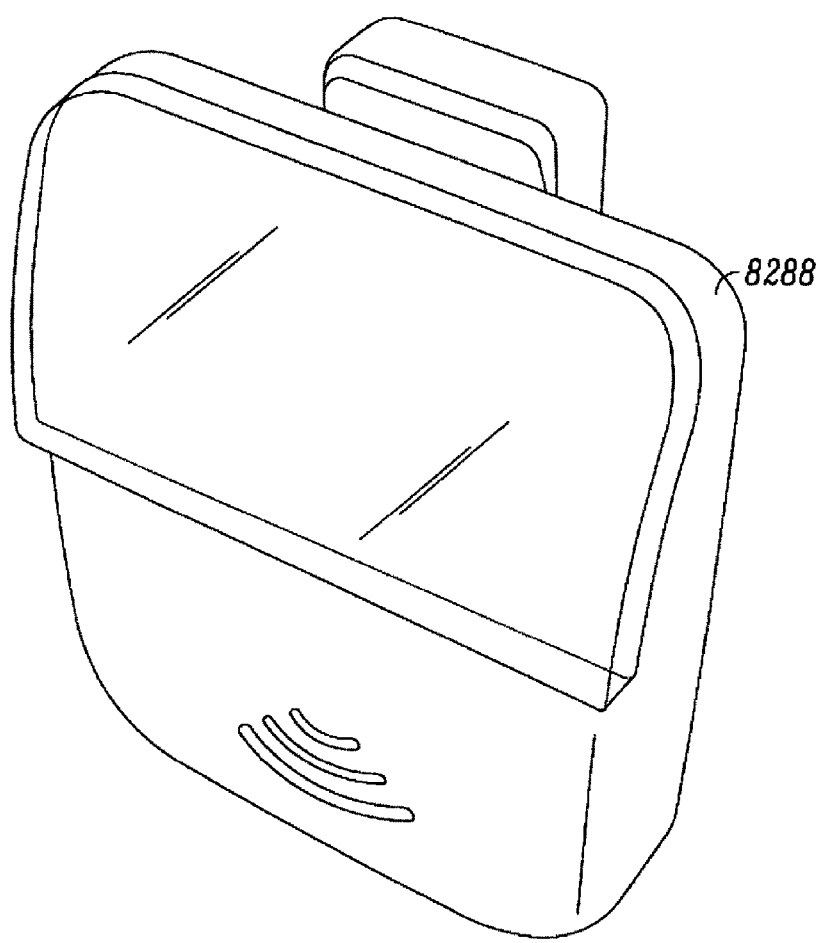
FIG. 82 is a perspective view of a haptic pager that may be used with the neurophysiology system of FIG. 1, according to an alternate embodiment of the present invention.

With reference to FIG. 82, there is shown a wireless sensory notification device (SND) 8288 used, in one example, to enhance the feedback provided by the main display 34. The SND may be worn by the surgeon or other OR personnel. Multiple SND's may be linked to the system 10 and therefore utilized by multiple OR personnel. The SND includes a clip for attaching the device to the wearer's clothing. Alternatively, the SND may be attached to a lanyard, chain, necklace, etc . . . and worn around the wearer's neck. The SND may be configured to provide threshold result feedback via visual display, audible tones, and/or vibration.

In one example, visual feedback may be accomplished via a LED based display. Multiple colored LEDS such as, red, yellow, and, green LEDS may be included to incorporate the color code relating to different safety levels, as discussed above. The SND may emit an audible sound that corresponds to different threshold results. The pitch of the sound may change in response to different threshold levels. For example, when a determined threshold is in the safe (Green) range then a low pitch tone may be emitted. When the threshold result is in-between the safe and unsafe levels (Yellow) the sound may have a higher pitch. A still higher pitch may be emitted when the threshold result is in the unsafe (Red) range. Alternatively, a different sound volume may indicate different safety levels. In still another alternative, different sounds (e.g. ping, bell, siren etc . . . ) may be produced for each safety level. The vibratory action of the sensory notification device may operate in similar fashion to that of the sound function just described. That is, the vibration frequency and/or intensity may be altered depending on the safety level of the corresponding threshold result.

Figure 83:
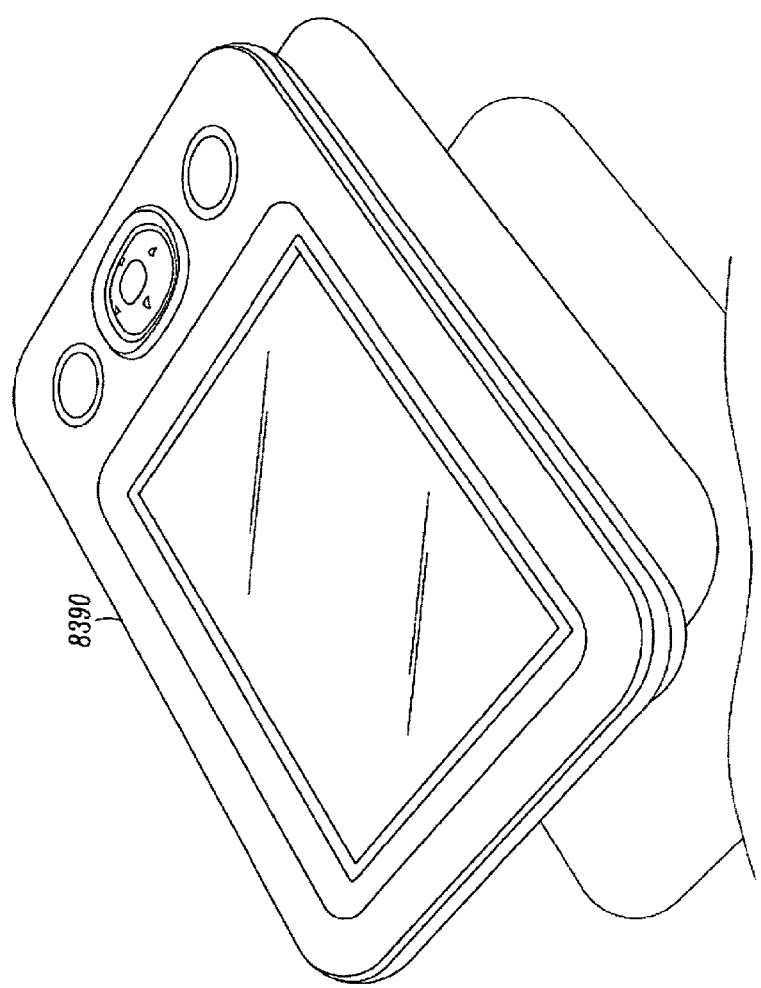
FIG. 83 is a perspective view of a mini controller that may be used with the neurophysiology system of FIG. 1, according to an alternate embodiment of the present invention.

FIG. 83 depicts, by way of example only, an embodiment of a mini controller 8390. The mini controller allows a user to control certain aspects of the system 10, such as by way of example only, the current function, audio level, and stimulation initiation, etc . . . . This may allow the main display to be positioned closer to the surgeon in or near the sterile field while still allowing others, such as a sales representative (by way of example), to manipulate certain aspects of the system. The mini controller includes a display. A wireless antenna may be included for communication with the system 10. Buttons are used for navigating and making selections. The mini controller may also collect data from the control unit 12 for later transfer to a PC.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope.

The invention claimed is:

1. A system for avoiding harm to neural tissue during surgery, comprising:
   an instrument capable of advancement to a surgical target site and configured to deliver a stimulation signal at least one of while advancing to said target site and after reaching said target site; and
   a processing system in communication with said instrument and programmed to perform a plurality of neurophysiologic testing functions including at least two of static pedicle integrity testing, dynamic pedicle integrity testing, nerve proximity detection, neuromuscular pathway assessment, manual motor evoked potential monitoring, automatic motor evoked potential monitoring, somatosensory evoked potential monitoring, non-evoked monitoring, and surgical navigation; said processing system programmed with a plurality of pre-established testing profiles corresponding to one or more of a specific surgical procedure and a specific spinal region being operated upon;
   wherein selection of a pre-established profile dictates which of the neurophysiologic testing functions are available for selection and sets specific test parameters associated with the available neurophysiologic testing functions so as to facilitate the initiation of said at least one neurophysiologic testing function;
   said processing system further programmed with a set of at least three threshold ranges and configured to direct a first stimulation signal to said instrument at a first magnitude corresponding to a boundary between a pair of said ranges, direct a second stimulation signal at a second magnitude corresponding to a boundary between a different pair of said ranges, and to measure at least one response of nerves depolarized stimulation signals by said stimulation signals to indicate at least one of nerve proximity and pedicle integrity.

2. The system of claim 1, wherein said pre-established profile is at least one of pre-programmed by a manufacturer of said system and saved by a user after creating said profile.

3. The system of claim 1, wherein said specific surgical procedures are comprised of ACDF, XLIF, and decompression surgical procedures.

4. The system of claim 1, wherein said specific spinal regions are comprised of cervical, thoracolumbar, and lumbar.

5. The system of claim 1, wherein said specific test parameters are comprised of electrode placement, myotomes monitored, and stimulation signal parameters.

6. The system of claim 5, wherein the at least one evoked response is measured by monitoring neuromuscular waveforms of myotomes associated with said depolarized nerves.

7. The system of claim 1, wherein the at least one evoked response is an EMG response.

8. The system of claim 1, wherein said system includes a display for communicating said at least one of nerve proximity and pedicle integrity.

9. The system of claim 8, wherein said system indicates at least one of nerve proximity and pedicle integrity by displaying at least one of the colors red, yellow, and green.

10. The system of claim 9, wherein said processing system automatically determines a stimulation threshold after displaying said one of red, yellow, and green.

11. The system of claim 10, wherein said processing system augments the display of said one of red, yellow, and green with a numerical value after determining said threshold.

12. The system of claim 1, wherein said instrument is a device for forming a hole in a pedicle.

13. The system of claim 1, wherein said instrument is part of a system for establishing an operative corridor to a surgical target site.

14. The system of claim 13, wherein said operative corridor is a lateral approach to a spinal target site.

15. The system of claim 1, comprising a plurality of sensors for measuring said nerve responses.

16. The system of claim 15, wherein said plurality of sensors comprises at least one of an anode and a common electrode.

17. The system of claim 16, wherein said plurality of sensors connect to said processing system through a single connector.

18. The system of claim 17, wherein said single connector comprises an identifier that is recognized by said processing unit.

19. The system of claim 18, wherein the identification of said connector alters system parameters employed by said processing system.

* * * * *